US010501502B2

(12) United States Patent
Rodriguez et al.

(10) Patent No.: US 10,501,502 B2
(45) Date of Patent: Dec. 10, 2019

(54) ALLOPHYCOCYANIN ALPHA-SUBUNIT EVOLVED LABELING PROTEINS (SMURFPS)

(71) Applicants: The Regents of the University of California, Oakland, CA (US); Wendy M. G. Tsien

(72) Inventors: Erik Rodriguez, La Jolla, CA (US); John Lin, Del Mar, CA (US); Roger Tsien, Eugene, OR (US); Richard Ting, New York, NY (US); Geraldine Tran, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/821,574

(22) Filed: Nov. 22, 2017

(65) Prior Publication Data

US 2018/0201655 A1    Jul. 19, 2018

Related U.S. Application Data

(60) Provisional application No. 62/425,390, filed on Nov. 22, 2016.

(51) Int. Cl.
*C07K 14/195* (2006.01)

(52) U.S. Cl.
CPC .................................. *C07K 14/195* (2013.01)

(58) Field of Classification Search
CPC .................................................... C07K 14/195
See application file for complete search history.

(56) References Cited

U.S. PATENT DOCUMENTS 5,776,689 A    7/1998  Karin et al.

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Rodriguez et al., A far-red fluorescent protein evolved from a cyanobacterial phycobiliprotein. Nature Methods, 2016, vol. 13(9): 763-769. (Year: 2016).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Andrusier e al. "FireDock: Fast Interaction Refinement in Molecular Docking" Proteins, vol. 69, pp. 139-159 (2007).
Arciero et al. "In Vitro Attachment of Bilins to Apophycocyanin" The Journal of Biological Chemistry, vol. 263, No. 34, pp. 18343-18349 (1988).
Auldridge et al. "Structure-guided Engineering Enhances a Phytochrome-based Infrared Fluorescent Protein" The Journal of Biological Chemistry, vol. 287, No. 10, pp. 7000-7009.
Baldari et al. "A novel leader peptide which allows efficient secretion of a fragment of human interleukin 1 beta in *Saccharomyces cerevisia*" vol. 6, pp. 229-234 (1987).
Berndt et al. "Bi-stable neural state switches" Nature Neuroscience, vol. 12, pp. 229-234 (2009).
Berndt et al. "High-efficiency channelrhodopsins for fast neuronal stimulation at low light levels" Proceedings of the National Academy of Sciences, vol. 108, No. 18, pp. 7595-7600 (2011).
Bruchez et al. "Semiconductor Nanocrystals as Fluorescent Biological Labels" Science, vol. 281, pp. 2013-2016 (1998).
Buss et al. "The six amino-terminal amino acids of p60src are sufficient to cause myristylation of p21v-ras" Molecular and Cellular Biology, vol. 8, No. 9, pp. 3960-3963 (1988).
Chan et al. "Quantum Dot Bioconjugates for Ultrasensitive Nonisotopic Detection" Science, vol. 281, p. 2016-2018 (1998).
Chu et al. "Non-invasive intravital imaging of cellular differentiation with a bright red-excitable fluorescent protein" vol. 11, No. 5, pp. 572-582 (2014).
Filonov et al. "A Near-Infrared BiFC Reporter for in Vivo Imaging of Protein-Protein Interactions" Chem. Bio., vol. 20, pp. 1078-1086 (2013).
Filonov et al. "Bright and stable near-infrared fluorescent protein for in vivo imaging" Nature Biotechnology, vol. 29, pp. 757-761 (2011).
Filonov et al. "Deep-tissue photoacoustic tomography of genetically encoded iRFP probe" Angew. Chem. Int. Ed. Engl., vol. 51, No. 6, pp. 1448-1451 (2012).
Fischer et al. "Harnessing phytochrome's glowing potential" Proc. Natl. Acad. Sci., vol. 101, No. 50, pp. 17334-17339 (2004).
Gambetta et al. "Genetic engineering of phytochrome biosynthesis in bacteria" Proc. Natl. Acad. Sci., vol. 98, pp. 10566-10571 (2001).
Gautier et al. "An Engineered Protein Tag for Multiprotein Labeling in Living Cells" Chem. Biol., vol. 15, pp. 128-136 (2008).
Giepmans et al. "The Fluorescent Toolbox for Assessing Protein Location and Function" Science, vol. 312, pp. 217-224 (2006).
Gunaydin et al. "Ultrafast optogenetic control" Nature Neuroscience, vol. 13, pp. 387-392 (2010).

(Continued)

*Primary Examiner* — Ganapathirama Raghu
(74) *Attorney, Agent, or Firm* — Morgan, Lewis & Bockius LLP

(57) ABSTRACT

The invention provides evolved red-shifted smURFPs. In some embodiments, the smURFPs are characterized by a) increased Fluorescence of smURFP as compared to infrared FPs IFP1.4 and iRFP713; b) expressing efficiently with minimal toxicity; c) does not require a lyase to covalently attach its chromophore, wherein the chromophore is biliverdin; d) exhibit a wavelengths longer than attainable with jellyfish- or coral-derived FPs using smURFP and IFP2.0; e) allows for functional fusion to hCdt1(30/120) as compared to jellyfish- or coral-derived FPs mAG, eGFP, and mRFP1 which are nonfunctional; and f) allows for deep tissue imaging.

12 Claims, 28 Drawing Sheets
(28 of 28 Drawing Sheet(s) Filed in Color)
Specification includes a Sequence Listing.

(56) References Cited

OTHER PUBLICATIONS

Hancock et al. "A CAAX or a CAAL motif and a second signal are sufficient for plasma membrane targeting of ras proteins" EMBO Journal, vol. 10, No. 13, pp. 4033-4039 (1991).
Katayama et al. "GFP-Like Proteins Stably Accumulate in Lysosomes" Cell Structure and Function, vol. 33, pp. 1-12 (2008).
Kaufman et al. "Translational efficiency of polycistronic mRNAs and their utilization to express heterologous genes in mammalian cells" EMBO Journal, vol. 6, pp. 187-193 (1987).
Keppler et al. "A General Method for the Covalent Labeling of Fusion Proteins with Small Molecules in vivo" Nature Biotechnology, vol. 21, pp. 86-89 (2003).
Kleinlogel et al. "Ultra light-sensitive and fast neuronal activation with the Ca2+-permeable channelrhodopsin CatCh" Nature Neuroscience, pp. 513-518 (2011).
Krumholz et al. "Multicontrast photoacoustic in vivo imaging using near-infrared fluorescent proteins" Scientific Reports, vol. 4 (2014).
Kumagai et al. "A Bilirubin-Inducible Fluorescent Protein from Eel Muscle" Cell, vol. 153, pp. 1602-1611 (2013).
Larkin et al. "Clustal W and Clustal X version 2.0" Bioinformatics Applications Note, vol. 23, No. 21, pp. 2947-2948 (2007).
Levine et al. "Isolation and characterization of a photoprotein, "phialidin", and a spectrally unique green-fluorescent protein from the bioluminescent jellyfish Phialidium gregarium" Comparative Biochemistry and Physiology., vol. 72, pp. 77-85 (1982).
Li et al. "Continuous Fluorescence Assay of Phytochrome Assembly in vitro" Biochemistry, vol. 34, pp. 7923-7930 (1995).
Li et al. "Engineering Dark Chromoprotein Reporters for Photoacoustic Microscopy and FRET Imaging" Scientific Reports, vol. 6 (2016).
Lin et al. "Characterization of Engineered Channelrhodopsin Variants with Improved Properties and Kinetics" Biophysical Journal, vol. 96, pp. 1803-1814 (2009).
Lin et al. "ReaChR: A red-shifted variant of channelrhodopsin enables deep transcranial optogenetic excitation" Nat. Neurosci., vol. 16, No. 10, pp. 1499-1508 (2013).
Liu et al. "Crystal Structure of Allophycocyanin from Red Algae Porphyra yezoensis at 2.2-Å Resolution" Journal of Biochemistry, vol. 274, pp. 16945-16952 (1999).
Los et al. "The HaloTag: A Novel Protein Labeling Technology for Cell Imaging and Protein Analysis" ACS Chem. Biol., vol. 3, No. 6, pp. 373-382 (2008).
Matz et al. "Fluorescent proteins from nonbioluminescent Anthozoa species" Nature Biotechnology, vol. 17, No. 10, pp. 969-973 (1999).
Miyawaki et al. "Development of Probes for Cellular Functions Using Fluorescent Proteins and Fluorescence Resonance Energy Transfer" Annu. Rev. Biochem., vol. 80, (2011).
Moore et al. "Recovery of Red Fluorescent Protein Chromophore Maturation Deficiency through Rational Design" PLoS ONE, vol. 7, Issue 12 (2012).
Nagel et al. "Light Activation of Channelrhodopsin-2 in Excitable Cells of Caenorhabditis elegans Triggers Rapid Behavioral Responses" Current Biology, vol. 15, Issue 24, pp. 2279-2284 (2005).
Pettersen et al. "UCSF Chimera—A Visualization System for Exploratory Research and Analysis" J. Comput. Chem., vol. 25, pp. 1605-1612 (2004).
Rumyantsev et al. "Minimal Domain of Bacterial Phytochrome Required for Chromophore Binding and Fluorecence" Scientific Reports, vol. 5, No. 18348 (2015).
Sakaue-Sawano et al. "Drug-induced cell cycle modulation leading to cell-cycle arrest, nuclear mis-segregation, or endoreplication" BMC Cell Bio., vol. 12, pp. 1-12 (2011).
Sakaue-Sawano et al. "Visualizing Spatiotemporal Dynamics of Multicellular Cell-Cycle Progression" Cell, vol. 132, pp. 487-498 (2008).
Sako et al. "Single-molecule imaging of EGFR signalling on the surface of living cells" Nature Cell Biology, vol. 2, pp. 168-172 (2000).
Sambrook et al. "Molecular Cloning: A Laboratory Manual Second Edition" Cold Spring Harbor Laboratory Press (1989).
Schneider et al. "NIH Image to ImageJ: 25 years of Image Analysis" Nat. Methods, vol. 9, No. 7, pp. 671-675 (2012).
Schneidman-Duhovny et al. "PatchDock and SymmDock: servers for rigid and symmetric docking" Nucleic Acids Research, vol. 33, pp. W363-W367 (2005).
Shaner et al. "A guide to choosing fluorescent proteins" Nature Methods, vol. 2, No. 12, pp. 905-909 (2005).
Shaner et al. "Improved monomeric red, orange and yellow fluorescent proteins derived from Discosoma sp.red fluorescent protein" Nature Biotechnology, vol. 22, No. 12, pp. 1567-1572 (2004).
Shcherbakova et al. "Molecular Basis of Spectral Diversity in Near-Infrared Phytochrome-Based Fluorescent Proteins" Chem. Biol., vol. 22, pp. 1540-1551 (2015).
Shcherbakova et al. "Near-infrared fluorescent proteins for multicolor in vivo imaging" Nat. Methods, vol. 10, No. 8, pp. 751-754 (2013).
Shu et al. "Mammalian expression of infrared fluorescent proteins engineered from a bacterial phytochrome" Science, vol. 5928, pp. 804-807 (2009).
Smith et al. "Production of human beta interferon in insect cells infected with a baculovirus expression vector" Mollecular and Cellular Biology, vol. 3, No. 12, pp. 2156-2165 (1983).
Toettcher et al. "Light Control of Plasma Membrane Recruitment Using the Phy-Pif System" Methods Enzymol., pp. 409-423 (2011).
Tomura et al. "Contrasting Quiescent G0 Phase with Mitotic Cell Cycling in the Mouse Immune System" PLoS One, vol. 8, Issue 9 (2013).
Tooley et al. "Biosynthesis of a fluorescent cyanobacterial C-phycocyanin holo-subunit in a heterologous host" Proc. Natl. Acad. Sci., vol. 98, No. 19, pp. 10560-10565 (2001).
Tromberg et al. "Non-Invasive In Vivo Characterization of Breast Tumors Using Photon Migration Spectroscopy" Neoplasia, pp. 26-40 (2000).
Tsien et al. "Constructing and Exploiting the Fluorescent Protein Paintbox (Nobel Lecture)" Angew. Chem. Int. Ed., vol. 48, pp. 5612-5626 (2009).
Tsien et al. "The Green Fluorscent Protein" Annu. Rev. Biochem., vol. 67, pp. 509-544 (1998).
Tubbs et al. "Crystallographic Structures of Discosoma Red Fluorescent Protein with Immature and Mature Chromophores: Linking Peptide Bond Trans-Cis Isomerization and Acylimine Formation in Chromophore Maturation" Biochemistry, vol. 44, pp. 9833-9840 (2005).
Veal et al. "Hydrogen Peroxide Sensing and Signaling" Mol. Cell, vol. 26, pp. 1-14 (2007).
Wahleithner et al. "Expression and Assembly of Spectrally Active Recombinant Holophytochrome" Prob. Natl. Acad. Sci., vol. 88, pp. 10387-10391 (1991).
Ward et al. "Spectral Perturbations of the Aequorea Green-Fluorescent Protein" Photochemistry and Photobiology, vol. 35, Issue 6, pp. 803-808 (1982).
Weber et al. "Contrast Agents for Molecular Photoacoustic Imaging" Nat. Methods, vol. 13, No. 8, pp. 639-650 (2016).
Weitzman et al. "Inflammation and Cancer: Role of Phagocyte-Generated Oxidants in Carcinogenesis" Blood, vol. 76, No. 4, pp. 655-663 (1990).
Wen et al. Opto-Current-Clamp Actuation of Cortical Neurons Using a Strategically Designed Channelrhodopsin, vol. 5, Issue 9 (2010).
Yao et al. "Multi-scale photoacoustic tomography using reversibly switchable bacterial phytochrome as a near-infrared photochromic probe" Nat. Methods, vol. 13, No. 1, pp. 67-73 (2016).
Yeh et al. "Fluorescence Properties of Allophycocyanin and a Crosslinked Allophycocyanin Trimer" Cytometry, vol. 8, pp. 91-95 (1987).
Yu et al. "A naturally-monomeric infrared fluorescent protein for protein labeling in vivo" Nat. Methods, vol. 12, No. 8, pp. 763-765 (2015).
Yu et al. "An improved monomeric infrared fluorescent protein for neuronal and tumour brain imaging" Nature Communications, vol. 5 (2014).
Yu et al. "Rational design of a monomeric and photostable far-red fluorescent protein for fluorescence imaging in vivo" Protein Science, vol. 25, pp. 308-315 (2016).

(56) References Cited

OTHER PUBLICATIONS

Zhang et al. "Fused-Gene Approach to Photoswitchable and Fluorescent Biliproteins" Angew. Chem. Int. Edn. Engl., vol. 49, 5456-5458 (2010).

* cited by examiner

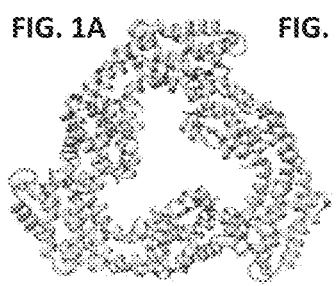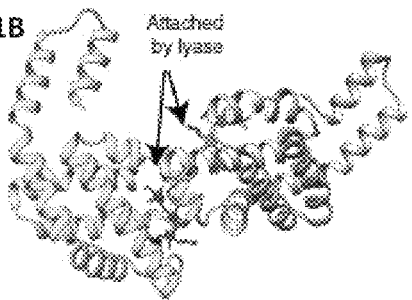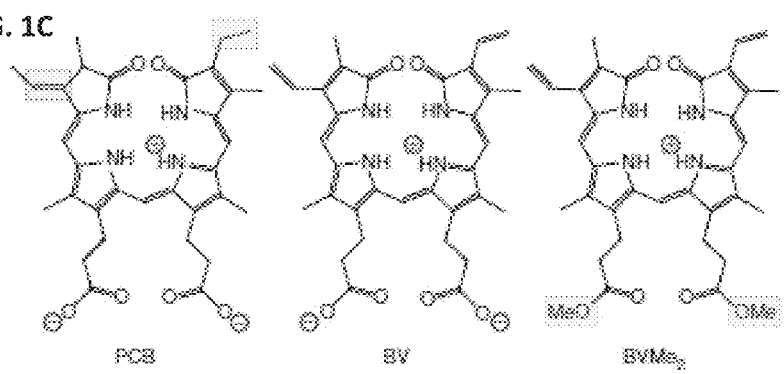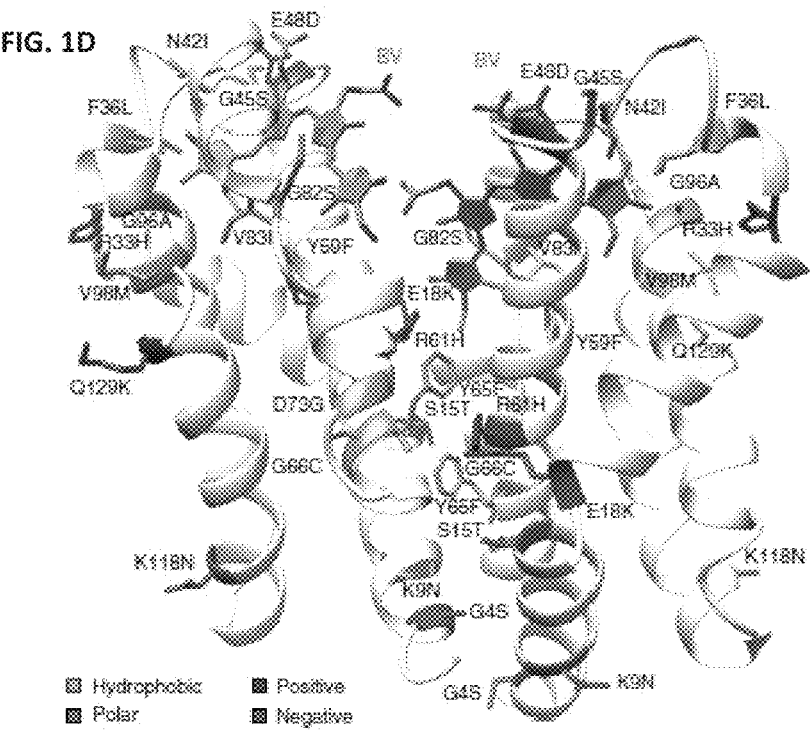

FIG. 2A
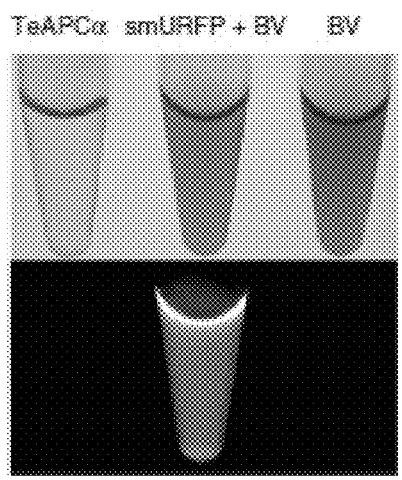
FIG. 2B
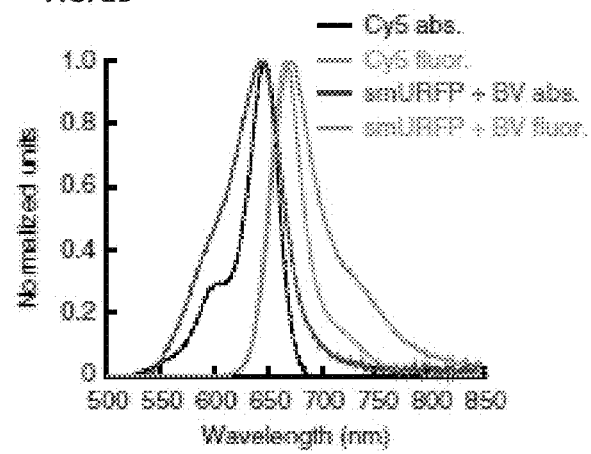
FIG. 2C
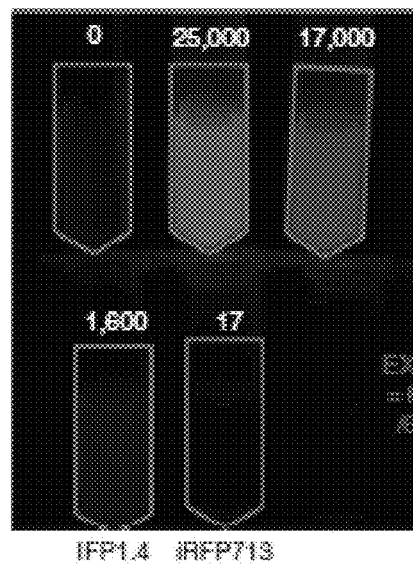
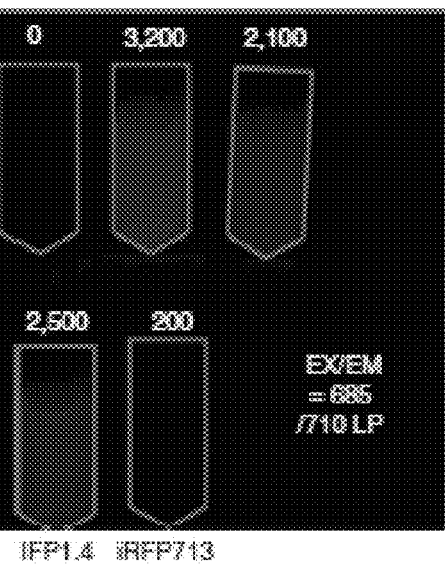

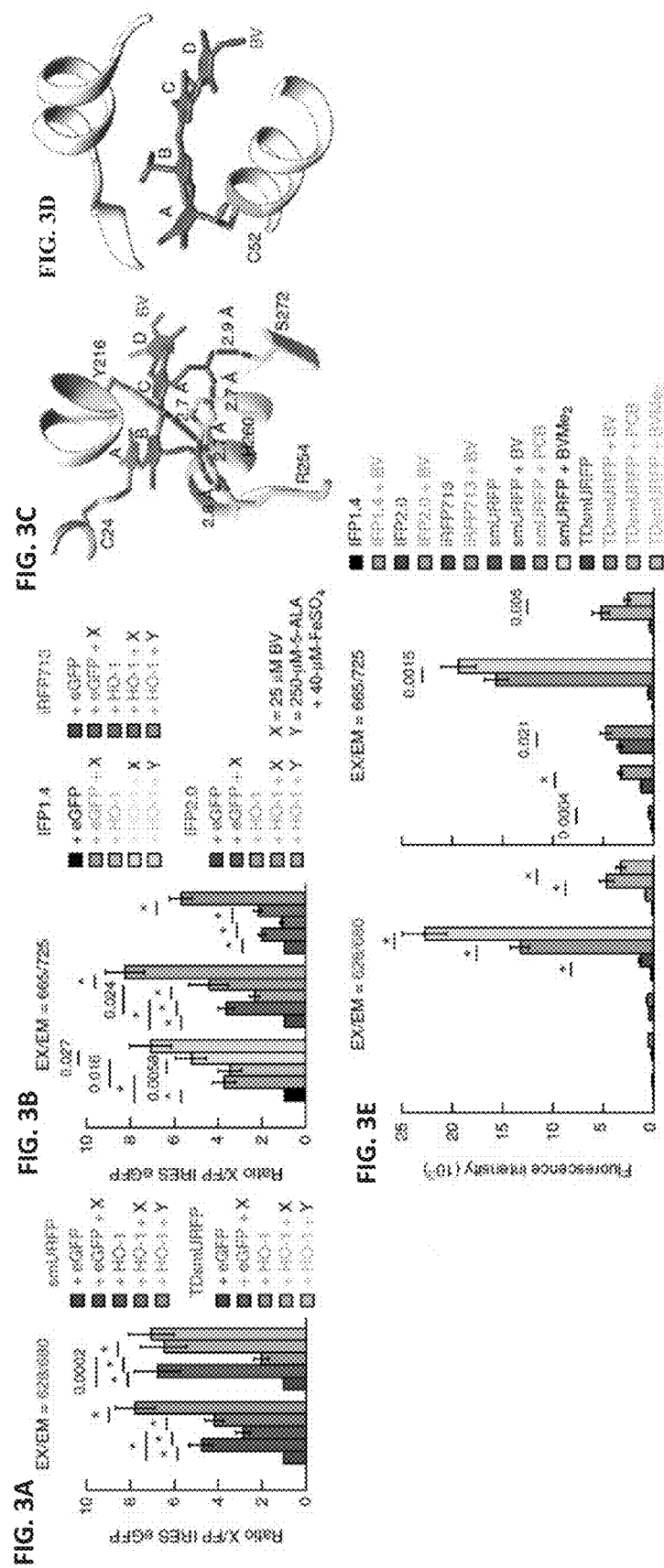

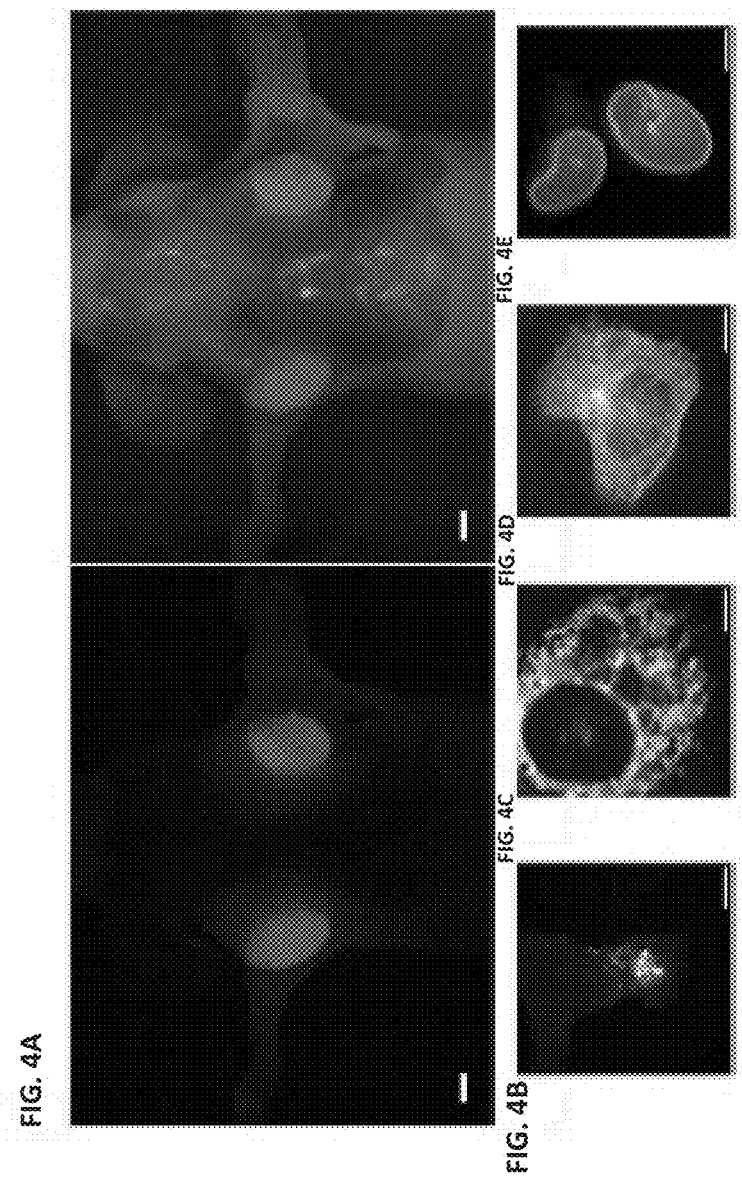

FIG. 6

```
            -29          -20          -10           1            11           21
Consensus   MSTVSQVILQ   ADDELRYPST   GELQSIKDFL   KTGEQRVRIA   TTLSENEKKI
Conservation                                       ;*::*::**    ::::..:*
TeAPCα      ..........   ..........   .........M   KTGEQRYKIA   TLLSENEKKI
MvAPCα      MSVVSQLILQ   ADDELRYPST   GELQSIKDFL   KTGEQRVRIA   TALSDSERKI
OnAPCα      MSVVSQLILQ   ADDELRYPST   GELQSINDFF   KTGEQRVRIA   TALSDSEKKI
CyAPCα      MSVVSQVLLQ   ADDELRYPSA   GELKSLQDFF   QTGEQRMRIA   TTLSENEKRI
LaAPCα      MTVVSQVILK   ADDELRYPST   GELQNISDFL   KTGEQRVRIA   TTLSENEKKI
LyAPCα      MTVVSQVILK   ADDELRYPST   GELQNISDFL   KTGEQRVRIA   TTFSENEKKI
PyAPCα      MSIVTKSIVN   ADAEARYLSP   GELDRIKSFV   LSGQRRLRIA   QILTDNRERI 31           41           51           61           71
Consensus   VEKASEQLWK   KRPDFIAPGG   NAYGQRERAL   CLRDYGWYLR   LITYGILAGD
Conservation *....,.*::   :**..::**    **:*:..:     :***..:*:*   *:***::***
TeAPCα      VDKASQDLWR   RRPDFIAPGG   NAFGQRERAL   CLRDYGWYLR   LITYGLLAGD
MvAPCα      VEEASKKLWK   KRPDFISPGG   NAYGQRERAL   CLRDYGWYLR   LITYGILAGD
OnAPCα      VEEASKKLWK   KRPDFISPGG   NAYGQRERAL   CLRDYGWYLR   LITYGILAGD
CyAPCα      VEKASKQLWQ   KRPDFIAPGG   NAYGDRQRAL   CLRDYGWYMR   LITYGVLAGD
LaAPCα      VDRASGQLWK   KRPDFLAPGG   NAFGQQKKAL   CLRDYGWYLR   LITYGILSGD
LyAPCα      VDRASGQLWK   KRPDFLAPGG   NAFGQQKKSL   CLRDYGWYLR   LITYGILSGD
PyAPCα      VKQGGQQLFQ   KRPDVVSPGG   NAYGEEMTAT   CLRDLDYYLR   LVTYGIVAGD 81           91           101          111          121
Consensus   KEPIESIGLI   GVREMYNSLG   VPVPGMVEAI   RCLKEASLAL   LDEDDAKEAA
Conservation ***.*****:   .*:.:*****   .*:*.*:**:   :*:*....:*   *..:*::*..
TeAPCα      KDPIESIGLI   GVREMYNSLG   VPVPGMVESI   RCLKEASLSL   LDEEDAKETA
MvAPCα      KEPIESIGLI   GVREMYNSLG   VPVPGMVEAI   RCLKEASLAL   LNQEDAKEAA
OnAPCα      KEPIESIGLI   GVREMYNSLG   VPVPGMVEAI   RCLKEASLAL   LNQDDAKEAA
CyAPCα      KEPIESIGLV   GVREMYNSLG   VPVPGMVEAI   RCLKEASLAL   LSEDDALETA
LaAPCα      KDPIESIGLI   GVKEMYNSLG   VPMPGMVEAI   RCLKDASLAL   LDEDDAREAG
LyAPCα      KDPIESIGLI   GVKEMYNSLG   VPMPGMVEAI   RCLKDASLAL   LDEDDAREAA
PyAPCα      VTPIEEIGLV   GVKEMYNSLG   TPISGYAEGV   KCMKSVACSL   LAGEDSAEAG 131
Consensus   PYFDYIIQAM   S         Sequence Identity Relative TeAPCα
Conservation ***:..*.**   .         Full-length    Minus 1st 29 aa
TeAPCα      PYFDYIIQAM   S
MvAPCα      PYFDYIAQAM   S           68.3%           83.3%
OnAPCα      PYFDYIAQAM   S           68.3%           83.3%
CyAPCα      PYFDYIIQAM   S           67.7%           82.6%
LaAPCα      PYFDFIIQAM   S           67.1%           81.8%
LyAPCα      PYFDFIIQAM   S           66.5%           81.1%
PyAPCα      FYFDYTLGAM   Q           41.0%           50.0%
```

FIG. 7A

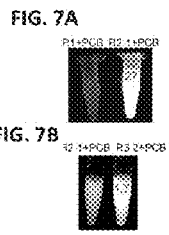

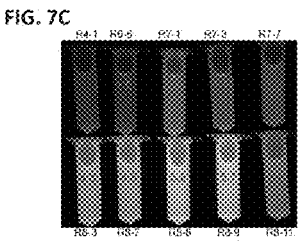

FIG. 7D

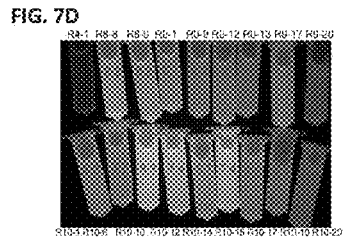

FIG. 7E

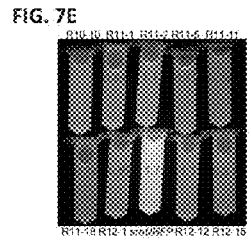

FIG. 7F

|  | 1 | 11 | 21 | 31 | 41 |
|---|---|---|---|---|---|
| Consensus | MKTCEQRVKI | ATLLSENEKK | IVDKASQDLW | RRRPDFIAPG | GIAFSQRERA |
| Conservation | * * * * * * * ; * | * * * * ; * * * * | * * * * * * * * * * | * * ; * * ; * * * * | * * * , * ; * * |
| Charge variation |  |  |  |  |  |
| TeAPCα | MKTGEQRVKI | ATLLSENEKK | IVDKASQDLW | RRRPDFIAPG | GNAFGQRERA |
| R1+PCB | MKTGEQRVKI | ATLLSENEKK | IVDKASQDLW | RRRPDFIAPG | GIAFGQRERA |
| R2-1+PCB | MKTGFQRVKI | ATLLSENEKK | IVDKASQDLW | RRRPDFIAPG | GIAFGQRERA |
| R3-2+PCB | MKTGEQRVKI | ATLLSENEKK | IVDKASQDLW | RRRPDFIAPG | GIAFGQRERA |
| R4-1 | MKTGEQRVKI | ATLLSENEKK | IVDKASQDLW | RRRPDFIAPG | GIAFSQRERA |
| R5-2 | MKTEQRVKI | ATLLSENEKK | IVDKASQDLW | RRRPDFIAPG | GIAFQRERA |
| R6-6 | MKTEQRVKI | ATLLSENEKK | IVDKASQDLW | RRRPDIAPG | GIAFQRERA |
| R7-7 | MKTEQRVKI | ATLLSENEKK | IVDKASQDLW | RRPDIAPG | GIAFQRERA |
| R8-8 | MKTEQRVKI | ATLLSENKK | IVDKASQDLW | RRPDIAPG | GIAFQRRA |
| R8-9 | MKTEQRVI | ATLLSENKK | IVDKASQDLW | RRRPDIAPG | GIAFQRRA |
| R10-10 | MKTEQRVI | ATLLENKK | IVDKASQDLW | RRPDIAPG | GIAFQRRA |
| R11-2 | MKTEQRVI | ATLLENKK | IVDKASQDLW | RRPDIAPG | GIAFQRRA |
| smURFP | MKTSEQRVI | ATLLENKK | IVDKASQDLW | RRPDIAPG | GIAFQRRA |

|  | 51 | 61 | 71 | 81 | 91 |
|---|---|---|---|---|---|
| Consensus | LCLRDYGWYL | RLITPCLLAG | DKGPIESIGL | IGIREMYNSL | GVPVPGMMES |
| Conservation | * * * * * ; * | ; * * * ; * * * * | * * * * * * * * | * ; * * * * * * * | * * * * * * * * * * |
| Charge variation |  |  |  |  |  |
| TeAPCα | LCLRDYGWYL | RLITYGLLAG | DKDPIESIGL | IGVREMYNSL | GVPVPGMVES |
| R1+PCB | LCLRDYGWYL | RLITYGLLAG | DKDPIESIGL | IGVREMYNSL | GVPVPGMVES |
| R2-1+PCB | LCLRDYGWYL | RLITCLLAG | DKDPIESIGL | IGVREMYNSL | GVPVPGMVES |
| R3-2+PCB | LCLRDYGWYL | RLITCLLAG | DKDPIESIGL | IGIREMYNSL | GVPVPGMMES |
| R4-1 | LCLRDYWYL | LITCLLAG | DKDPIESIGL | IGIREMYNSL | GVPVPGMES |
| R5-2 | LCLRDWYL | LITCLLAG | DKDPIESIGL | IGIREMYNSL | GVPYPGMES |
| R6-6 | LCLRDYGWYL | LITCLLAG | DKPIESIGL | IGIREMYNSL | GVPVPGMES |
| R7-7 | LCLRDYGWYL | LITCLLAG | DKPIESIGL | IGIREMYNSL | GVPVPGMES |
| R8-8 | LCLRDYGWYL | LITCLLAG | DKPIESIGL | IGIREMYNSL | GVPVPMES |
| R8-9 | LCLRDYGWYL | LITCLLAG | DKPIESIGL | IGIREMYNSL | GVPVPDMES |
| R10-10 | LCLRDYGWYL | LITCLLAG | DKPIESIGL | IGIREMYNSL | GVPVPMES |
| R11-2 | LCLRDYGWYL | LITCLLAG | DKPIESIGL | IREMYNSL | GVPVPMES |
| smURFP | LCLRDYGWL | LITCLLAG | DKGPIESIGL | IREMYNSL | GVPYPMES |

|  | 101 | 111 | 121 | 131 |
|---|---|---|---|---|
| Consensus | IRCLKEASLS | LLDEEDAKET | APYFDYIIKA | MS |
| Conservation | * * * * * * * * | * * ; * * * * ; * * | * * * * * * * ; * | ; * |
| Charge variation |  |  |  |  |
| TeAPCα | IRCLKEASLS | LLDEEDAKET | APYFDYIIQA | MS |
| R1+PCB | IRCLKEASLS | LLDEEDAKET | APYFDYIIQA | MS |
| R2-1+PCB | IRCLKEASLS | LLDEEDAKET | APYFDYIIQA | MS |
| R3-2+PCB | IRCLKEASLS | LLDEEDAKET | APYFDYIIQA | MS |
| R4-1 | IRCLKEASLS | LLDEEDAKET | APYFDYIIA | MS |
| R5-2 | IRCLKEASLS | LLDEEDAKET | APYFDYIIA | MS |
| R6-6 | IRCLKEASLS | LLDEEDAKET | APYFDYIIA | MS |
| R7-7 | IRCLKEASLS | LLDEEDAKET | APYFDYIIA | IS |
| R8-8 | IRCLKEASLS | LLDEEDAKET | APYFDYIIA | MS |
| R8-9 | IRCLKEASLS | LLDEEDAKET | APYFDYIIA | MS |
| R10-10 | IRCLKEASLS | LLDEEDAET | APYFDYIIA | MS |
| R11-2 | IRCLKEASLS | LLEEEDAET | APYFDYIIA | MS |
| smURFP | IRCLKEASLS | LLDEEDAET | APYFDYIIA | MS |

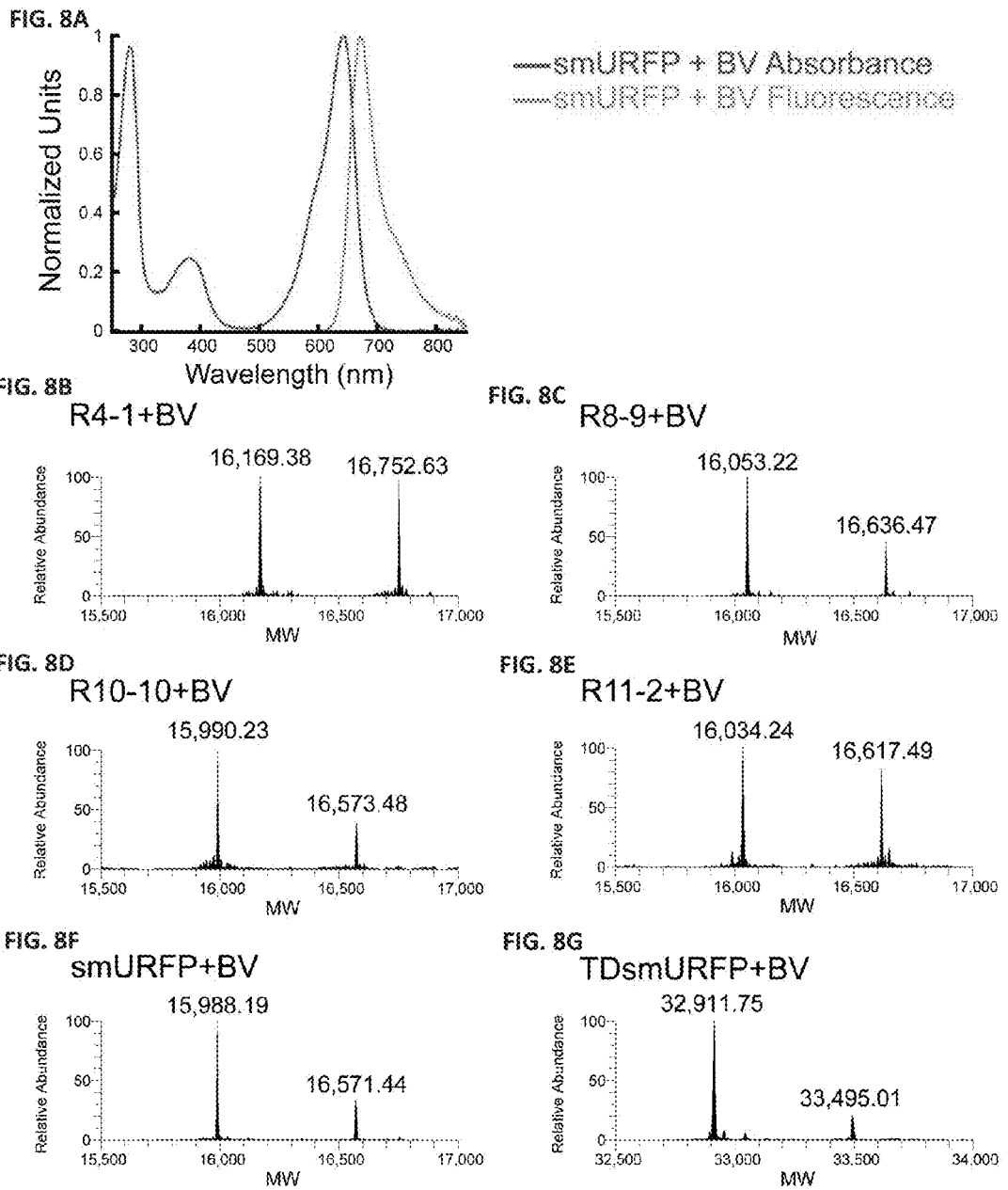

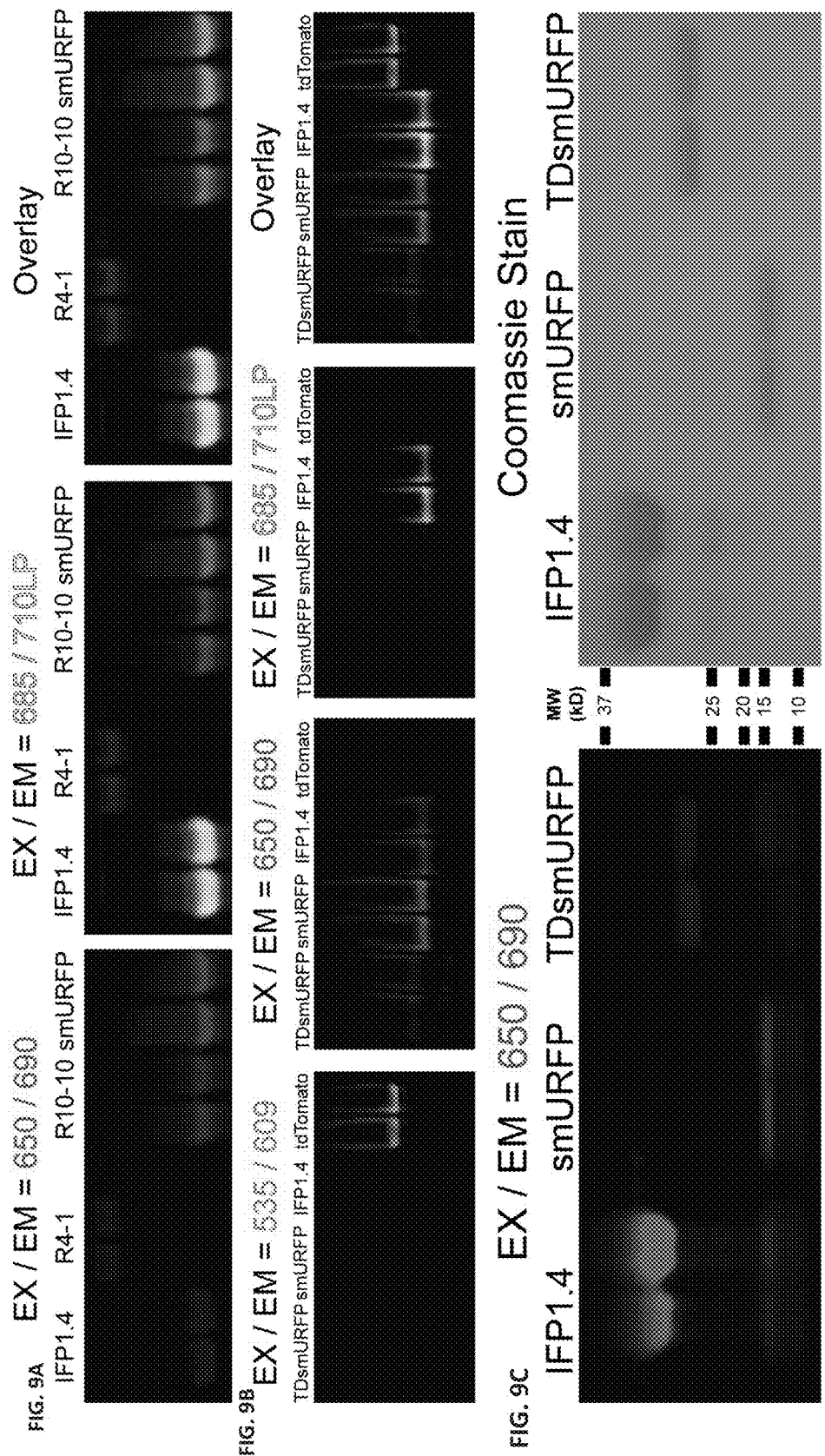

FIG. 10A
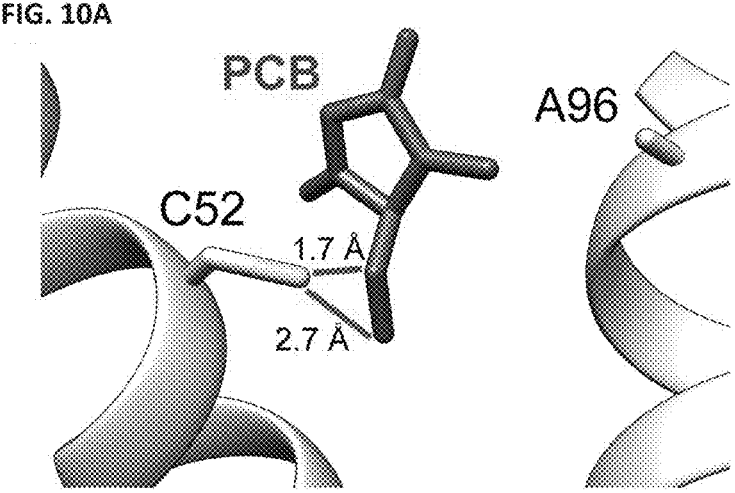
FIG. 10B
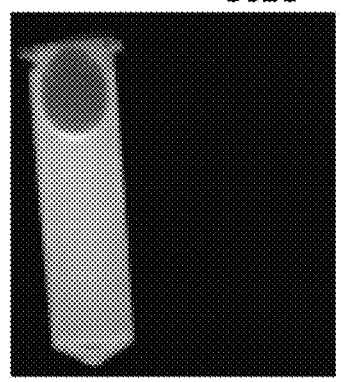
FIG. 10C
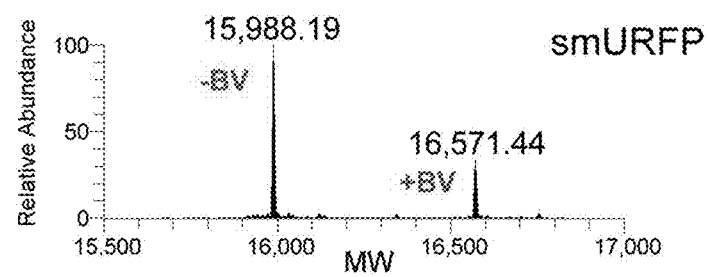
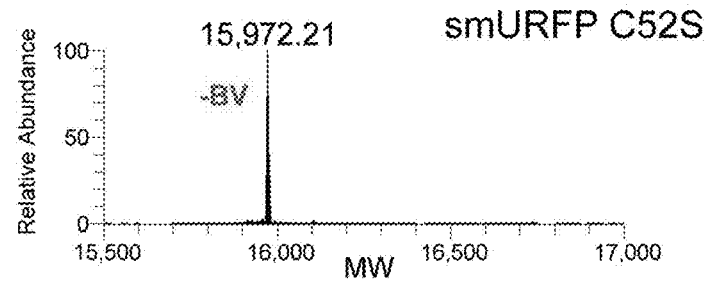

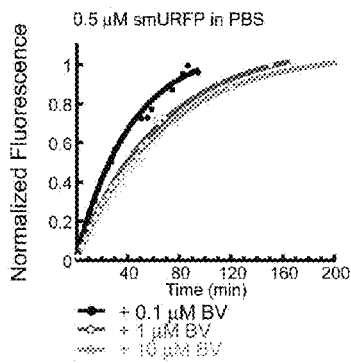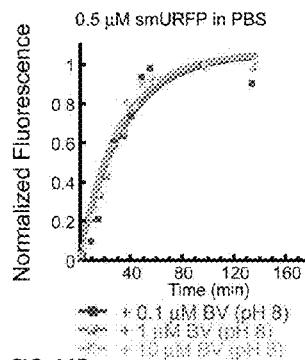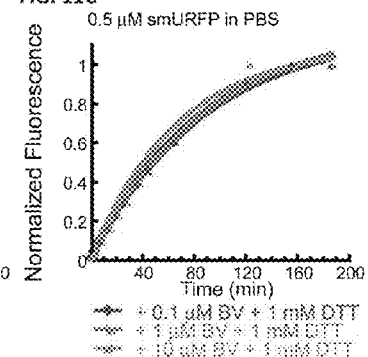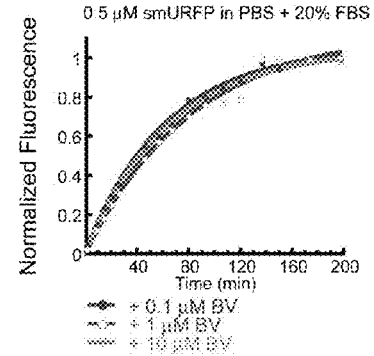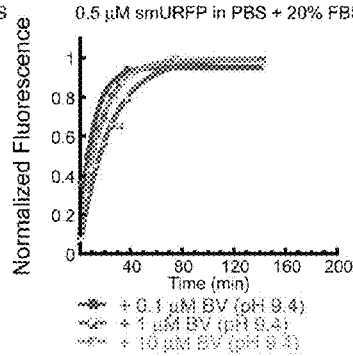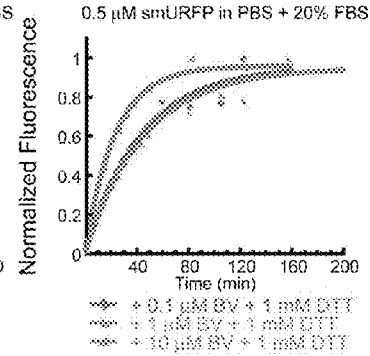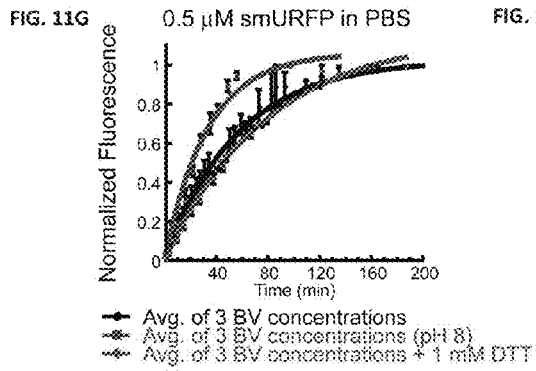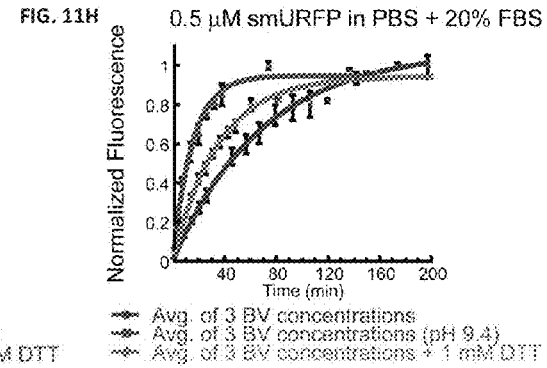

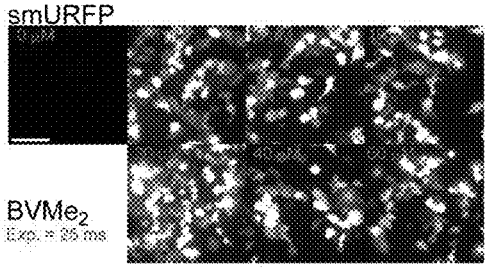
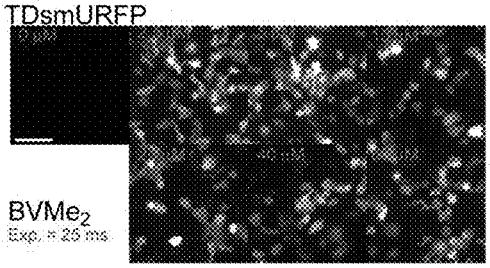
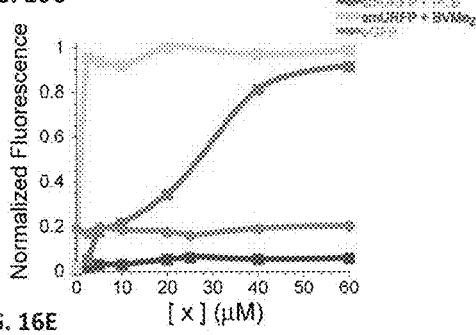
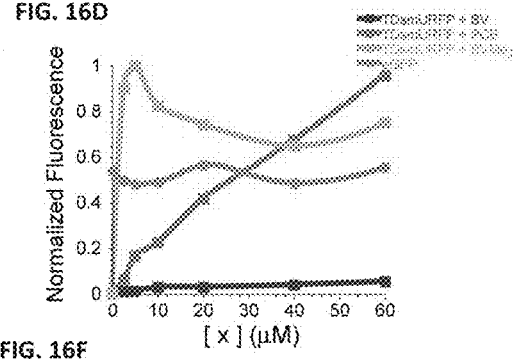
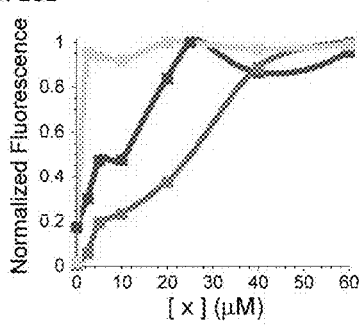
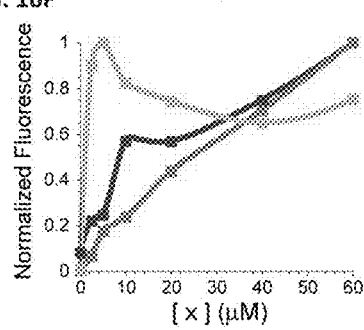

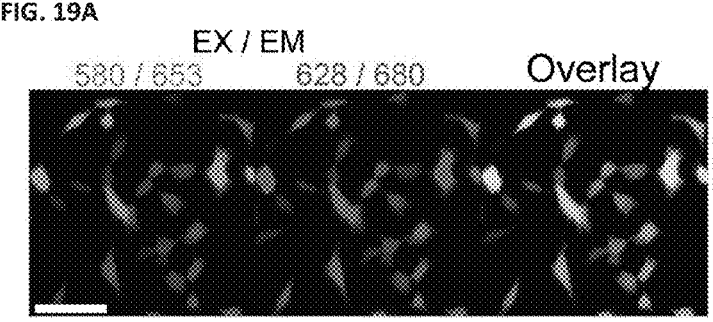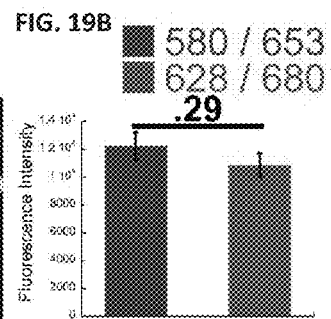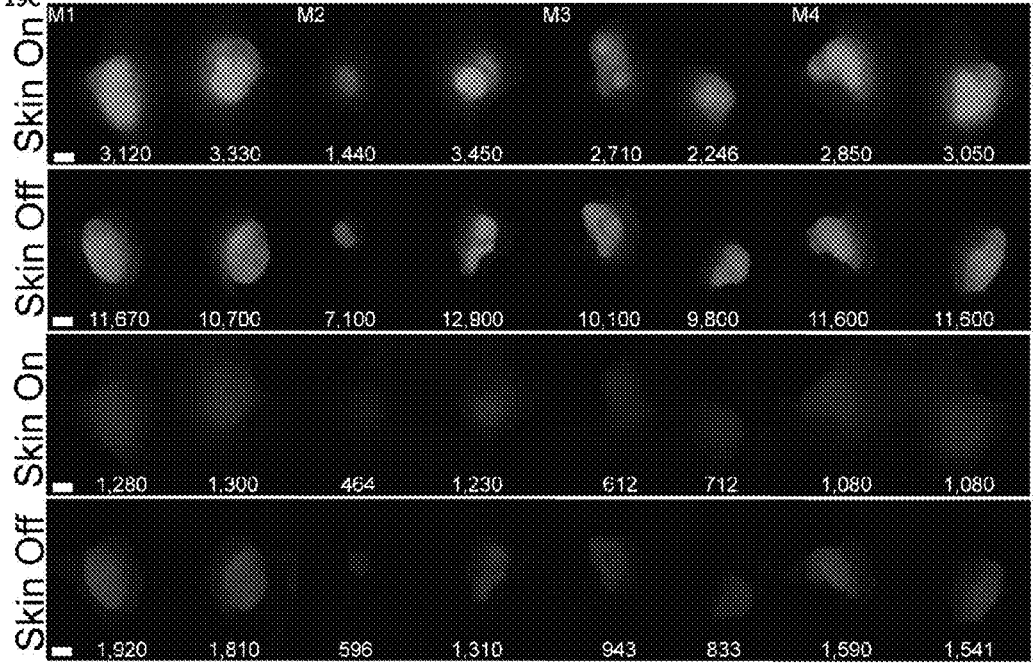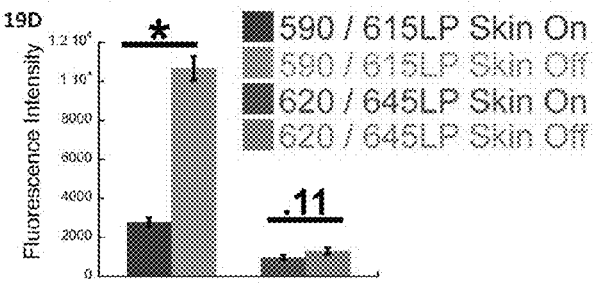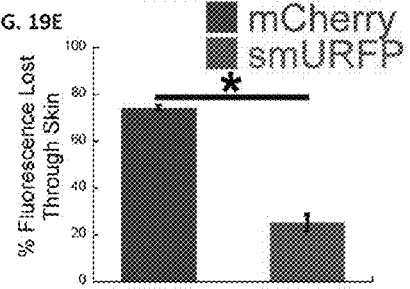

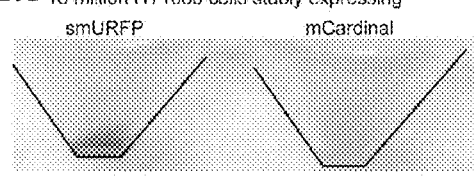
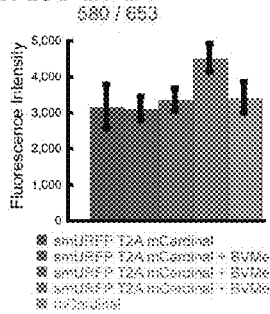
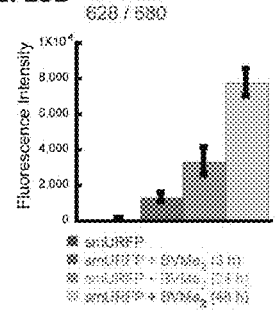
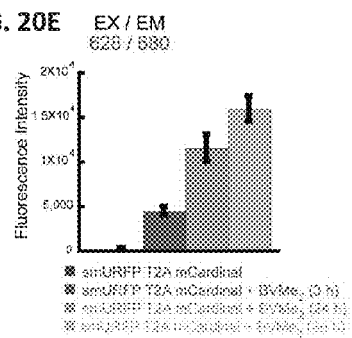
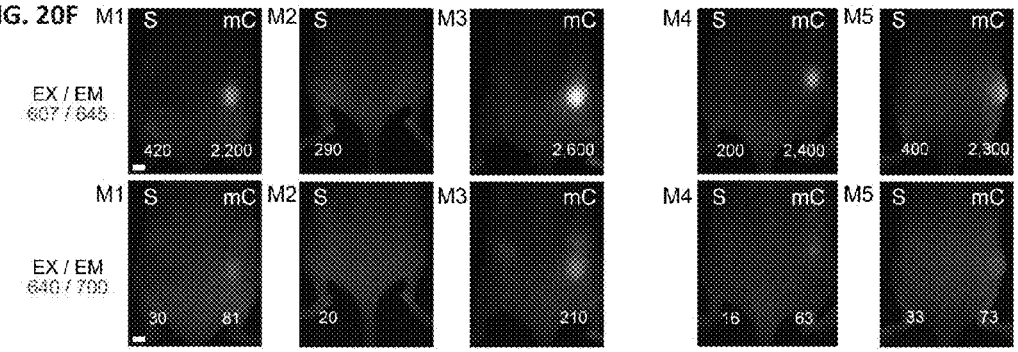
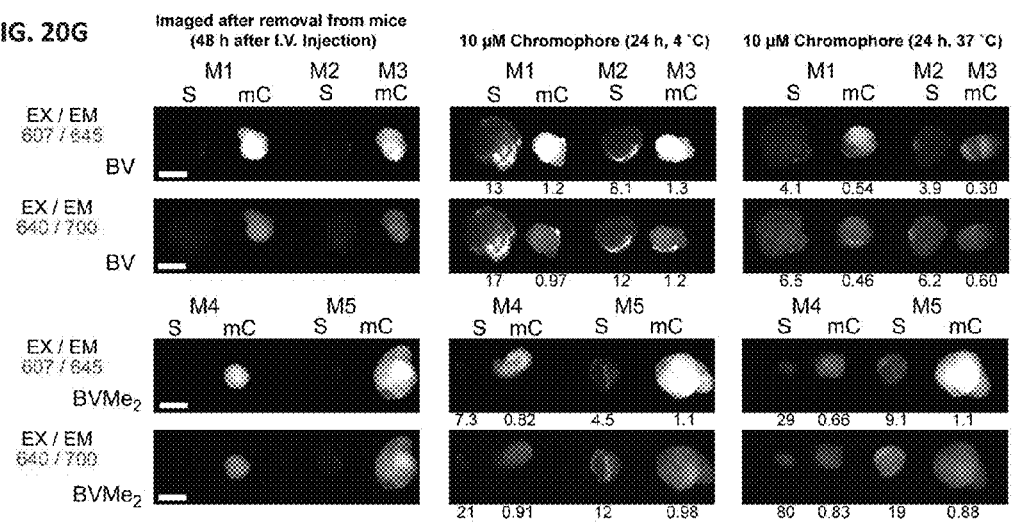

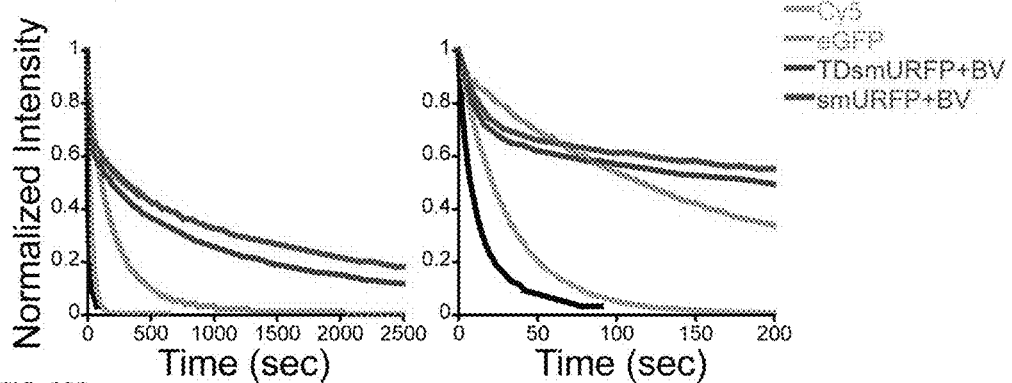
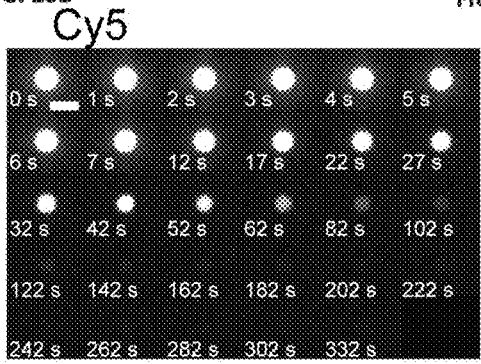
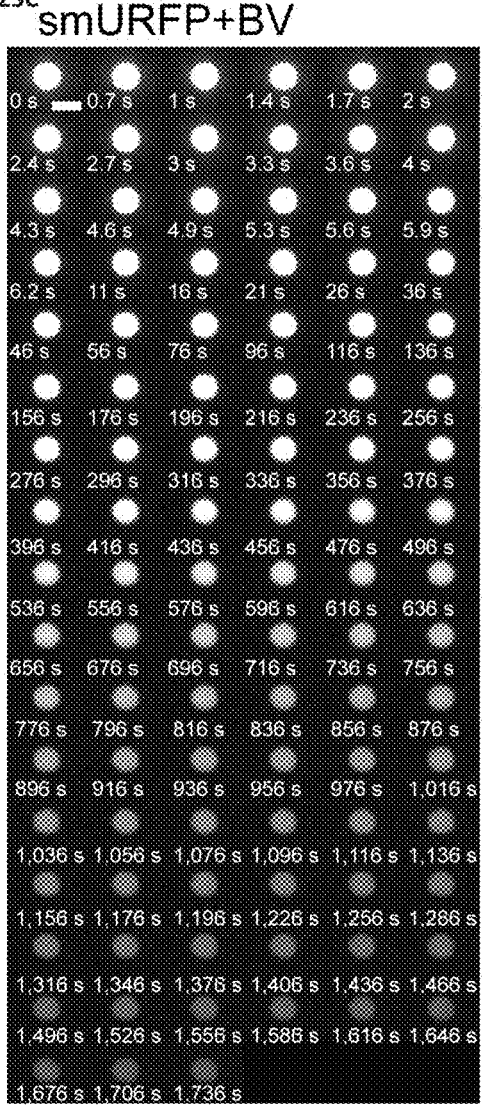

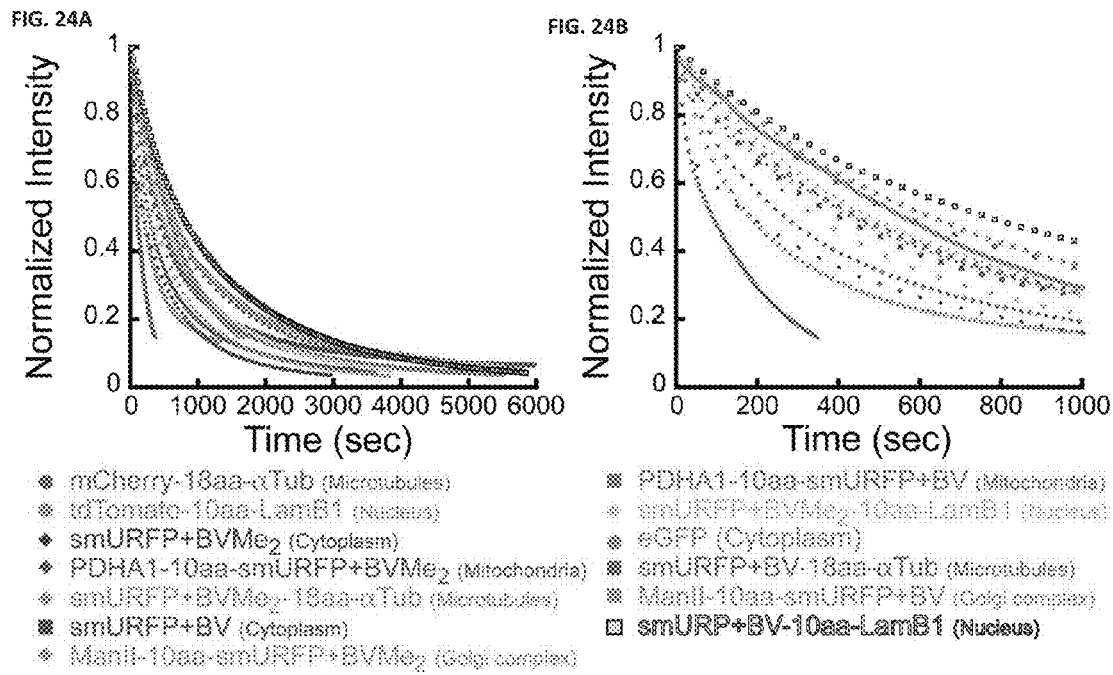

SEQUENCE LISTING

<160> NUMBER OF SEQ ID NOS: 41

<210> SEQ ID NO 1
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 1

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Asn Ala Phe Gly Gln Arg Glu
        35                  40                  45

Arg Ala Leu Cys Leu Arg Asp Tyr Gly Trp Tyr Leu Arg Leu Ile Thr
    50                  55                  60

Tyr Gly Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
    130

<210> SEQ ID NO 2
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 2

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Gly Gln Arg Glu
        35                  40                  45

Arg Ala Leu Cys Leu Arg Asp Tyr Gly Trp Tyr Leu Arg Leu Ile Thr

Tyr Gly Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
    130

<210> SEQ ID NO 3
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 3

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Gly Gln Arg Glu
        35                  40                  45

Arg Ala Leu Cys Leu Arg Asp Tyr Gly Trp Tyr Leu Arg Leu Ile Thr
    50                  55                  60

Phe Cys Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
    130

<210> SEQ ID NO 4
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 4

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Gly Gln Arg Glu
        35                  40                  45

Arg Ala Leu Cys Leu Arg Asp Tyr Gly Trp Tyr Leu Arg Leu Ile Thr
    50                  55                  60

Phe Cys Leu Leu Ala Gly Asp Lys Asp Pro Ile Glu Ser Ile Gly Leu
65                  70                  75                  80

-continued

```
Ile Gly Ile Arg Glu Met Tyr Asn Ser Leu Gly Val Pro Val Pro Gly
                85                  90                  95
Met Met Glu Ser Ile Arg Cys Leu Lys Glu Ala Ser Leu Ser Leu Leu
            100                 105                 110
Asp Glu Glu Asp Ala Lys Glu Thr Ala Pro Tyr Phe Asp Tyr Ile Ile
        115                 120                 125
Gln Ala Met Ser
        130

<210> SEQ ID NO 5
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 5

Met Lys Thr Gly Glu Gln Arg Val Lys Ile Ala Thr Leu Leu Ser Glu
1               5                   10                  15
Asn Glu Lys Lys Ile Val Asp Lys Ala Ser Gln Asp Leu Trp Arg Arg
            20                  25                  30
Arg Pro Asp Phe Ile Ala Pro Gly Gly Ile Ala Phe Ser Gln Arg Glu
        35                  40                  45
Arg Ala Leu Cys Leu Arg Asp Tyr Arg Trp Tyr Leu His Leu Ile Thr
    50                  55                  60
Phe Cys Leu Leu Ala Gly Asp Lys Asp Pro Ile Glu Ser Ile Gly Leu
65                  70                  75                  80
Ile Gly Ile Arg Glu Met Tyr Asn Ser Leu Gly Val Pro Val Pro Gly
                85                  90                  95
Met Met Glu Ser Ile Arg Cys Leu Lys Glu Ala Ser Leu Ser Leu Leu
            100                 105                 110
Asp Glu Glu Asp Ala Lys Glu Thr Ala Pro Tyr Phe Asp Tyr Ile Ile
        115                 120                 125
Lys Ala Met Ser
        130

<210> SEQ ID NO 6
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 6

Met Lys Thr Cys Glu Gln Arg Val Lys Ile Ala Thr Leu Leu Ser Glu
1               5                   10                  15
Asn Glu Lys Lys Ile Val Asp Lys Ala Ser Gln Asp Leu Trp Arg Arg
            20                  25                  30
Arg Pro Asp Phe Ile Ala Pro Gly Gly Ile Ala Phe Ser Gln Arg Glu
        35                  40                  45
Arg Ala Leu Cys Leu Arg Asp His Arg Trp Tyr Leu His Leu Ile Thr
    50                  55                  60
Phe Cys Leu Leu Ala Gly Asp Lys Asp Pro Ile Glu Ser Ile Gly Leu
65                  70                  75                  80
Ile Gly Ile Arg Glu Met Tyr Asn Ser Leu Gly Val Pro Val Pro Gly
                85                  90                  95
Met Met Glu Ser Ile Arg Cys Leu Lys Glu Ala Ser Leu Ser Leu Leu
            100                 105                 110
```

```
Asp Glu Glu Asp Ala Lys Glu Thr Ala Pro Tyr Phe Asp Tyr Ile Ile
        115                 120                 125

Lys Ala Met Ser
    130

<210> SEQ ID NO 7
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 7

Met Lys Thr Cys Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Glu
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Met Ser
    130

<210> SEQ ID NO 8
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 8

Met Lys Thr Cys Glu Gln Arg Val Lys Ile Ala Thr Leu Leu Ser Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Glu
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Ile Ser
```

<210> SEQ ID NO 9
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 9

```
Met Lys Thr Cys Glu Gln Arg Val Lys Ile Ala Thr Leu Leu Ser Glu
1               5                   10                  15

Asn Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
            35                  40                  45

Arg Ala Leu Cys Leu Arg Asp Tyr Gly Trp Tyr Leu His Leu Ile Thr
        50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Asp Glu Glu Asp Ala Asn Glu Thr Ala Pro Tyr Phe Asp Tyr Ile Ile
        115                 120                 125

Lys Ala Met Ser
    130
```

<210> SEQ ID NO 10
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 10

```
Met Lys Thr Cys Glu Gln Arg Val Asn Ile Ala Thr Leu Leu Ser Glu
1               5                   10                  15

Asn Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Asp
            35                  40                  45

Arg Ala Leu Cys Leu Arg Asp Tyr Gly Trp Tyr Leu His Leu Ile Thr
        50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Asp
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Met Ser
    130
```

<210> SEQ ID NO 11
<211> LENGTH: 132

```
<212> TYPE: PRT
<213> ORGANISM: Artificial Sequence
<220> FEATURE:
<223> OTHER INFORMATION: smRUFP Variant Polypeptide

<400> SEQUENCE: 11

Met Lys Thr Cys Glu Gln Arg Val Asn Ile Ala Thr Leu Leu Thr Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Asp Glu Glu Asp Ala Asn Glu Thr Ala Pro Tyr Phe Asp Tyr Ile Ile
        115                 120                 125

Lys Ala Met Ser
    130

<210> SEQ ID NO 12
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 12

Met Lys Thr Cys Glu Gln Arg Val Asn Ile Ala Thr Leu Leu Thr Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Ser Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Glu Glu Glu Asp Ala Asn Glu Thr Ala Pro Tyr Phe Asp Tyr Ile Ile
        115                 120                 125

Lys Ala Met Ser
    130

<210> SEQ ID NO 13
<211> LENGTH: 132
<212> TYPE: PRT
<213> ORGANISM: Artificial Sequence
<220> FEATURE:
<223> OTHER INFORMATION: smRUFP Variant Polypeptide
```

<400> SEQUENCE: 13

Met Lys Thr Ser Glu Gln Arg Val Asn Ile Ala Thr Leu Leu Thr Glu
1               5                   10                  15

Asn Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
            35                  40                  45

Arg Ala Leu Cys Leu Arg Asp Tyr Gly Trp Phe Leu His Leu Ile Thr
    50                  55                  60

Phe Cys Leu Leu Ala Gly Asp Lys Gly Pro Ile Glu Ser Ile Gly Leu
65                  70                  75                  80

Ile Ser Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Asp Glu Glu Asp Ala Asn Glu Thr Ala Pro Tyr Phe Asp Tyr Ile Ile
            115                 120                 125

Lys Ala Met Ser
    130

<210> SEQ ID NO 14
<211> LENGTH: 132
<212> TYPE: PRT
<213> ORGANISM: Artificial Sequence
<220> FEATURE:
<223> OTHER INFORMATION: smRUFP Variant Polypeptide

<400> SEQUENCE: 14

Met Lys Thr Cys Glu Gln Arg Val Lys Ile Ala Thr Leu Leu Ser Glu
1               5                   10                  15

Asn Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Glu
            35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
            115                 120                 125

Lys Ala Met Ser
    130

<210> SEQ ID NO 15
<211> LENGTH: 23
<212> TYPE: PRT
<213> ORGANISM: Artificial Sequence
<220> FEATURE:
<223> OTHER INFORMATION: Linker

<400> SEQUENCE: 15

Gly His Gly Thr Gly Ser Thr Gly Ser Gly Ser Ser Gly Thr Ala Ser
1               5                   10                  15

-continued

Ser Glu Asp Asn Asn Met Ala
            20

<210> SEQ ID NO 16
<211> LENGTH: 5
<212> TYPE: PRT
<213> ORGANISM: Artificial Sequence
<220> FEATURE:
<223> OTHER INFORMATION: Linker

<400> SEQUENCE: 16

Gly Gly Gly Gly Ser
1               5

<210> SEQ ID NO 17
<211> LENGTH: 10
<212> TYPE: PRT
<213> ORGANISM: Artificial Sequence
<220> FEATURE:
<223> OTHER INFORMATION: Linker

<400> SEQUENCE: 17

Gly Gly Gly Gly Ser Gly Gly Gly Gly Ser
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Linker

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Linker

<400> SEQUENCE: 19

Gly Gly Gly Gly Ser Gly Gly Gly Gly Ser Gly Gly Gly Gly Ser
1               5                   10                  15

<210> SEQ ID NO 20
<211> LENGTH: 25
<212> TYPE: PRT
<213> ORGANISM: Artificial Sequence
<220> FEATURE:
<223> OTHER INFORMATION: Linker

<400> SEQUENCE: 20

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 21
<211> LENGTH: 161
<212> TYPE: PRT
<213> ORGANISM: Artificial Sequence
<220> FEATURE:
<223> OTHER INFORMATION: Fluorescent Protein -continued

```
<400> SEQUENCE: 21

Met Ser Val Val Ser Gln Leu Ile Leu Gln Ala Asp Asp Glu Leu Arg
1               5                   10                  15

Tyr Pro Ser Thr Gly Glu Leu Gln Ser Ile Lys Asp Phe Leu Lys Thr
            20                  25                  30

Gly Glu Gln Arg Val Arg Ile Ala Thr Ala Leu Ser Asp Ser Glu Arg
        35                  40                  45

Lys Ile Val Glu Glu Ala Ser Lys Lys Leu Trp Lys Lys Arg Pro Asp
    50                  55                  60

Phe Ile Ser Pro Gly Gly Asn Ala Tyr Gly Gln Arg Glu Arg Ala Leu
65                  70                  75                  80

Cys Leu Arg Asp Tyr Gly Trp Tyr Leu Arg Leu Ile Thr Tyr Gly Ile
                85                  90                  95

Leu Ala Gly Asp Lys Glu Pro Ile Glu Ser Ile Gly Leu Ile Gly Val
            100                 105                 110

Arg Glu Met Tyr Asn Ser Leu Gly Val Pro Val Pro Gly Met Val Glu
        115                 120                 125

Ala Ile Arg Cys Leu Lys Glu Ala Ser Leu Ala Leu Leu Asn Gln Glu
    130                 135                 140

Asp Ala Lys Glu Ala Ala Pro Tyr Phe Asp Tyr Ile Ala Gln Ala Met
145                 150                 155                 160

Ser

<210> SEQ ID NO 22
<211> LENGTH: 161
<212> TYPE: PRT
<213> ORGANISM: Artificial Sequence
<220> FEATURE:
<223> OTHER INFORMATION: Fluorescent Protein

<400> SEQUENCE: 22

Met Ser Val Val Ser Gln Leu Ile Leu Gln Ala Asp Asp Glu Leu Arg
1               5                   10                  15

Tyr Pro Ser Thr Gly Glu Leu Gln Ser Ile Asn Asp Phe Phe Lys Thr
            20                  25                  30

Gly Glu Gln Arg Val Arg Ile Ala Thr Ala Leu Ser Asp Ser Glu Lys
        35                  40                  45

Lys Ile Val Glu Glu Ala Ser Lys Lys Leu Trp Lys Lys Arg Pro Asp
    50                  55                  60

Phe Ile Ser Pro Gly Gly Asn Ala Tyr Gly Gln Arg Glu Arg Ala Leu
65                  70                  75                  80

Cys Leu Arg Asp Tyr Gly Trp Tyr Leu Arg Leu Ile Thr Tyr Gly Ile
                85                  90                  95

Leu Ala Gly Asp Lys Glu Pro Ile Glu Ser Ile Gly Leu Ile Gly Val
            100                 105                 110

Arg Glu Met Tyr Asn Ser Leu Gly Val Pro Val Pro Gly Met Val Glu
        115                 120                 125

Ala Ile Arg Cys Leu Lys Glu Ala Ser Leu Ala Leu Leu Asn Gln Asp
    130                 135                 140

Asp Ala Lys Glu Ala Ala Pro Tyr Phe Asp Tyr Ile Ala Gln Ala Met
145                 150                 155                 160

Ser

<210> SEQ ID NO 23
<211> LENGTH: 161
```

<212> TYPE: PRT
<213> ORGANISM: Artificial Sequence
<220> FEATURE:
<223> OTHER INFORMATION: Fluorescent Protein

<400> SEQUENCE: 23

Met Ser Val Val Ser Gln Val Leu Leu Gln Ala Asp Asp Glu Leu Arg
1               5                   10                  15

Tyr Pro Ser Ala Gly Glu Leu Lys Ser Leu Gln Asp Phe Phe Gln Thr
            20                  25                  30

Gly Glu Gln Arg Met Arg Ile Ala Thr Thr Leu Ser Glu Asn Glu Lys
        35                  40                  45

Arg Ile Val Glu Lys Ala Ser Lys Gln Leu Trp Gln Lys Arg Pro Asp
50                  55                  60

Phe Ile Ala Pro Gly Gly Asn Ala Tyr Gly Asp Arg Gln Arg Ala Leu
65                  70                  75                  80

Cys Leu Arg Asp Tyr Gly Trp Tyr Met Arg Leu Ile Thr Tyr Gly Val
                85                  90                  95

Leu Ala Gly Asp Lys Glu Pro Ile Glu Ser Ile Gly Leu Val Gly Val
            100                 105                 110

Arg Glu Met Tyr Asn Ser Leu Gly Val Pro Val Pro Gly Met Val Glu
        115                 120                 125

Ala Ile Arg Cys Leu Lys Glu Ala Ser Leu Ala Leu Leu Ser Glu Asp
130                 135                 140

Asp Ala Leu Glu Thr Ala Pro Tyr Phe Asp Tyr Ile Ile Gln Ala Met
145                 150                 155                 160

Ser

<210> SEQ ID NO 24
<211> LENGTH: 161
<212> TYPE: PRT
<213> ORGANISM: Artificial Sequence
<220> FEATURE:
<223> OTHER INFORMATION: Fluorescent Protein

<400> SEQUENCE: 24

Met Thr Val Val Ser Gln Val Ile Leu Lys Ala Asp Asp Glu Leu Arg
1               5                   10                  15

Tyr Pro Ser Thr Gly Glu Leu Gln Asn Ile Ser Asp Phe Leu Lys Thr
            20                  25                  30

Gly Glu Gln Arg Val Arg Ile Ala Thr Thr Leu Ser Glu Asn Glu Lys
        35                  40                  45

Lys Ile Val Asp Arg Ala Ser Gly Gln Leu Trp Lys Lys Arg Pro Asp
50                  55                  60

Phe Leu Ala Pro Gly Gly Asn Ala Phe Gly Gln Gln Lys Lys Ala Leu
65                  70                  75                  80

Cys Leu Arg Asp Tyr Gly Trp Tyr Leu Arg Leu Ile Thr Tyr Gly Ile
                85                  90                  95

Leu Ser Gly Asp Lys Asp Pro Ile Glu Ser Ile Gly Leu Ile Gly Val
            100                 105                 110

Lys Glu Met Tyr Asn Ser Leu Gly Val Pro Met Pro Gly Met Val Glu
        115                 120                 125

Ala Ile Arg Cys Leu Lys Asp Ala Ser Leu Ala Leu Leu Asp Glu Asp
130                 135                 140

Asp Ala Arg Glu Ala Gly Pro Tyr Phe Asp Phe Ile Ile Gln Ala Met
145                 150                 155                 160

Ser

<210> SEQ ID NO 25
<211> LENGTH: 161
<212> TYPE: PRT
<213> ORGANISM: Artificial Sequence
<220> FEATURE:
<223> OTHER INFORMATION: Fluorescent Protein

<400> SEQUENCE: 25

```
Met Thr Val Val Ser Gln Val Ile Leu Lys Ala Asp Asp Glu Leu Arg
1               5                   10                  15

Tyr Pro Ser Thr Gly Glu Leu Gln Asn Ile Ser Asp Phe Leu Lys Thr
            20                  25                  30

Gly Glu Gln Arg Val Arg Ile Ala Thr Thr Phe Ser Glu Asn Glu Lys
        35                  40                  45

Lys Ile Val Asp Arg Ala Ser Gly Gln Leu Trp Lys Lys Arg Pro Asp
    50                  55                  60

Phe Leu Ala Pro Gly Gly Asn Ala Phe Gly Gln Gln Lys Lys Ser Leu
65                  70                  75                  80

Cys Leu Arg Asp Tyr Gly Trp Tyr Leu Arg Leu Ile Thr Tyr Gly Ile
                85                  90                  95

Leu Ser Gly Asp Lys Asp Pro Ile Glu Ser Ile Gly Leu Ile Gly Val
            100                 105                 110

Lys Glu Met Tyr Asn Ser Leu Gly Val Pro Met Pro Gly Met Val Glu
        115                 120                 125

Ala Ile Arg Cys Leu Lys Asp Ala Ser Leu Ala Leu Leu Asp Glu Asp
    130                 135                 140

Asp Ala Arg Glu Ala Ala Pro Tyr Phe Asp Phe Ile Ile Gln Ala Met
145                 150                 155                 160

Ser
```

<210> SEQ ID NO 26
<211> LENGTH: 161
<212> TYPE: PRT
<213> ORGANISM: Artificial Sequence
<220> FEATURE:
<223> OTHER INFORMATION: Fluorescent Protein

<400> SEQUENCE: 26

```
Met Ser Ile Val Thr Lys Ser Ile Val Asn Ala Asp Ala Glu Ala Arg
1               5                   10                  15

Tyr Leu Ser Pro Gly Glu Leu Asp Arg Ile Lys Ser Phe Val Leu Ser
            20                  25                  30

Gly Gln Arg Arg Leu Arg Ile Ala Gln Ile Leu Thr Asp Asn Arg Glu
        35                  40                  45

Arg Ile Val Lys Gln Gly Gly Gln Leu Phe Gln Lys Arg Pro Asp
    50                  55                  60

Val Val Ser Pro Gly Gly Asn Ala Tyr Gly Glu Met Thr Ala Thr
65                  70                  75                  80

Cys Leu Arg Asp Leu Asp Tyr Tyr Leu Arg Leu Val Thr Tyr Gly Ile
                85                  90                  95

Val Ala Gly Asp Val Thr Pro Ile Glu Glu Ile Gly Leu Val Gly Val
            100                 105                 110

Lys Glu Met Tyr Asn Ser Leu Gly Thr Pro Ile Ser Gly Val Ala Glu
        115                 120                 125

Gly Val Lys Cys Met Lys Ser Val Ala Cys Ser Leu Leu Ala Gly Glu
```

```
                130                 135                 140
Asp Ser Ala Glu Ala Gly Phe Tyr Phe Asp Tyr Thr Leu Gly Ala Met
145                 150                 155                 160

Gln
```

<210> SEQ ID NO 27
<211> LENGTH: 161
<212> TYPE: PRT
<213> ORGANISM: Artificial Sequence
<220> FEATURE:
<223> OTHER INFORMATION: Fluorescent Protein

<400> SEQUENCE: 27

```
Met Ser Thr Val Ser Gln Val Ile Leu Gln Ala Asp Asp Glu Leu Arg
1               5                   10                  15

Tyr Pro Ser Thr Gly Glu Leu Gln Ser Ile Lys Asp Phe Leu Lys Thr
                20                  25                  30

Gly Glu Gln Arg Val Arg Ile Ala Thr Thr Leu Ser Glu Asn Glu Lys
            35                  40                  45

Lys Ile Val Glu Lys Ala Ser Lys Gln Leu Trp Lys Lys Arg Pro Asp
    50                  55                  60

Phe Ile Ala Pro Gly Gly Asn Ala Tyr Gly Gln Arg Glu Arg Ala Leu
65                  70                  75                  80

Cys Leu Arg Asp Tyr Gly Trp Tyr Leu Arg Leu Ile Thr Tyr Gly Ile
                85                  90                  95

Leu Ala Gly Asp Lys Glu Pro Ile Glu Ser Ile Gly Leu Ile Gly Val
            100                 105                 110

Arg Glu Met Tyr Asn Ser Leu Gly Val Pro Val Pro Gly Met Val Glu
        115                 120                 125

Ala Ile Arg Cys Leu Lys Glu Ala Ser Leu Ala Leu Leu Asp Glu Asp
    130                 135                 140

Asp Ala Lys Glu Ala Ala Pro Tyr Phe Asp Tyr Ile Ile Gln Ala Met
145                 150                 155                 160

Ser
```

<210> SEQ ID NO 28
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 28

```
Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
                20                  25                  30

Arg Pro Asp Phe Ile Ala Pro Gly Gly Asn Ala Phe Gly Gln Arg Glu
            35                  40                  45

Arg Ala Leu Cys Leu Arg Asp Tyr Gly Trp Tyr Leu Arg Leu Ile Thr
    50                  55                  60

Tyr Gly Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110
```

```
Asp Glu Glu Asp Ala Lys Glu Thr Ala Pro Tyr Phe Asp Tyr Ile Ile
        115                 120                 125

Gln Ala Met Ser
    130

<210> SEQ ID NO 29
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 29

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Gly Gln Arg Glu
        35                  40                  45

Arg Ala Leu Cys Leu Arg Asp Tyr Gly Trp Tyr Leu Arg Leu Ile Thr
    50                  55                  60

Tyr Gly Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
    130

<210> SEQ ID NO 30
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 30

Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Gly Gln Arg Glu
        35                  40                  45

Arg Ala Leu Cys Leu Arg Asp Tyr Gly Trp Tyr Leu Arg Leu Ile Thr
    50                  55                  60

Phe Cys Leu Leu Ala Gly Asp Lys Asp Pro Ile Glu Ser Ile Gly Leu
65                  70                  75                  80

Ile Gly Val Arg Glu Met Tyr Asn Ser Leu Gly Val Pro Val Pro Gly
                85                  90                  95

Met Val Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
```

<210> SEQ ID NO 31
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 31

```
Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
                20                  25                  30

Arg Pro Asp Phe Ile Ala Pro Gly Gly Ile Ala Phe Gly Gln Arg Glu
            35                  40                  45

Arg Ala Leu Cys Leu Arg Asp Tyr Gly Trp Tyr Leu Arg Leu Ile Thr
        50                  55                  60

Phe Cys Leu Leu Ala Gly Asp Lys Asp Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Gln Ala Met Ser
    130
```

<210> SEQ ID NO 32
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 32

```
Met Lys Thr Gly Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
                20                  25                  30

Arg Pro Asp Phe Ile Ala Pro Gly Gly Ile Ala Phe Ser Gln Arg Glu
            35                  40                  45

Arg Ala Leu Cys Leu Arg Asp Tyr Arg Trp Tyr Leu His Leu Ile Thr
        50                  55                  60

Phe Cys Leu Leu Ala Gly Asp Lys Asp Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Met Ser
    130
```

<210> SEQ ID NO 33
<211> LENGTH: 132

```
<212> TYPE: PRT
<213> ORGANISM: Artificial Sequence
<220> FEATURE:
<223> OTHER INFORMATION: Fluorescent Protein

<400> SEQUENCE: 33

Met Lys Thr Cys Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Phe Ile Ala Pro Gly Gly Ile Ala Phe Ser Gln Arg Glu
        35                  40                  45

Arg Ala Leu Cys Leu Arg Asp His Arg Trp Tyr Leu His Leu Ile Thr
    50                  55                  60

Phe Cys Leu Leu Ala Gly Asp Lys Asp Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Met Ser
    130

<210> SEQ ID NO 34
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 34

Met Lys Thr Cys Glu Gln Arg Val Lys Ile Ala Thr Leu Leu Ser Glu
1               5                   10                  15

Asn Glu Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Glu
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Met Ser
    130

<210> SEQ ID NO 35
<211> LENGTH: 132
<212> TYPE: PRT
<213> ORGANISM: Artificial Sequence
<220> FEATURE:
<223> OTHER INFORMATION: Fluorescent Protein
```

```
<400> SEQUENCE: 35

Met Lys Thr Cys Glu Gln Arg Val Lys Ile Ala Thr Leu Leu Ser Glu
1               5                   10                  15

Asn Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Glu
        35                  40                  45

Arg Ala Leu Cys Leu Arg Asp Tyr Gly Trp Tyr Leu His Leu Ile Thr
    50                  55                      60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
            100                 105                 110

Asp Glu Glu Asp Ala Lys Glu Thr Ala Pro Tyr Phe Asp Tyr Ile Ile
        115                 120                 125

Lys Ala Ile Ser
    130

<210> SEQ ID NO 36
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 36

Met Lys Thr Cys Glu Gln Arg Val Lys Ile Ala Thr Leu Leu Ser Glu
1               5                   10                  15

Asn Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

Arg Ala Leu Cys Leu Arg Asp Tyr Gly Trp Tyr Leu His Leu Ile Thr
    50                  55                      60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Asp Glu Glu Asp Ala Asn Glu Thr Ala Pro Tyr Phe Asp Tyr Ile Ile
        115                 120                 125

Lys Ala Met Ser
    130

<210> SEQ ID NO 37
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 37

Met Lys Thr Cys Glu Gln Arg Val Asn Ile Ala Thr Leu Leu Ser Glu
1               5                   10                  15
```

-continued

Asn Lys Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Asp
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Asp
            85                  90                  95

Met Met Glu Ser Ile Arg Cys Leu Lys Glu Ala Ser Leu Ser Leu Leu
        100                 105                 110

Asp Glu Glu Asp Ala Lys Glu Thr Ala Pro Tyr Phe Asp Tyr Ile Ile
        115                 120                 125

Lys Ala Met Ser
        130

<210> SEQ ID NO 38
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 38

Met Lys Thr Cys Glu Gln Arg Val Asn Ile Ala Thr Leu Leu Thr Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Gly Ile Arg Glu Met Tyr Asn Ser Leu Gly Val Pro Val Pro Ala
            85                  90                  95

Met Met Glu Ser Ile Arg Cys Leu Lys Glu Ala Ser Leu Ser Leu Leu
        100                 105                 110

Asp Glu Glu Asp Ala Asn Glu Thr Ala Pro Tyr Phe Asp Tyr Ile Ile
        115                 120                 125

Lys Ala Met Ser
        130

<210> SEQ ID NO 39
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 39

Met Lys Thr Cys Glu Gln Arg Val Asn Ile Ala Thr Leu Leu Thr Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

```
Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
65                  70                  75                  80

Ile Ser Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Glu Glu Glu Asp Ala Asn Glu Thr Ala Pro Tyr Phe Asp Tyr Ile Ile
        115                 120                 125

Lys Ala Met Ser
        130

<210> SEQ ID NO 40
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 40

Met Lys Thr Ser Glu Gln Arg Val Asn Ile Ala Thr Leu Leu Thr Glu
1               5                   10                  15

Asn Lys Lys Lys Ile Val Asp Lys Ala Ser Gln Asp Leu Trp Arg Arg
            20                  25                  30

His Pro Asp Leu Ile Ala Pro Gly Gly Ile Ala Phe Ser Gln Arg Asp
        35                  40                  45

Arg Ala Leu Cys Leu Arg Asp Tyr Gly Trp Phe Leu His Leu Ile Thr
    50                  55                  60

Phe Cys Leu Leu Ala Gly Asp Lys Gly Pro Ile Glu Ser Ile Gly Leu
65                  70                  75                  80

Ile Ser Ile Arg Glu Met Tyr Asn Ser Leu Gly Val Pro Val Pro Ala
                85                  90                  95

Met Met Glu Ser Ile Arg Cys Leu Lys Glu Ala Ser Leu Ser Leu Leu
            100                 105                 110

Asp Glu Glu Asp Ala Asn Glu Thr Ala Pro Tyr Phe Asp Tyr Ile Ile
        115                 120                 125

Lys Ala Met Ser
        130

<210> SEQ ID NO 41
<211> LENGTH: 132
<212> TYPE: PRT
<213> ORGANISM: Artificial Sequence
<220> FEATURE:
<223> OTHER INFORMATION: Fluorescent Protein

<400> SEQUENCE: 41

Met Lys Thr Cys Glu Gln Arg Val Lys Ile Ala Thr Leu Leu Ser Glu
1               5                   10                  15

Asn Lys Lys Lys Ile Val Asp Lys Ala Ser Gln Asp Leu Trp Arg Arg
            20                  25                  30

Arg Pro Asp Leu Ile Ala Pro Gly Gly Ile Ala Phe Ser Gln Arg Glu
        35                  40                  45

Arg Ala Leu Cys Leu Arg Asp Tyr Gly Trp Tyr Leu His Leu Ile Thr
    50                  55                  60

Phe Cys Leu Leu Ala Gly Asp Lys Gly Pro Ile Glu Ser Ile Gly Leu
```

```
                65                  70                  75                  80
Ile Gly Ile Arg Glu Met Tyr Asn Ser Leu Gly Val Pro Val Pro Gly
                85                  90                  95

Met Met Glu Ser Ile Arg Cys Leu Lys Glu Ala Ser Leu Ser Leu Leu
                100                 105                 110

Asp Glu Glu Asp Ala Lys Glu Thr Ala Pro Tyr Phe Asp Tyr Ile Ile
                115                 120                 125

Lys Ala Met Ser
    130
```

US 10,501,502 B2

ALLOPHYCOCYANIN ALPHA-SUBUNIT EVOLVED LABELING PROTEINS (SMURFPS)

CROSS REFERENCE TO RELATED APPLICATIONS

The present application claims the benefit of U.S. Provisional Application Ser. No. 62/425,390, filed Nov. 22, 2016, the content of which is hereby expressly incorporated herein by reference in its entirety for all purposes.

GOVERNMENT LICENSE RIGHTS

This invention was made with government support under grant no. NS027177, F32GM089114, and GM086197, awarded by the National Institute of Health. The government has certain rights in the invention.

BACKGROUND OF THE INVENTION

Over millions of years under severe environmental pressure in murky waters, the cyanobacterial light-harvesting phycobiliprotein allophycocyanin (APC) evolved for excitation and emission maxima in the near-infrared (NIR) optical window (650-900 nm). Harnessing the power of this natural selection to develop a new generation of bright and robust fluorescent proteins (FPs) for a range of applications, including deep imaging of mammalian tissue, is needed. (Miyawaki, A. Nature Methods, 13(9):729-730, 2016).

While a variety of fluorescent proteins are known, including: eGFP, mCherry, mCardinal, IFP1.4, IFP2.0, and iRFP713, including work by Atsushi Miyawaki's lab. Traditional FUCCI uses a green and red fluorescent proteins evolved from jellyfish and coral. Despite this, there remains a need in the art for additional proteins with increased stability and increased emission maxima ranges for use in detection methods, including deep tissue imaging.

The present invention provides small ultra-red fluorescent proteins (smURFPs) or smURFP variant polypeptides which are biophysically the brightest far-red and near-infrared fluorescent proteins, fill a spectral gap in excitation wavelength, express efficiently with minimal toxicity, and do not produce hydrogen peroxide. In addition, unlike its precursor, TeAPCα, smURFP variant polypeptides do not require a lyase to covalently attach its chromophore.

The present invention provides novel far-red/near-infrared fluorescent proteins from allophycocyanin α-subunit from cyanobacteria *Trichodesmium erythraeum*, referred to small ultra-red fluorescent proteins (smURFPs). These proteins are in the spectral space 600-650 nm, a space not covered by commercially available reagents. smURFPs contain an enlarged chromophore binding site amenable for tagging to different probes using click chemistry. Moreover, biliverdin tagged proteins are suitable for in vivo imaging in cancer and other maladies where hydrogen peroxide is generated. Thus the smURFPs of the invention meet an unmet need.

REFERENCE TO A "SEQUENCE LISTING," A TABLE, OR A COMPUTER PROGRAM, LISTING APPENDIX SUBMITTED ON A COMPACT DISK

This invention incorporated by reference the Sequence Listing text copy submitted herewith, which was created on Mar. 5, 2018, entitled 008075_5045_US_ST25.txt which is 32 kilobytes in size.

SUMMARY OF THE INVENTION

The present invention provides small ultra-red fluorescent proteins (smURFPs) as described herein.

The present invention provides polypeptides comprising an amino acid selected from the group consisting of the smURFP variant polypeptide amino acid sequences recited in FIG. 7.

In some embodiments, the present invention provides a polypeptide comprising an amino acid selected from the group consisting of the smURFP variant polypeptide amino acid sequences recited in SEQ ID Nos: 2 through 14.

In some embodiments, the present invention provides a smURFP variant polypeptide derived from the APCα from *Trichodesmium erythraeum* (TeAPCa) parent polypeptide, where said peptide is at least 80% identical to the TeAPCa parent polypeptide and exhibits one or more characteristics selected from the group consisting of:
  a) increased Fluorescence of smURFP as compared to infrared FPs IFP1.4 and iRFP713;
  b) express efficiently with minimal toxicity;
  c) does not require a lyase to covalently attach its chromophore, wherein the chromophore is biliverdin;
  d) exhibits a wavelength longer than attainable with jellyfish- or coral-derived FPs using smURFP and IFP2.0;
  e) allows for functional fusion to hCdt1(30/120) as compared to jellyfish- or coral-derived FPs mAG, eGFP, and mRFP1 which are nonfunctional;
  f) allows for deep tissue imaging, including imaging 14-16 mm deep in tissue; and
  g) exhibits an emission maximum in the range of 650 nm to 672 nm.

In some embodiments, the smURFP variant polypeptide is a dimer comprising two smURFP polypeptides conjugated by a linker. In some embodiments, the linker is an amino-acid linker. In some embodiments, the amino-acid linker comprises 23 amino acids.

In some embodiments, the smURFP variant polypeptide is a dimer comprising one smURFP conjugated to second fluorescent protein by a linker. In some embodiments, the smURFP variant polypeptide the linker is an amino-acid linker. In some embodiments, the linker comprises 23 amino acids.

In some embodiments, the smURFP variant polypeptide comprises a second fluorescent protein selected from the group consisting of eGFP, mCherry, mCardinal, IFP1.4, IFP2.0, and iRFP713.

In some embodiments, the smURFP variant polypeptide comprises an amino acid substitution at one or more positions selected from the group consisting of 4, 9, 15, 18, 33, 36, 42, 45, 48, 56, 57, 59, 61, 65, 66, 73, 82, 83, 96, 98, 113, 118, 129, 131.

In some embodiments, the smURFP variant polypeptide comprises one or more substitutions selected from the group consisting of G4C, G4S, K9N, S15T, E18K, R33H, F36L, N42I, G45S, E48D, Y56H, G57R, Y59F, R61H, Y65F, G66C, D73G, G82S, V83I, G96A, V98M, D113E, K118N, Q129K, and M131I.

In some embodiments, the smURFP variant polypeptide comprises the consensus sequence (SEQ ID NO:14).

In some embodiments, the smURFP variant polypeptide comprises the amino acids from the consensus sequence at positions 4, 9, 15, 18, 33, 36, 42, 45, 48, 56, 57, 59, 61, 65, 66, 73, 82, 83, 96, 98, 113, 118, 129, 131.

In some embodiments, the smURFP variant polypeptide is at least 85% identical to the TeAPCa parent polypeptide of SEQ ID NO:1. In some embodiments, the smURFP variant polypeptide is at least 90% identical to the TeAPCa parent polypeptide of SEQ ID NO:1. In some embodiments, the smURFP variant polypeptide is at least 95% identical to the TeAPCa parent polypeptide of SEQ ID NO:1. In some embodiments, the smURFP variant polypeptide is at least 98% identical to the TeAPCa parent polypeptide of SEQ ID NO:1.

In some embodiments, the smURFP variant polypeptide is selected from the group consisting of R5-2 (SEQ ID NO:6), R6-6 (SEQ ID NO:7), R7-7 (SEQ ID NO:8), R8-8 (SEQ ID NO:9), R8-9 (SEQ ID NO:10), and SmURFP (SEQ ID NO:13).

In some embodiments, the smURFP variant polypeptide is R5-2 (SEQ ID NO:6), which comprises amino acid substitutions G4C and Y56H.

In some embodiments, the smURFP variant polypeptide is R6-6 (SEQ ID NO:7), which comprises amino acid substitutions F36L and D73G.

In some embodiments, the smURFP variant polypeptide is R7-7 (SEQ ID NO:8), which comprises amino acid substitutions E18K, R33H, and M131I.

In some embodiments, the smURFP variant polypeptide is R8-8 (SEQ ID NO:9), which comprises amino acid substitutions E48D, G96A, and K118N.

In some embodiments, the smURFP variant polypeptide is R8-9 (SEQ ID NO:10), which comprises amino acid substitutions K9N, H33R, and G96D.

In some embodiments, the smURFP variant polypeptide is SmURFP (SEQ ID NO:13).

In some embodiments, the invention provides nucleic acids encoding any of the smURFP variant polypeptides described herein.

In some embodiments, the invention provides an expression vector encoding any of the smURFP variant polypeptides described herein.

In some embodiments, the invention provides a host cell comprising a nucleic acids encoding any of the smURFP variant polypeptides described herein.

In some embodiments, the invention provides a host cell comprising an expression vector encoding any of the smURFP variant polypeptides described herein.

In some embodiments, the invention provides a method of producing a smURFP comprising: a) culturing a host cell according to claim 23 under conditions wherein said polypeptide is produced; and b) purifying said polypeptide.

In some embodiments, the invention provides a method of producing a smURFP comprising: a) culturing a host cell according to claim 24 under conditions wherein said polypeptide is produced; and b) purifying said polypeptide.

In some embodiments, the invention provides a biosensor comprising a smURFP variant polypeptide as described herein. In some embodiments, the biosensor comprises a smURFP variant polypeptide conjugated to hCdt1(30/120), hGem(1/110), or a fragment thereof.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1A-FIG. 1D: Allophycocyanin, chromophore structures, and smURFP mutations. (A) Hexameric structure of APC from the phycobilisome (PDB 1ALL) composed of three α+β dimers. Yellow is α, white is β, and green is PCB. (B) Enlarged α+β dimer illustrating two unique PCB molecules (green) covalently attached by an external protein known as a lyase. (C) Chromophores used in this study: PCB, BV, and BVMe2. Differences from BV are highlighted in yellow in the other two molecules. (D) Homology model of the smURFP homodimer with 20 amino acid mutations highlighted. Covalent attachment of BV (green) is autocatalytic.

FIG. 2A-FIG. 2C: smURFP+BV-purified protein, spectra, and comparison of APCα and BPH FPs expressed in E. coli and smURFP+BV expressed in vivo. (A) Comparison of TeAPCα (expressed with PCB, but needs lyase for incorporation), smURFP+BV, and BV. Top is white light and bottom is fluorescence (EX/EM=650/690 nm). (B) Normalized absorbance and fluorescence spectra of Cy5 and smURFP+BV. (C) Comparison of APCα and BPH FPs expressed in E. coli. E. coli was grown in LB+0.02% arabinose at 37° C. for 17.5 h, and 2 ml of culture was resuspended in 1 ml PBS. Left and right are fluorescent images of FPs expressed in E. coli+HO-1, unless noted, and tubes are outlined in gray. Numbers in white are mean fluorescence intensity. Abs., absorbance; Fluor., fluorescence; EX, excitation maximum; EM, emission maximum; and LP, long pass.

FIG. 3A-FIG. 3E: Increasing chromophore concentration within cells increases fluorescence. HO-1 expression produces BV in situ and increases fluorescence of FPs. (A,B) Quantitation of images in FIG. 13. Fluorescence was normalized to FP IRES eGFP without exogenous BV. Expression of HO-1+5-ALA+FeSO4 significantly increases fluorescence of all FPs. BV was added for 3 h and 5-ALA+FeSO4 for 18 h. Error bars were calculated using error propagation. P-values were determined by a one-way ANOVA using the mean fluorescence intensity. (C) Crystal structure of Deinococcus radiodurans BPH+BV (parent protein of IFP1.4 and IFP2.0). All amino acids ≤3 Å of BV carboxylates are shown in yellow. C24 covalent attachment (cyan) and pyrrole rings are designated by letter. Created from 1ZTU.pdb. (D) Homology model of smURFP+BV showing lack of BV carboxylate recognition. No amino acid is ≤4 Å from the carboxylates. C52 covalent attachment (cyan) and pyrrole rings are designated by letter. BVMe2 increases membrane permeability and smURFP and TDsmURFP fluorescence. (E) Quantitation of images in FIG. 14. All FPs show significant increased fluorescence with BV. smURFP+BVMe2 fluorescence is >32-fold increased relative to smURFP and brighter than the BPH FPs even when excited off peak (right). Chromophore incubation time is 3 h. (A,B,E) Only selected significant differences are shown. Error bars are s.e.m.; n=30; and * is P<0.0001.

FIG. 4A-FIG. 4E: smURFP expressed in vivo and smURFP fusions in mammalian cells. (A) Representative image of smURFP expressed in two HT1080 tumor xenografts without exogenous BV. Fluorescence only (left) and overlay of fluorescence and mouse body (right). Data from three additional mice are shown in FIG. 19. Scale bars, 0.5 cm. (B-D) PC3 cells were transfected with DNA, and FP fusions were imaged 48 h later after incubation with 25 μM BV for 4 h. Fusions at the smURFP N terminus: (B) ManII-10aa-smURFP+BV (mouse, mannosidase II, and Golgi complex) and (C) PDHA1-10aa-smURFP+BV (human, pyruvate dehydrogenase, and mitochondria). Fusions at the smURFP C terminus: (D) smURFP+BV-18aa-αTub (human, α-tubulin, and microtubules) and (E) smURFP+BV-10aa-LamB1 (human, lamin B1, and nuclear envelope). (B-E) Cell images are representative of >20 imaged cells. Similar images were obtained with incubation of 1 μM BVMe2. Scale bars, 10 No. aa, linker length in amino acids and in parentheses: (protein origin, protein name, and cellular location).

FIG. 6: TeAPCα aligned to closest relatives and protein used for homology modeling. TeAPCα, *Trichodesmium erythraeum* allophycocyanin α-subunit (SEQ ID NO:1); MvAPCα, *Microcoleus vaginatus* APCα (SEQ ID NO:21); OnAPCα, *Oscillatoria nigro-viridis* APCα (SEQ ID NO:22); CyAPCα, *Cyanothece* sp. PCC 7425 APCα (SEQ ID NO:23); LaAPCα, *Lynbya aestuarii* BL J APCα (SEQ ID NO:24); LyAPCα, *Lyngbya* sp. PCC 8106 APCα (SEQ ID NO:25); PyAPCα, *Pyropia yezoensis* APCα (SEQ ID NO:26); and consensus sequence (SEQ ID NO:27). TeAPCα is the only protein lacking the first 29 amino acids. Five closest relatives are shown below TeAPCα and the sequence of the structure (1KN1.pdb, PyAPCα) used for homology modeling is last. Changes in amino acids are shown in red. Yellow highlight, conserved C52 for covalent attachment to PCB.

FIG. 7A-FIG. 7F: Evolving new APCα FPs. FPs are named after Round #-Clone # (R#-#), PCB denotes evolution with PCB, and no chromophore label denotes BV. (A,B) Evolving self-incorporation, covalent attachment of PCB produced in *Escherichia coli* (HO-1+PcyA). EX/EM=628/690 nm, respectively. (C-E) Evolving covalent attachment of BV produced in *Escherichia coli* (HO-1). EX/EM=650/690 nm, respectively. R4-1/R5-2 were evolved with BV, EX/EM=685/710 nm, respectively. Rounds 6-12 were evolved with BV, EX/EM=650/690 nm, respectively. (A-E) Red #s are the fold increase in fluorescence relative to left/upper left FP. *Escherichia coli* was grown in LB+0.2% arabinose at 37° C. for ~72 h (A,B) and ~18 h (C-E). (F) Sequence alignment of characterized APCαFPs. TeAPCα is the parent protein and nonfluorescent (FIG. 2A). Green highlight shows the N42I mutation, which allows autocatalytic, covalent attachment of PCB; yellow highlight shows early mutations that occurred in R3-2+PCB and are conserved in all APCαFPs+BV; red highlight shows mutations that cause red-shifted fluorescence; blue highlight shows mutations that are present only in BV binding FPs; purple highlight shows mutations present only in APCαFPs+BV with EX=650 nm; and gray highlight shows mutations that occur only with BV. TeAPCα is SEQ ID NO:28, R1+PCB is SEQ ID NO: 29, R2-1+PCB is SEQ ID NO: 30, R3-2+PCB is SEQ ID NO: 31, R4-1 is SEQ ID NO: 32, R5-2 is SEQ ID NO: 33, R6-6 is SEQ ID NO: 34, R7-7 is SEQ ID NO: 35, R8-8 is SEQ ID NO: 36, R8-9 is SEQ ID NO: 37, R10-10 is SEQ ID NO: 38, R11-2 is SEQ ID NO: 39, smURFP is SEQ ID NO: 40 & Consensus is SEQ ID NO: 41

FIG. 8A-FIG. 8G: Full absorbance and fluorescence spectrum of smURFP and electrospray mass spectrometry of selected, evolved APCα FPs. FPs+HO-1 were expressed in *Escherichia coli* for 18 h at 37° C. and purified as described in the Online Methods. (A) Full absorbance and fluorescence spectra of smURFP+BV purified from *Escherichia coli*. (B) R4-1+BV. Free protein: calculated=16,170.66 D and found=16,169.38 D. FP+BV: calculated=16,753.31 D and found=16,752.63 D. (C) R8-9+BV. Free protein: calculated=16,054.55 D and found=16,053.22 D. FP+BV: calculated=16,637.20 D and found=16,636.47 D. (D) R10-10+BV. Free protein: calculated=15,991.45 D and found=15,990.23 D. FP+BV: calculated=16,574.10 D and found=16,573.48 D. (E) R11-2+BV. Free protein: calculated=16,035.51 D and found=16,034.24 D. FP+BV: calculated=16,618.16 D and found=16,617.49 D. (F) smURFP+BV. Free protein: calculated=15,989.42 D and found=15,988.19 D. FP+BV: calculated=16,572.07 D and found=16,571.44 D. (G) TDsmURFP+BV. Free protein: calculated=32,912.69 D and found=32,911.75 D. TDFP+BV: calculated=33,495.34 D and found=33,495.01 D. (B-G) Average mass calculated by mass spectrometry program Xtract.

FIG. 9A-FIG. 9C: Quaternary structure characterization of smURFP and TDsmURFP. (A) Native PAGE gel of APCαFPs. Monomeric IFP1.4 (36.5 kD) was ran as a reference. R4-1 runs as a tetramer, while R10-10 and smURFP run as a homodimer (32 kD). (B) Native PAGE gel of TDsmURFP. Monomeric IFP1.4 (36.5 kD) and tandem dimer Tomato (tdTomato, 54.2 kD) were ran as references. TDsmURFP (32.9 kD) runs slightly higher than smURFP due to 23 amino acid linker. (C) SDS denaturing PAGE gel of smURFP and TDsmURFP. BV was imaged by addition of zinc. All FPs show correct MW and covalently attached BV. TDsmURFP shows correct MW (32.9 kD) for intact tandem dimer. (A-C) Each FP was run on two lanes. EX is excitation maximum and EM is emission maximum.

FIG. 10A-FIG. 10C: SmURFP C52 covalently attaches BV. (A) smURFP homology model with C52 distances from PCB shown. (B) smURFP C52S eliminates fluorescence. *Escherichia coli* was grown in LB+0.02% arabinose at 37° C. for 16 h. EX/EM=650/690 nm. (C) Electrospray mass spectrometry, average mass of FPs was determined. smURFP. Free protein: calculated=15,989.42 D and found=15,988.19 D. FP+BV: calculated=16,572.07 D and found=16,571.44 D. smURFP C52S. Free protein: calculated=15,973.36 D and found=15,972.21 D. smURFP C52S+BV was not found in the mass spectra.

FIG. 11A-FIG. 11I: Incorporation rates in vitro of BV on initially chromophore-free smURFP. Fluorescence activation of BV by smURFP involves two steps: binding and covalent attachment. 0.5 µM smURFP (1 µM chromophore sites) was incubated with 0.1, 1, and 10 µM BV in PBS alone (A-C) or PBS with 20% FBS (D-F). Increase in fluorescence in (B) PBS at pH 8 or (E) PBS with 20% FBS at pH 9.4. (C,F) Increase in fluorescence in the presence of 1 mM DTT. Fluorescence was monitored and fit to a 1st order increase in fluorescence (F=A[1−exp−kt], data in Table 4). (G,H) The rate of BV incorporation was the similar for all three [BV] and the data was averaged (n=3). Lack of rate change suggests high affinity binding for BV and the rate-limiting step is covalent attachment by C52. Solutions were made basic to increase nucleophilicity of C52. The rate of BV incorporation is increased and proves C52 covalent attachment is the rate-limiting step. SmURFP as the only protein (PBS) shows no significant rate change with 1 mM DTT, but with other proteins (20% FBS) the rate is significantly increased with 1 mM DTT. Error bars are s.e.m.

FIG. 3E). Scale bar=100 μm.

FIG. 16A-FIG. 16F: Chromophore concentration dependence of smURFP and TDsmURFP expressed in HEK293A cells. (A,B) Representative images (6 images total for each sample) of smURFP and TDsmURFP+x □M BV/PCB/BVMe2. Images are adjusted the same only within each set of chromophore and FP. EX/EM=628/680 nm. Exposure time is under each chromophore. Exp. is exposure. Scale bar=100 (C,D) Normalized fluorescence of FP+x μM chromophore. The mean fluorescent intensity (n=30) was determined for each concentration and normalized to brightest FP+x μM chromophore fluorescence. FP is expressed as smURFP/TDsmURFP IRES eGFP. eGFP was measured with BVMe2 addition and also normalized. SmURFP and TDsmURFP are brightest with BVMe2 and PCB is brighter than BV. SmURFP and TDsmURFP+BVMe2/≥40 μM PCB are brighter than eGFP. (E,F) Normalized fluorescence to brightest chromophore concentration for each chromophore set.

FIG. 19A-FIG. 19E: Comparing smURFP and mCherry fluorescence in mouse HT1080 tumor xenografts. (A) Representative fluorescence images (10 images) of FPs expressed in HT108 cells in vitro. 12.5 μM BV was incubated for 3 h. Exposure=200 ms and scale bar=100 μm. (B) Average fluorescent intensity (n=40) of image in a and six other images. (C) Four mice expressing two HT1080 tumors each. Green and red images are EX/EM=590/615LP and 620/645LP nm, respectively. Injection of 250 nmol BV showed no increase in fluorescence after 2 h for all 8 tumors. White # (below tumor) is mean fluorescent intensity. Scale bar=0.5 cm. (D) Mean fluorescent intensity (n=8) of tumors in c. (E) Quantitation of the percent mean fluorescent intensity lost through skin (calculated for each specific tumor). EX is excitation maximum; EM is emission maximum; M# is mouse#; error bars are s.e.m., and * is P<0.0001.

FIG. 20A-FIG. 20G: Comparing smURFP and mCardinal fluorescence in mouse HT1080 tumor xenografts. (A) Representative fluorescence images (10 images) of smURFP T2A mCardinal stably expressed in HT108 cells in vitro, showing >95% transduction efficiency. smURFP and mCardinal fluorescence spectrally overlap and lentivirus and stable cell lines expressing each FP separately was necessary. Similar efficiency was obtained for smURFP and mCardinal stably expressing HT1080 cells. 5 µM BVMe2 was incubated for 3 h. Exposure=50 ms and scale bar=100 µm. (B) White light image of 16 million HT1080 cells stably expressing smURFP (left) and mCardinal (right) before injection into mice. smURFP is visible due to BV present in the fetal bovine serum. (C) Average fluorescent intensity (n=30) of three images. mCardinal fluorescence is not altered by the addition of BVMe2 and expression of mCardinal is the same in the two stable cell lines. (D,E) Average fluorescent intensity (n=30) of 3 images. Addition of BVMe2 for prolonged periods of time stabilizes smURFP and causes increased fluorescence. (D) SmURFP+BVMe2 fluorescence is 2-fold greater than mCardinal, as expected from biophysical properties (Table 3). (E) smURFP fluorescence is 4-fold greater than mCardinal due to enhanced FP expression of the T2A construct (seen also in transient transfection). (F) Five mice with HT1080 tumors. White # (below tumor) is mean fluorescent intensity. The mean fluorescence was calculated by a ROI around the tumor and mouse autofluorescence (left knee) and black background next to mouse was subtracted to correct for background fluorescence. Images are adjusted the same in each row and 640/700 images were brightened 4× to show mC tumors. Scale bar=0.5 cm. (G) Tumor imaging ex vivo 48 h after chromophore i.v. injection. 10 µm chromophore was added in vitro in DMEM+10% FBS. Increase in smURFP fluorescence indicates the gene is expressed and chromophore is not entering cells in vivo. BV and BVMe2 do not non-specifically increase fluorescence in mCardinal expressing tumors. Scale bar=0.5 cm. S is smURFP stably expressing tumor; mC is mCardinal stably expressing tumor; EX is excitation maximum; EM is emission maximum; M# is mouse#; and error bars are s.e.m.

FIG. 23A-FIG. 23C: SmURFP+BV and TDsmURFP+BV are photostable in vitro. Photobleaching experiments were performed as described in the Online Methods. (A) Photobleaching curves of Cy5 and FPs (Left, full time course and Right, magnified view). IFP1.4+BV has $t_{50\%}$=8.4 s, is not photostable, and BV alone does not confer photostability. Cy5 has a $t_{50\%}$=22 s. eGFP has $t_{50\%}$=110 s. TDsmURFP/ smURFP+BV have $t_{50\%}$=190 s and 300 s, respectively, and are very photostable. (B,C) Representative photobleaching of Cy5 and smURFP+BV bubbles. Fluorescent images are adjusted the same and the entire photobleaching series was not included. Scale bar=40 µm.

FIG. 24A-FIG. 24B: Photobleaching of FP or FP fusions in mammalian cells. PC3 cells were transfected with DNA and protein was detected 48 h later. 25 µM BV or 1 µM BVMe2 was incubated for 4 h. Mean fluorescent intensity (n in Table 6) was normalized and averaged for all cells. The time axis represents normalized imaging time for FP initial emission rate of 1,000 photons/sec per chromophore. Full (A) or zoomed in (B) view of photobleaching curves for FP or FP fusions. Curves were fit to a single exponential decay and double exponential decay (data in Table 6). SmURFP average time to bleach 50% emission (n=5) is $t_{50\%}$=340 and 570 sec for BVMe2 and BV, respectively. mCherry is commonly used for superresolution imaging, but is less photostable than smURFP+BV/BVMe$_2$. SmURFP+BV average $t_{50\%}$ is comparable to that of eGFP.

DETAILED DESCRIPTION OF THE INVENTION

Introduction

Figure 5:
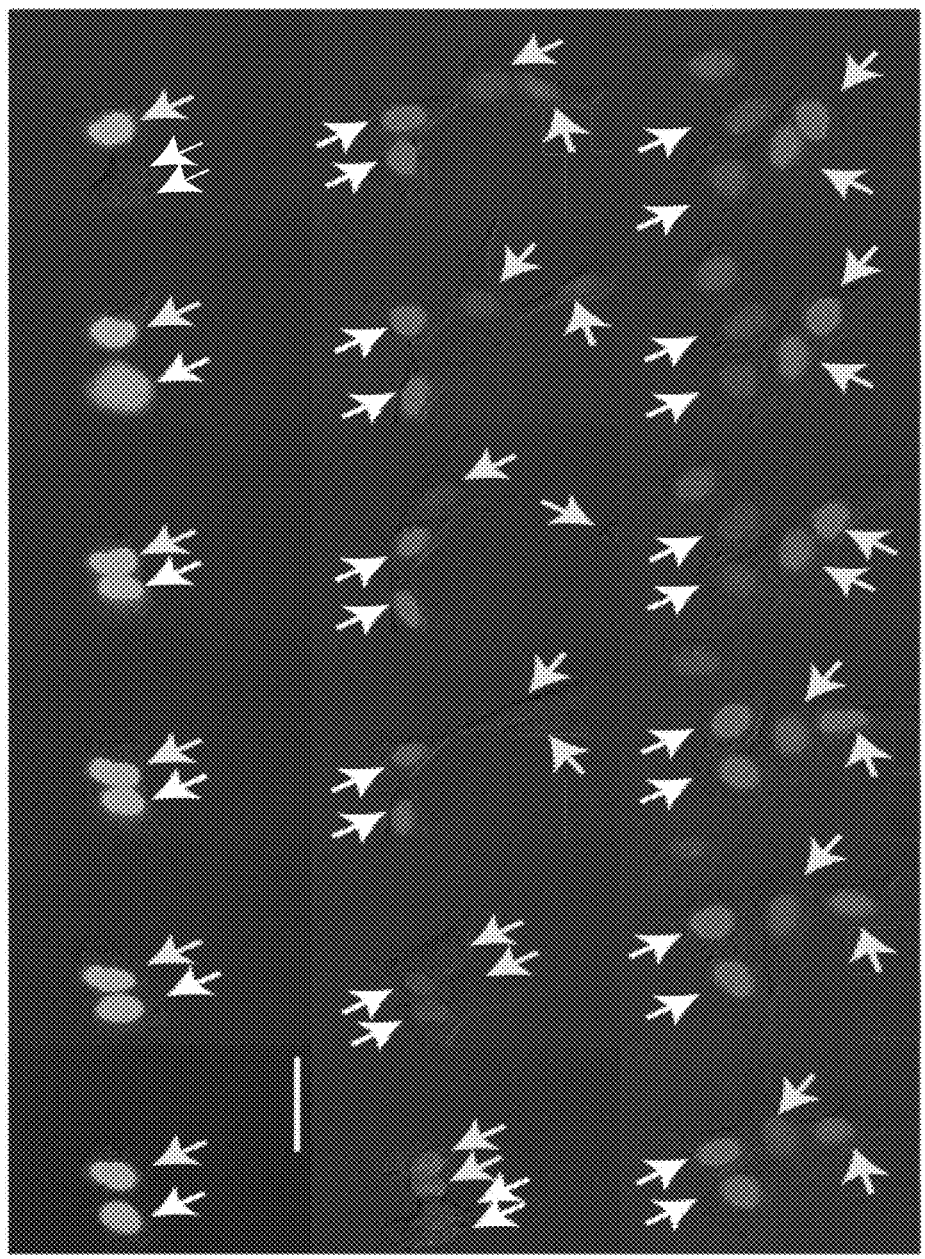
FIG. 5: Time-lapse microscopy of FR and NIR FUCCI expressed in HEK293A cells. IFP2.0-hGem(1/110) and smURFP-hCdtI(30/120) fluorescence are shown in green and red, respectively. White and yellow arrows label original cells and their descendants. HEK293A cell division occurs with a doubling time of ~34 h. Green is EX/EM=665(45)/725(50) nm, and red is EX/EX=628(40)/680(30) nm. Scale bar, 50 µm.

Small ultra red fluorescent protein (smURFP) is a new class of far-red fluorescent protein evolved from a cyanobacterial (*Trichodesmium erythraeum*) phycobiliprotein, α-allophycocyanin. Native α-allophycocyanin requires an exogenous protein, known as a lyase, to attach the chromophore, phycocyanobilin. Phycocyanobilin is not present in mammalian cells. smURFP was evolved to covalently attach phycocyanobilin without a lyase and fluoresce, covalently attach biliverdin (ubiquitous to mammalian cells) and fluoresce, blue-shift fluorescence to match the organic fluorophore, Cy5, and not inhibit *E. coli* growth.

smURFP is a homodimer with absorption and emission maximum of 642 nm and 670 nm, respectively. A tandem dimer smURFP (TDsmURFP) was created and has similar properties to smURFP. smURFP is extremely stable with a protein degradation half-life of 17 hour and 33 hour without and with chromophore (biliverdin), respectively. This is comparable to the jellyfish-derived enhanced green fluorescent protein (eGFP) protein degradation half-life of 24 hour (Stack, J. H.; Whitney, M.; Rodems, S. M.; Pollok, B. A. (2000-12-01). "A ubiquitin-based tagging system for controlled modulation of protein stability". Nature Biotechnology. 18 (12): 1298-1302.) smURFP is extremely photostable and out performs mCherry and tdTomato in living cells. The extinction coefficient (180,000 M−1 cm−1) of smURFP is extremely large and has a modest quantum yield (0.20), which makes it comparable biophysical brightness to eGFP and ~2-fold brighter than most red or far-red fluorescent proteins derived from coral. Despite being a homodimer, all tested N- and C-terminal fusions show correct cellular localization, including the difficult fusion to α-tubulin and Lamin B1.

The optimal wavelength for optical imaging into mammalian tissue is between 600 nm to 1300 nm, where the light scattering decreases with increasing wavelength and absorption by endogenous chromophores is reduced. This allows for the deeper penetration of light into tissue with reduced attenuation (Tromberg, B. J. et al., Neoplasia 2, 26-40 (2000)). Utilization of optogenetic tools to manipulate neuronal activity would have the same wavelength dependence. Current development of channelrhodopsins has produced many variants (e.g., ChR2/H134R, ChETA, TC, SFO/D156A, ChD, oChEF, oChIEF, CatCh and ChRGR) that are maximally activated by blue and green lights (Lin, J. Y. et al., *Biophys J* 96, 1803-1814 (2009); Wen, L. et al., PLoS One September 23; 5(9) (2010); Kleinlogel, S. et al., *Nat Neurosci* 14, 513-518 (2011); Nagel, G. et al., *Curr Biol* 15, 2279-2284 (2005); Gunaydin, L. A. et al., *Nat Neurosci* 13, 387-392 (2010); Berndt, A. et al., *Nat Neurosci* 12, 229-234 (2009); and Berndt, A. et al., *Proc Natl Acad Sci USA* 108, 7595-7600 (2011), the contents of which are hereby expressly incorporated herein by reference in their entireties for all purposes). Many of these variants have improved properties regarding to the kinetics, expression and level of desensitization. However, there has been very little progress in the development of far-red-shifted/near-infrared shifted fluorescent proteins.

Among other embodiments, the present disclosure provides numerous small ultra-red FP (smURFP), as described herein and in the Examples and attachments provided herewith.

DEFINITIONS

The articles "a," "an" and "the" as used herein do not exclude a plural number of the referent, unless context clearly dictates otherwise. The conjunction "or" is not mutually exclusive, unless context clearly dictates otherwise. The term "include" refers to non-exhaustive examples.

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice the present invention. For purposes of the present invention, the following terms are defined.

Although the lengths of smURFPs can vary most and are between 100 and 200 amino acids in length, as shown in FIG. 7.

The term "corresponding residue" refers to an amino acid in a first parent or variant polypeptide which is analogous (e.g., structurally or functionally equivalent) or homologous (e.g., evolutionarily conserved in the primary amino acid sequence) with an amino acid in a second parent or variant polypeptide or reference polypeptide, whether or not the amino acid numbers of the first and second polypeptides align (e.g., corresponding residue 174 in a first smURFP polypeptide may be residue 164 in a second smURFP polypeptide).

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a smURFP polypeptide of the invention linked to a fluorescent protein or fragment thereof or linked to another smURFP (including identical and non-identical smURFPs).

The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains are well known in the art and include, for example, a peptide containing amino acid residues 1 to 81 of human type II membrane-anchored protein galactosyltransferase, or amino acid residues 1 to 12 of the pre-sequence of subunit IV of cytochrome c oxidase (see, also, Hancock et al., *EMBO J.* 10:4033-4039, 1991; Buss et al., *Mol. Cell. Biol.* 8:3960-3963, 1988; U.S. Pat. No. 5,776,689, each of which is incorporated herein by reference). A promoter is a DNA region capable under certain conditions of binding RNA polymerase and initiating transcription of a coding region usually located downstream (in the 3' direction) from the promoter.

The term "heterologous" means derived from a genotypically distinct entity from the rest of the entity it is being compared too. For example, a polynucleotide introduced by genetic engineering techniques into a plasmid or vector derived from a different species is a heterologous polynucleotide. A promoter removed from its native coding sequence and operatively linked to a coding sequence it is not naturally found linked to a heterologous promoter.

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a smURFP described herein can be fused to another fluorescent protein or fragment thereof. In this case, it is preferable that the fusion molecule retains its potential to generate photocurrent and ability to achieve suprathreshold excitement of neurons, and the fluorescent protein or fragment thereof retains its fluorescence. In some embodiments of the present invention, the activities of either the smURFP or the other fluorescent protein can be reduced relative to their activities in isolation. Such fusions can also find use with the present invention.

The terms "polypeptide," "peptide," and "protein" are used interchangeably herein to refer to polymers of amino acids of any length, typically at least 4 or more amino acids. The terms apply to amino acid polymers in which one or more amino acid residue is an artificial chemical analogue of a corresponding naturally occurring amino acid, as well as to naturally occurring amino acid polymers. The "polypeptides," "proteins" and "peptides" encoded by the "polynucleotide sequences," include full-length native sequences, as with naturally occurring proteins, as well as functional subsequences, modified forms or sequence variants so long as the subsequence, modified form, or variant retains some degree of functionality of the native full-length protein. The terms also encompass a modified amino acid polymer; for example, disulfide bond formation, glycosylation, lipidation, phosphorylation, methylation, carboxylation, deamidation, acetylation, or conjugation with a labeling component.

The term "recombinant protein" refers to a protein that is produced by expression of a nucleotide sequence encoding the amino acid sequence of the protein from a recombinant DNA molecule.

The term "wild-type" or "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "non-naturally occurring" is used to refer to a protein, nucleic acid molecule, cell, or other material that does not occur in nature. For example, the smURFPs and fusion proteins thereof provided by the present invention are non-naturally occurring because they contain amino acid variations not found in the corresponding naturally-occurring protein in nature.

The term "identical," when used in reference to two or more polynucleotide sequences or two or more polypeptide sequences, refers to the residues in the sequences that are the same when aligned for maximum correspondence. When percentage of sequence identity is used-in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made using well known methods, for example, scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using any-well known algorithm (see, for example, Meyers and Miller, *Comp. Appl. Biol. Sci.* 4:11-17, 1988; Smith and Waterman, *Adv. Appl. Math.* 2:482, 1981; Needleman and Wunsch, *J. Mol. Biol.* 48:443, 1970; Pearson and Lipman, *Proc. Natl. Acad. Sci., USA* 85:2444 (1988); Higgins and Sharp, *Gene* 73:237-244, 1988; Higgins and Sharp, *CABIOS* 5:151-153; 1989; Corpet et al., *Nucl. Acids Res.* 16:10881-10890, 1988; Huang, et al., *Comp. Appl. Biol. Sci.* 8:155-165, 1992; Pearson et al., *Meth. Mol. Biol.,* 24:307-331, 1994). Alignment also can be performed by simple visual inspection and manual alignment of sequences.

As used herein, the abbreviations for the genetically encoded L-enantiomeric amino acids used in the disclosure methods are conventional and are as follows in Table 1.

TABLE 1

Amino acid abbreviations

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

"Hydrophilic Amino Acid" refers to an amino acid exhibiting a hydrophobicity of less than zero according to the normalized consensus hydrophobicity scale of Eisenberg et al., 1984, J. Mol. Biol. 179: 125-142. Genetically encoded hydrophilic amino acids include Thr (T), Ser (S), His (H), Glu (E), Asn (N), Gln (Q), Asp (D), Lys (K) and Arg (R).

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Basic Amino Acid" refers to a hydrophilic amino acid having a side chain pK value of greater than 7. Basic amino acids typically have positively charged side chains at physiological pH due to association with hydrogen ion. Genetically encoded basic amino acids include His (H), Arg (R) and Lys (K).

"Polar Amino Acid" refers to a hydrophilic amino acid having a side chain uncharged at physiological pH, but which has at least one bond in which the pair of electrons shared in common by two atoms is held more closely by one of the atoms. Genetically encoded polar amino acids include Asn (N), Gln (Q), Ser (S) and Thr (T).

"Hydrophobic Amino Acid" refers to an amino acid exhibiting a hydrophobicity of greater than zero according to the normalized consensus hydrophobicity scale of Eisenberg, 1984, J. Mol. Biol. 179:125-142. Exemplary hydrophobic amino acids include Ile (I), Phe (F), Val (V), Leu (L), Trp (W), Met (M), Ala (A), Gly (G), Tyr (Y), Pro (P), and proline analogues.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6) alkyl, substituted (C1-C6) alkyl, (C1-C6) alkenyl, substituted (C1-C6) alkenyl, (C1-C6) alkynyl, substituted (C1-C6) alkynyl, (C1-C21)) aryl, substituted (C5-C20) aryl, (C6-C26) alkaryl, substituted (C6-C26) alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y) and Trp (W).

"Nonpolar Amino Acid" refers to a hydrophobic amino acid having a side chain uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A).

"Aliphatic Amino Acid" refers to a hydrophobic amino acid having an aliphatic hydrocarbon side chain. Genetically encoded aliphatic amino acids include Ala (A), Val (V), Leu (L) and Ile (I).

The term "non-naturally" with regard to amino acids can include any amino acid molecule not included as one of the 20 amino acids listed in Table 1 above as well as any modified or derivatized amino acid known to one of skill in the art. Non-naturally amino acids can include but are not limited to β-alanine, α-amino butyric acid, γ-amino butyric acid, γ-(aminophenyl) butyric acid, α-amino isobutyric acid, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, methionine sulfone, norleucine, norvaline, ornithine, d-ornithine, p-nitro-phenylalanine, hydroxy proline, 1,2,3, 4,-tetrahydroisoquinoline-3-carboxylic acid, and thioproline.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid.

As to amino acid sequences, one of skill will recognize that individual substitutions, deletions or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Conservative amino acid substitutions providing functionally similar amino acids are well known in the art. Dependent on the functionality of the particular amino acid, i.e., catalytically important, structurally important, sterically important, different groupings of amino acid may be considered conservative substitutions for each other. Table 2 provides groupings of amino acids that are considered conservative substitutions based on the charge and polarity of the amino acid, the hydrophobicity of the amino acid, the surface exposure/structural nature of the amino acid, and the secondary structure propensity of the amino acid.

TABLE 2

Groupings of conservative amino acid substitutions based on the functionality of the residue in the protein.

| Important Feature | Conservative Groupings |
|---|---|
| Charge/Polarity | 1. H, R, and K |
| | 2. D and E |
| | 3. C, T, S, G, N, Q, and Y |
| | 4. A, P, M, L, I, V, F, and W |
| Hydrophobicity | 1. D, E, N, Q, R, and K |
| | 2. C, S, T, P, G, H, and Y |
| | 3. A, M, I, L, V, F, and W |
| Structural/Surface Exposure | 1. D, E, N, Q, H, R, and K |
| | 2. C, S, T, P, A, G, W, and Y |
| | 3. M, I, L, V, and F |
| Secondary Structure Propensity | 1. A, E, Q, H, K, M, L, and R |
| | 2. C, T, I, V, F, Y, and W |
| | 3. S, G, P, D, and N |
| Evolutionary Conservation | 1. D and E |
| | 2. H, K, and R |
| | 3. N and Q |
| | 4. S and T |
| | 5. L, I, and V |
| | 6. F, Y, and W |
| | 7. A and G |
| | 8. M and C |

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity. In certain embodiments, substantially similar sequences will have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity.

A subject nucleotide sequence is considered "substantially complementary" to a reference nucleotide sequence if the complement of the subject nucleotide sequence is substantially identical to the reference nucleotide sequence. The term "stringent conditions" refers to a temperature and ionic conditions used in a nucleic acid hybridization reaction. Stringent conditions are sequence dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature, under defined ionic strength and pH, at which 50% of the target sequence hybridizes to a perfectly matched probe.

The term "allelic variants" refers to polymorphic forms of a gene at a particular genetic locus, as well as cDNAs derived from mRNA transcripts of the genes, and the polypeptides encoded by them. The term "preferred mammalian codon" refers to the subset of codons from among the set of codons encoding an amino acid that are most frequently used in proteins expressed in mammalian cells as chosen from the following list: Gly (GGC, GGG); Glu (GAG); Asp (GAC); Val (GUG, GUC); Ala (GCC, GCU); Ser (AGC, UCC); Lys (AAG); Asn (AAC); Met (AUG); Ile (AUC); Thr (ACC); Trp (UGG); Cys (UGC); Tyr (UAU, UAC); Leu (CUG); Phe (UUC); Arg (CGC, AGG, AGA); Gln (CAG); His (CAC); and Pro (CCC).

As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of the present invention. In general, a fluorescent protein useful for use in a method of the invention is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein. For example, a spectral variant of Aequorea GFP can be derived from the naturally occurring GFP by engineering mutations such as amino acid substitutions into the reference GFP protein.

Many cnidarians use green fluorescent proteins as energy transfer acceptors in bioluminescence. The term "green fluorescent protein" is used broadly herein to refer to a protein that fluoresces green light, for example, Aequorea GFP. GFPs have been isolated from the Pacific Northwest jellyfish, Aequorea victoria, the sea pansy, Renilla reniformis, and Phialidium gregarium (Ward et al., Photochem. Photobiol. 35:803-808, 1982; Levine et al., Comp. Biochem. Physiol. 72B:77-85, 1982, each of which is incorporated herein by reference). Similarly, reference is made herein to "red fluorescent proteins", which fluoresce red, "cyan fluorescent proteins," which fluoresce cyan, and the like. RFPs, for example, have been isolated from the corallimorph Discosoma (Matz et al., Nature Biotechnology 17:969-973 [1999]) and Trichodesmium erythraeum. The term "red fluorescent protein," or "RFP" is used in the broadest sense and specifically covers the Discosoma RFP (DsRed), and red fluorescent proteins from any other species, such as coral and sea anemone, as well as variants thereof as long as they retain the ability to fluoresce red light, as well as the Trichodesmium erythraeum allophycocyanin alpha modified genes as described herein.

The terms "polynucleotide" and "nucleic acid" are used interchangeably herein to refer to all forms of nucleic acid, oligonucleotides, including deoxyribonucleic acid (DNA)

and ribonucleic acid (RNA). Polynucleotides include genomic DNA, cDNA and antisense DNA, and spliced or unspliced mRNA, rRNA, tRNA, lncRNA, RNA antagomirs, and inhibitory DNA or RNA (RNAi, e.g., small or short hairpin (sh)RNA, microRNA (miRNA), aptamers, small or short interfering (si)RNA, trans-splicing RNA, or antisense RNA). Polynucleotides also include non-coding RNA, which include for example, but are not limited to, RNAi, miRNAs, lncRNAs, RNA antagomirs, aptamers, and any other non-coding RNAs known to those of skill in the art. Polynucleotides include naturally occurring, synthetic, and intentionally altered or modified polynucleotides as well as analogues and derivatives. The term "polynucleotide" also refers to a polymeric form of nucleotides of any length, including deoxyribonucleotides or ribonucleotides, or analogs thereof, and is synonymous with nucleic acid sequence. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment as described herein encompassing a polynucleotide encompasses both the double-stranded form and each of two complementary single-stranded forms known or predicted to make up the double-stranded form. Polynucleotides can be single, double, or triplex, linear or circular, and can be of any length. In discussing polynucleotides, a sequence or structure of a particular polynucleotide may be described herein according to the convention of providing the sequence in the 5' to 3' direction.

"Recombinant," as applied to a polynucleotide means the polynucleotide is the product of various combinations of cloning, restriction or ligation steps, and other procedures resulting in a construct distinct and/or different from a polynucleotide found in nature. A recombinant virus is a viral particle encapsidating a recombinant polynucleotide. The terms respectively include replicates of the original polynucleotide construct and progeny of the original virus construct.

The term "in vivo" refers to an event that takes place in a subject's body.

The term "in vitro" refers to an event that takes places outside of a subject's body.

The terms "sample" or "samples" and derivatives thereof as used herein, include any samples obtained from a subject with can be employed with the methods described herein. Samples can include but are not limited to urine, blood, lymph, tears, mucus, saliva, biopsy or other sample tissue samples. Sample can be frozen, refrigerated, previously frozen, and/or stored for minutes, hours, days, weeks, months, years. Sampling techniques, handling and storage are well known and any such techniques for obtaining samples for use with the present invention are contemplated. Tissues can include those from lung, skin, lymph, brain, nerves, muscle, breast, prostate, testis, pancreases, liver, kidneys, stomach, muscle, gastrointestinal, bone and blood.

smURFP Variant Polypeptides

In one aspect, the present disclosure provides new smURFP variant polypeptides. smURFP variant polypeptides are proteins that become depolarized after light activation. They are often used in studies with neurons or are useful when screening certain types of inhibitors that can effect membrane changes in the cell.

In one embodiment, the disclosure provides a smURFP variant polypeptide as shown in FIG. 7, the sequences from which are copied below. In some embodiments, the smURFP variant polypeptide comprises the consensus sequence provided below or a consensus sequence derived from the sequences provided below.

In certain embodiments, additional amino acids may be appended to the N-terminus and/or C-terminus of the smURFP variant polypeptide without affecting the global structure and function of core domains.

In one embodiment, the smURFP variant polypeptide comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of a smURFP recited in FIG. 7, as well as those provided in Table 3 below.

TABLE 3 smURFP sequences generated

| Position | 1 | | | | 5 | | | | | 10 | | | | | 15 | | | | | 20 | | | | | 25 |
|---|---|---|---|---|---|---|---|---|---|---|---|---|---|---|---|---|---|---|---|---|---|---|---|---|---|
| Consensus SEQ ID NO: 41 | M | K | T | C | E | Q | R | V | K | I | A | T | L | L | S | E | N | K | K | K | I | V | D | K | A |
| TeAPCα (SEQ ID NO: 28) | M | K | T | G | E | Q | R | V | K | I | A | T | L | L | S | E | N | E | K | K | I | V | D | K | A |
| R1 + PCB (SEQ ID NO: 29) | M | K | T | G | E | Q | R | V | K | I | A | T | L | L | S | E | N | E | K | K | I | V | D | K | A |
| R2-1 + PCB (SEQ ID NO: 30) | M | K | T | G | E | Q | R | V | K | I | A | T | L | L | S | E | N | E | K | K | I | V | D | K | A |
| R3-2 + PCB (SEQ ID NO: 31) | M | K | T | G | E | Q | R | V | K | I | A | T | L | L | S | E | N | E | K | K | I | V | D | K | A |

TABLE 3-continued smURFP sequences generated

| | | | | | | | | | | | | | | | | | | | | | | | | | |
|---|---|---|---|---|---|---|---|---|---|---|---|---|---|---|---|---|---|---|---|---|---|---|---|---|---|
| R4-1 (SEQ ID NO: 32) | M | K | T | G | E | Q | R | V | K | I | A | T | L | L | S | E | N | E | K | K | I | V | D | K | A |
| R5-2 (SEQ ID NO: 33) | M | K | T | C | E | Q | R | V | K | I | A | T | L | L | S | E | N | E | K | K | I | V | D | K | A |
| R6-6 (SEQ ID NO: 34) | M | K | T | C | E | Q | R | V | K | I | A | T | L | L | S | E | N | E | K | K | I | V | D | K | A |
| R7-7 (SEQ ID NO: 35) | M | K | T | C | E | Q | R | V | K | I | A | T | L | L | S | E | N | K | K | K | I | V | D | K | A |
| R8-8 (SEQ ID NO: 36) | M | K | T | C | E | Q | R | V | K | I | A | T | L | L | S | E | N | K | K | K | I | V | D | K | A |
| R8-9 (SEQ ID NO: 37) | M | K | T | C | E | Q | R | V | N | I | A | T | L | L | S | E | N | K | K | K | I | V | D | K | A |
| R10-10 (SEQ ID NO: 38) | M | K | T | C | E | Q | R | V | N | I | A | T | T | L | L | E | N | K | K | K | I | V | D | K | A |
| R11-2 (SEQ ID NO: 39) | M | K | T | C | E | Q | R | V | N | I | A | T | L | L | T | E | N | K | K | K | I | V | D | K | A |
| smURFP (SEQ ID NO: 40) | M | K | T | S | E | Q | R | V | N | I | A | T | L | L | T | E | N | K | K | K | I | V | D | K | A |
| Position | 26 | | | | 30 | | | | | 35 | | | | | 40 | | | | | 45 | | | | | 50 |

| | | | | | | | | | | | | | | | | | | | | | | | | | |
|---|---|---|---|---|---|---|---|---|---|---|---|---|---|---|---|---|---|---|---|---|---|---|---|---|---|
| Consensus SEQ ID NO: 41 | S | Q | D | L | W | R | R | P | D | L | I | A | P | G | G | I | A | F | S | Q | R | E | R | A |
| TeAPCα (SEQ ID NO: 28) | S | Q | D | L | W | R | R | P | D | F | I | A | P | G | G | N | A | F | G | Q | R | E | R | A |
| R1 + PCB (SEQ ID NO: 29) | S | Q | D | L | W | R | R | P | D | F | I | A | P | G | G | I | A | F | G | Q | R | E | R | A |
| R2-1 + PCB (SEQ ID NO: 30) | S | Q | D | L | W | R | R | P | D | F | I | A | P | G | G | I | A | F | G | Q | R | E | R | A |
| R3-2 + PCB (SEQ ID NO: 31) | S | Q | D | L | W | R | R | P | D | F | I | A | P | G | G | I | A | F | G | Q | R | E | R | A |
| R4-1 (SEQ ID NO: 32) | S | Q | D | L | W | R | R | P | D | F | I | A | P | G | G | I | A | F | S | Q | R | E | R | A |
| R5-2 (SEQ ID NO: 33) | S | Q | D | L | W | R | R | P | D | F | I | A | P | G | G | I | A | F | S | Q | R | E | R | A |
| R6-6 (SEQ ID NO: 34) | S | Q | D | L | W | R | R | P | D | L | I | A | P | G | G | I | A | F | S | Q | R | E | R | A |
| R7-7 (SEQ ID NO: 35) | S | Q | D | L | W | R | H | P | D | L | I | A | P | G | G | I | A | F | S | Q | R | E | R | A |

TABLE 3-continued smURFP sequences generated

| | | | | | | | | | | | | | | | | | | | | | |
|---|---|---|---|---|---|---|---|---|---|---|---|---|---|---|---|---|---|---|---|---|---|
| R8-8 (SEQ ID NO: 36) | S | Q | D | L | W | R | R | H | P | D | L | I | A | P | G | G | I | A | F | S | Q | R | D | R | A |
| R8-9 (SEQ ID NO: 37) | S | Q | D | L | W | R | R | R | P | D | L | I | A | P | G | G | I | A | F | S | Q | R | D | R | A |
| R10-10 (SEQ ID NO: 38) | S | Q | D | L | W | R | R | H | P | D | L | I | A | P | G | G | I | A | F | S | Q | R | D | R | A |
| R11-2 (SEQ ID NO: 39) | S | Q | D | L | W | R | R | H | P | D | L | I | A | P | G | G | I | A | F | S | Q | R | D | R | A |
| smURFP (SEQ ID NO: 40) | S | Q | D | L | W | R | R | H | P | D | L | I | A | P | G | G | I | A | F | S | Q | R | D | R | A |

| Position | 51 | | | | 55 | | | | | 60 | | | | | 65 | | | | | 70 | | | | | 75 |
|---|---|---|---|---|---|---|---|---|---|---|---|---|---|---|---|---|---|---|---|---|---|---|---|---|---|
| Consensus (SEQ ID NO: 41) | L | C | L | R | D | Y | G | W | Y | L | H | L | I | T | F | C | L | L | A | G | D | K | G | P | I |
| TeAPCα (SEQ ID NO: 28) | L | C | L | R | D | Y | G | W | Y | L | R | L | I | T | Y | G | L | L | A | G | D | K | D | P | I |
| R1 + PCB (SEQ ID NO: 29) | L | C | L | R | D | Y | G | W | Y | L | R | L | I | T | Y | G | L | L | A | G | D | K | D | P | I |
| R2-1 + PCB (SEQ ID NO: 30) | L | C | L | R | D | Y | G | W | Y | L | R | L | I | T | F | C | L | L | A | G | D | K | D | P | I |
| R3-2 + PCB (SEQ ID NO: 31) | L | C | L | R | D | Y | G | W | Y | L | R | L | I | T | F | C | L | L | A | G | D | K | D | P | I |
| R4-1 (SEQ ID NO: 32) | L | C | L | R | D | Y | R | W | Y | L | H | L | I | T | F | C | L | L | A | G | D | K | D | P | I |
| R5-2 (SEQ ID NO: 33) | L | C | L | R | D | H | R | W | Y | L | H | L | I | T | F | C | L | L | A | G | D | K | D | P | I |
| R6-6 (SEQ ID NO: 34) | L | C | L | R | D | Y | G | W | Y | L | H | L | I | T | F | C | L | L | A | G | D | K | G | P | I |
| R7-7 (SEQ ID NO: 35) | L | C | L | R | D | Y | G | W | Y | L | H | L | I | T | F | C | L | L | A | G | D | K | G | P | I |
| R8-8 (SEQ ID NO: 36) | L | C | L | R | D | Y | G | W | Y | L | H | L | I | T | F | C | L | L | A | G | D | K | G | P | I |
| R8-9 (SEQ ID NO: 37) | L | C | L | R | D | Y | G | W | Y | L | H | L | I | T | F | C | L | L | A | G | D | K | G | P | I |
| R10-10 (SEQ ID NO: 38) | L | C | L | R | D | Y | G | W | Y | L | H | L | I | T | F | C | L | L | A | G | D | K | G | P | I |
| R11-2 (SEQ ID NO: 39) | L | C | L | R | D | Y | G | W | Y | L | H | L | I | T | F | C | L | L | A | G | D | K | G | P | I |

TABLE 3-continued smURFP sequences generated

| | Position | | | | | | | | | | | | | | | | | | | | | | | | |
|---|---|---|---|---|---|---|---|---|---|---|---|---|---|---|---|---|---|---|---|---|---|---|---|---|---|
| | 76 | | | | 80 | | | | 85 | | | | 90 | | | | 95 | | | | 100 | | | | |
| smURFP (SEQ ID NO: 40) | L | C | L | R | D | Y | G | W | F | L | H | L | I | T | F | C | L | L | A | G | D | K | G | P | I |
| Consensus (SEQ ID NO: 41) | E | S | I | G | L | I | G | I | R | E | M | Y | N | S | L | G | V | P | V | P | G | M | M | E | S |
| TeAPCα (SEQ ID NO: 28) | E | S | I | G | L | I | G | V | R | E | M | Y | N | S | L | G | V | P | V | P | G | M | V | E | S |
| R1 + PCB (SEQ ID NO: 29) | E | S | I | G | L | I | G | V | R | E | M | Y | N | S | L | G | V | P | V | P | G | M | V | E | S |
| R2-1 + PCB (SEQ ID NO: 30) | E | S | I | G | L | I | G | V | R | E | M | Y | N | S | L | G | V | P | V | P | G | M | V | E | S |
| R3-2 + PCB (SEQ ID NO: 31) | E | S | I | G | L | I | G | I | R | E | M | Y | N | S | L | G | V | P | V | P | G | M | M | E | S |
| R4-1 (SEQ ID NO: 32) | E | S | I | G | L | I | G | I | R | E | M | Y | N | S | L | G | V | P | V | P | G | M | M | E | S |
| R5-2 (SEQ ID NO: 33) | E | S | I | G | L | I | G | I | R | E | M | Y | N | S | L | G | V | P | V | P | G | M | M | E | S |
| R6-6 (SEQ ID NO: 34) | E | S | I | G | L | I | G | I | R | E | M | Y | N | S | L | G | V | P | V | P | G | M | M | E | S |
| R7-7 (SEQ ID NO: 35) | E | S | I | G | L | I | G | I | R | E | M | Y | N | S | L | G | V | P | V | P | G | M | M | E | S |
| R8-8 (SEQ ID NO: 36) | E | S | I | G | L | I | G | I | R | E | M | Y | N | S | L | G | V | P | V | P | A | M | M | E | S |
| R8-9 (SEQ ID NO: 37) | E | S | I | G | L | I | G | I | R | E | M | Y | N | S | L | G | V | P | V | P | D | M | M | E | S |
| R10-10 (SEQ ID NO: 38) | E | S | I | G | L | I | G | I | R | E | M | Y | N | S | L | G | V | P | V | P | A | M | M | E | S |
| R11-2 (SEQ ID NO: 39) | E | S | I | G | L | I | S | I | R | E | M | Y | N | S | L | G | V | P | V | P | A | M | M | E | S |
| smURFP (SEQ ID NO: 40) | E | S | I | G | L | I | S | I | R | E | M | Y | N | S | L | G | V | P | V | P | A | M | M | E | S |

| | Position | | | | | | | | | | | | | | | | | | | | | | | | |
|---|---|---|---|---|---|---|---|---|---|---|---|---|---|---|---|---|---|---|---|---|---|---|---|---|---|
| | 101 | | | | 105 | | | | | 110 | | | | | 115 | | | | | 120 | | | | | 125 |
| Consensus (SEQ ID NO: 41) | I | R | C | L | K | E | A | S | L | S | L | L | D | E | E | D | A | K | E | T | A | P | Y | F | D |
| TeAPCα (SEQ ID NO: 28) | I | R | C | L | K | E | A | S | L | S | L | L | D | E | E | D | A | K | E | T | A | P | Y | F | D |
| R1 + PCB (SEQ ID NO: 29) | I | R | C | L | K | E | A | S | L | S | L | L | D | E | E | D | A | K | E | T | A | P | Y | F | D |

TABLE 3-continued smURFP sequences generated

| | | | | | | | | | | | | | | | | | | | | | | |
|---|---|---|---|---|---|---|---|---|---|---|---|---|---|---|---|---|---|---|---|---|---|---|
| R2-1 + PCB (SEQ ID NO: 30) | I | R | C | L | K | E | A | S | L | S | L | L | D | E | E | D | A | K | E | T | A | P | Y | F | D |
| R3-2 + PCB (SEQ ID NO: 31) | I | R | C | L | K | E | A | S | L | S | L | L | D | E | E | D | A | K | E | T | A | P | Y | F | D |
| R4-1 (SEQ ID NO: 32) | I | R | C | L | K | E | A | S | L | S | L | L | D | E | E | D | A | K | E | T | A | P | Y | F | D |
| R5-2 (SEQ ID NO: 33) | I | R | C | L | K | E | A | S | L | S | L | L | D | E | E | D | A | K | E | T | A | P | Y | F | D |
| R6-6 (SEQ ID NO: 34) | I | R | C | L | K | E | A | S | L | S | L | L | D | E | E | D | A | K | E | T | A | P | Y | F | D |
| R7-7 (SEQ ID NO: 35) | I | R | C | L | K | E | A | S | L | S | L | L | D | E | E | D | A | K | E | T | A | P | Y | F | D |
| R8-8 (SEQ ID NO: 36) | I | R | C | L | K | E | A | S | L | S | L | L | D | E | E | D | A | N | E | T | A | P | Y | F | D |
| R8-9 (SEQ ID NO: 37) | I | R | C | L | K | E | A | S | L | S | L | L | D | E | E | D | A | K | E | T | A | P | Y | F | D |
| R10-10 (SEQ ID NO: 38) | I | R | C | L | K | E | A | S | L | S | L | L | D | E | E | D | A | N | E | T | A | P | Y | F | D |
| R11-2 (SEQ ID NO: 39) | I | R | C | L | K | E | A | S | L | S | L | L | E | E | E | D | A | N | E | T | A | P | Y | F | D |
| smURFP (SEQ ID NO: 40) | I | R | C | L | K | E | A | S | L | S | L | L | D | E | E | D | A | N | E | T | A | P | Y | F | D |

| Position | 126 | | | | 130 | | |
|---|---|---|---|---|---|---|---|
| Consensus (SEQ ID NO: 41) | Y | I | I | K | A | M | S |
| TeAPCα (SEQ ID NO: 28) | Y | I | I | Q | A | M | S |
| R1 + PCB (SEQ ID NO: 29) | Y | I | I | Q | A | M | S |
| R2-1 + PCB (SEQ ID NO: 30) | Y | I | I | Q | A | M | S |
| R3-2 + PCB (SEQ ID NO: 31) | Y | I | I | Q | A | M | S |
| R4-1 (SEQ ID NO: 32) | Y | I | I | K | A | M | S |
| R5-2 (SEQ ID NO: 33) | Y | I | I | K | A | M | S |

TABLE 3-continued smURFP sequences generated

| | | | | | | | |
|---|---|---|---|---|---|---|---|
| R6-6 (SEQ ID NO: 34) | Y | I | I | K | A | M | S |
| R7-7 (SEQ ID NO: 35) | Y | I | I | K | A | I | S |
| R8-8 (SEQ ID NO: 36) | Y | I | I | K | A | M | S |
| R8-9 (SEQ ID NO: 37) | Y | I | I | K | A | M | S |
| R10-10 (SEQ ID NO: 38) | Y | I | I | K | A | M | S |
| R11-2 (SEQ ID NO: 39) | Y | I | I | K | A | M | S |
| smURFP (SEQ ID NO: 40) | Y | I | I | K | A | M | S |

In some embodiments, the smURFP variant polypeptide comprises the amino acids from the consensus sequence at positions 4, 9, 15, 18, 33, 36, 42, 45, 48, 56, 57, 59, 61, 65, 66, 73, 82, 83, 96, 98, 113, 118, 129, 131, as described in FIG. 7. In some embodiments, the smURFP variant polypeptide comprises one or more substitutions selected from the group consisting of G4C, G4S, K9N, S15T, E18K, R33H, F36L, N42I, G45S, E48D, Y56H, G57R, Y59F, R61H, Y65F, G66C, D73G, G82S, V83I, G96A, V98M, D113E, K118N, Q129K, M131I, as described in FIG. 7. In some embodiments, the smURFP variant polypeptide comprises the sequence referred to as in any of SEQ ID Nos:2-14, as well as in FIG. 7. In some embodiments, the smURFP variant polypeptide comprises the sequence referred to as SmURFP variant polypeptide in FIG. 7 (SEQ ID NO:2). In some embodiments, the smURFP variant polypeptide comprises the sequence referred to as SmURFP variant polypeptide in FIG. 7 (SEQ ID NO:3). In some embodiments, the smURFP variant polypeptide comprises the sequence referred to as SmURFP variant polypeptide in FIG. 7 (SEQ ID NO:4). In some embodiments, the smURFP variant polypeptide comprises the sequence referred to as SmURFP variant polypeptide in FIG. 7 (SEQ ID NO:5). In some embodiments, the smURFP variant polypeptide comprises the sequence referred to as SmURFP variant polypeptide in FIG. 7 (SEQ ID NO:6). In some embodiments, the smURFP variant polypeptide comprises the sequence referred to as SmURFP variant polypeptide in FIG. 7 (SEQ ID NO:7). In some embodiments, the smURFP variant polypeptide comprises the sequence referred to as SmURFP variant polypeptide in FIG. 7 (SEQ ID NO:8). In some embodiments, the smURFP variant polypeptide comprises the sequence referred to as SmURFP variant polypeptide in FIG. 7 (SEQ ID NO:9). In some embodiments, the smURFP variant polypeptide comprises the sequence referred to as SmURFP variant polypeptide in FIG. 7 (SEQ ID NO:10). In some embodiments, the smURFP variant polypeptide comprises the sequence referred to as SmURFP variant polypeptide in FIG. 7 (SEQ ID NO:11). In some embodiments, the smURFP variant polypeptide comprises the sequence referred to as SmURFP variant polypeptide in FIG. 7 (SEQ ID NO:13). In some embodiments, the smURFP variant polypeptide comprises the sequence referred to as SmURFP variant polypeptide in FIG. 7 (SEQ ID NO:13). In some embodiments, the smURFP comprises the consensus sequence, as described in FIG. 7 (SEQ ID NOs: 14). In some embodiments, the smURFP comprises a sequence at least 80%, at least 85%, at least 90%, at least 95%, at least 98%, or at least 99% identical to the consensus sequence, as described in FIG. 7 (SEQ ID NOs: 14).

In some embodiments, the smURFP variant polypeptide comprises a substitution selected from the group consisting of G4C, G4S, K9N, E18K, R33H, F36L, E48D, Y56H, D73G, G96D, G96A, M131I, and K118N. In some embodiments, the smURFP variant polypeptide comprises the substitution G4C. In some embodiments, the smURFP variant polypeptide comprises the substitution Y56H. In some embodiments, the smURFP variant polypeptide comprises the substitutions G4C and Y56H. In some embodiments, the smURFP variant polypeptide comprises the substitution F36L. In some embodiments, the smURFP variant polypeptide comprises the substitutions D73G. In some embodiments, the smURFP variant polypeptide comprises the substitutions F36L and D73G. In some embodiments, the smURFP variant polypeptide comprises the substitution E18K. In some embodiments, the smURFP variant polypeptide comprises the substitution R33H. In some embodiments, the smURFP variant polypeptide comprises the substitution M131I. In some embodiments, the smURFP variant polypeptide comprises the substitutions E18K and R33H. In some embodiments, the smURFP variant polypeptide comprises the substitutions E18K and M131I. In some embodiments, the smURFP variant polypeptide comprises the substitutions R33H and M131I. In some embodiments, the smURFP variant polypeptide comprises the substitutions E18K, R33H, and M131I. In some embodiments, the smURFP comprises the substitution E48D. In some embodiments, the smURFP variant polypeptide comprises the substitution G96A. In some embodiments, the smURFP variant polypeptide comprises the substitutions K118N. In some embodiments, the smURFP variant polypeptide comprises the substitutions E48D and G96A. In some embodiments, the smURFP variant polypeptide comprises the substitutions E48D K118N. In some embodiments, the smURFP variant polypeptide comprises the substitutions G96A and K118N. In some embodiments, the smURFP variant polypeptide comprises the substitutions E48D, G96A, and K118N. In some embodiments, the smURFP variant polypeptide comprises the substitution K9N. In some embodiments, the smURFP variant polypeptide comprises the substitution H33R. In some embodiments, the smURFP variant polypeptide comprises the substitution G96D. In some embodiments, the smURFP variant polypeptide comprises the substitutions K9N and H33R. In some embodiments, the smURFP variant polypeptide comprises the substitutions K9N and G96D. In some embodiments, the smURFP variant polypeptide comprises the substitutions H33R and G96D. In some embodiments, the smURFP variant polypeptide comprises the substitutions K9N, H33R, and G96D. In some embodiments, the substitution is with regard to the wild-type TeAPCα, as provided in SEQ ID NO:1 and FIG. 7.

In some embodiments, the smURFP variant polypeptide is selected from the group consisting of R5-2, R6-6, R7-7, R8-8, and R8-9, wherein:

R5-2: two mutations, G4C and Y56H (SEQ ID NO:6);
R6-6: two mutations, F36L and D73G (SEQ ID NO: 7);
R7-7: three mutations, E18K, R33H, and M131I (SEQ ID NO:8).
R8-8: three mutations, E48D, G96A, and K118N (SEQ ID NO:9), and
R8-9 contained three mutations, K9N, H33R, and G96D (SEQ ID NO:10).

In some embodiments, the smURFP variant polypeptide comprises two substitutions, G4C and Y56H. In some embodiments, the smURFP variant polypeptide comprises two substitutions, F36L and D73G. In some embodiments, the smURFP variant polypeptide comprises three substitutions, E18K, R33H, and M131I. In some embodiments, the smURFP variant polypeptide comprises three substitutions, K9N, H33R, and G96D. In some embodiments, the smURFP variant polypeptide is a smURFP variant polypeptide as provided in FIG. 7 and SEQ ID NO:14

The smURFP variant polypeptides provided herein can produce a higher photocurrent upon photoactivation with orange, orange-red, and red light, as compared to naturally occurring RFP proteins and other red-shifted variants described to date. Accordingly, in one embodiment, a smURFP variant polypeptide provided herein exhibit an emission maximum in the range of 600 nm to 700 nm. In some embodiments, the smURFP variant polypeptides are fluorescent proteins in the spectral space of 600 nm to 650 nm, a space which is not covered by commercially available reagents. In some embodiments, the smURFP variant polypeptide exhibits an emission maximum in the range of 620 nm to 672 nm. In some embodiments, the smURFP variant polypeptide exhibits an emission maximum in the range of 650 nm to 672 nm. In some embodiments, the smURFP variant polypeptide exhibits an emission maximum in the range of 660 nm to 672 nm. In some embodiments, the smURFP variant polypeptide exhibits an emission maximum in the range of 670 nm to 672 nm. In some embodiments, the smURFP variant polypeptide exhibits an emission maximum of 670 nm or 672 nm. In one embodiment, the emission is measured after stimulation with light having a wavelength from 580 nm to 680 nm, 600 nm to 660 nm, or 600 nm to 650 nm, or 650 nm. In one embodiment, the emission is measured after stimulation with light having a wavelength from 600 nm to 650 nm. In some embodiments, the smURFP variant polypeptide is excited with an excitation maximum of 600 nm to 650 nm (i.e., after stimulation with light having a wavelength from 600 nm to 650 nm). In some embodiments, the smURFP variant polypeptide is excited with an excitation maximum of 640 nm to 650 nm (i.e., after stimulation with light having a wavelength from 640 nm to 650 nm). In some embodiments, the smURFP variant polypeptide is excited with an excitation maximum of 642 nm to 646 nm (i.e., after stimulation with light having a wavelength from 642 nm to 646 nm). In some embodiments, the smURFP variant polypeptide is excited with an excitation maximum of 642 nm or 646 nm (i.e., after stimulation with light having a wavelength of 642 nm or 646 nm). See, for example, Table 4 in Example 2.

The smURFP variant polypeptides provided herein are biophysically the brightest FR and NIR FP created, fills a spectral gap in excitation wavelength, expresses efficiently with minimal toxicity, and does not produce hydrogen peroxide. In addition, unlike its precursor, TeAPCα (SEQ ID NO:1), smURFP variant polypeptide does not require a lyase to covalently attach its chromophore. In some embodiments, the smURFP variant polypeptides provided herein exhibit an increase in fluorescence. In some embodiments, the increase in fluorescence is 10-fold, 20-fold, 30-fold, 40-fold, 50-fold, 75-fold, 100-fold, 150-fold, 200-fold, 250-fold, 500-fold, 750-fold, 1000-fold, 1250-fold, or 1500-fold or more as compared to the wild-type TeAPCα of SEQ ID NO:1. In some embodiments, the increase in fluorescence is 10-fold as compared to the wild-type TeAPCα of SEQ ID NO:1. In some embodiments, the increase in fluorescence is 20-fold as compared to the wild-type TeAPCα of SEQ ID NO:1. In some embodiments, the increase in fluorescence is 30-fold as compared to the wild-type TeAPCα of SEQ ID NO:1. In some embodiments, the increase in fluorescence is 40-fold as compared to the wild-type TeAPCα of SEQ ID NO:1. In some embodiments, the increase in fluorescence is 50-fold as compared to the wild-type TeAPCα of SEQ ID NO:1. In some embodiments, the increase in fluorescence is 75-fold as compared to the wild-type TeAPCα of SEQ ID NO:1. In some embodiments, the increase in fluorescence is 100-fold as compared to the wild-type TeAPCα of SEQ ID NO:1. In some embodiments, the increase in fluorescence is 150-fold as compared to the wild-type TeAPCα of SEQ ID NO:1. In some embodiments, the increase in fluorescence is 200-fold as compared to the wild-type TeAPCα of SEQ ID NO:1. In some embodiments, the increase in fluorescence is 250-fold as compared to the wild-type TeAPCα of SEQ ID NO:1. In some embodiments, the increase in fluorescence is 500-fold as compared to the wild-type TeAPCα of SEQ ID NO:1. In some embodiments, the increase in fluorescence is 750-fold as compared to the wild-type TeAPCα of SEQ ID NO:1. In some embodiments, the increase in fluorescence is 1000-fold as compared to the wild-type TeAPCα of SEQ ID NO:1. In some embodiments, the increase in fluorescence is 1250-fold as compared to the wild-type TeAPCα of SEQ ID NO:1. In some embodiments, the increase in fluorescence is 1500-fold as compared to the wild-type TeAPCα of SEQ ID NO:1.

In some embodiments, the smURFP variant polypeptides contain an enlarged chromophore binding site amenable for tagging to different probes using click chemistry (aka, tagging). Click chemistry (aka, tagging), can find use in joining the smURFPs of the invention to a chromophore. Such chemistry can also be employed to conjugate molecules including but not limited to FAM to the smURFPs, as well as any other fluorophores. In some embodiments, the smURFP is conjugated to PEG-FAM. In some embodiments, the smURFP is conjugated to BV-PEG-FAM.

In some embodiments, the smURFP variant polypeptides comprise fluorophores. Fluorophores are commercially available and any known and/or commercially available fluorophore can be joined to the smURFP. In some embodiments, smURFPs can be linked to other fluorescent dyes, including but not limited to FAM, FAM-PEG, 6-FAM-PEG 3-azide, CAS #: N/A, 6-Carboxyfluorescein-PEG 3-azide, Fluorescent Dyes, 5-FAM, 6-FAM, 5-TAMRA, 6-TAMRA, 5-FITC, and 6-FITC, in order to deliver dyes to specific cells. Such dyes can be linked via many methods known in the art, including click chemistry. In some embodiments, the fluorophore exhibits green fluorescence (such as for example 494 nm/519 nm), orange fluorescence (such as for example 554 nm/570 nm), red fluorescence (such as for example 590 nm/617 nm), or far red fluorescence (such as for example 651 nm/672 nm) excitation/emission spectra. In some embodiments, the fluorophore is a fluorophore with excitation and emission spectra in the range of about 350 nm to about 775 nm. In some embodiments the excitation and emission spectra are about 346 nm/446 nm, about 494 nm/519 nm, about 554 nm/570 nm, about 555 nm/572 nm, about 590 nm/617 nm, about 651 nm/672 nm, about 679 nm/702 nm or about 749 nm/775 nm. In some embodiments, the fluorophore can include but is not limited to AlexaFluor 3, AlexaFluor 5, AlexaFluor 350, AlexaFluor 405, AlexaFluor 430, AlexaFluor 488, AlexaFluor 500, AlexaFluor 514, AlexaFluor 532, AlexaFluor 546, AlexaFluor 555, AlexaFluor 568, AlexaFluor 594, AlexaFluor 610, AlexaFluor 633, AlexaFluor 647, AlexaFluor 660, AlexaFluor 680, AlexaFluor 700, and AlexaFluor 750 (Molecular Probes AlexaFluor dyes, available from Life Technologies, Inc. (USA)). In some embodiments, the fluorophore can include but is not limited to Cy dyes, including Cy2, Cy3, Cy3B, Cy3.5, Cy5, Cy5.5 and Cy7 (available from GE Life Sciences or Lumiprobes). In some embodiments the fluorophore can include but is not limited to DyLight 350, DyLight 405, DyLight 488, DyLight 550, DyLight 594, DyLight 633, DyLight 650, DyLight 680, DyLight 750 and DyLight 800 (available from Thermo Scientific (USA)). In some embodiments, the fluorophore can include but is not limited to a FluoProbes 390, FluoProbes 488, FluoProbes 532, FluoProbes 547H, FluoProbes 594, FluoProbes 647H, FluoProbes 682, FluoProbes 752 and FluoProbes 782, AMCA, DEAC (7-Diethylaminocoumarin-3-carboxylic acid); 7-Hydroxy-4-methylcoumarin-3; 7-Hydroxycoumarin-3; MCA (7-Methoxycoumarin-4-acetic acid); 7-Methoxycoumarin-3; AMF (4'-(Aminomethyl)fluorescein); 5-DTAF (5-(4,6-Dichlorotriazinyl)aminofluorescein); 6-DTAF (6-(4,6-Dichlorotriazinyl)aminofluorescein); 6-FAM (6-Carboxyfluorescein), 5(6)-FAM cadaverine; 5-FAM cadaverine; 5(6)-FAM ethylenediamme; 5-FAM ethylenediamme; 5-FITC (FITC Isomer I; fluorescein-5-isothiocyanate); 5-FITC cadaverin; Fluorescein-5-maleimide; 5-IAF (5-Iodoacetamidofluorescein); 6-JOE (6-Carboxy-4',5'-dichloro-2',7'-dimethoxyfluorescein); 5-CR110 (5-Carboxyrhodamine 110); 6-CR110 (6-Carboxyrhodamine 110); 5-CR6G (5-Carboxyrhodamine 6G); 6-CR6G (6-Carboxyrhodamine 6G); 5(6)-Carboxyrhodamine 6G cadaverine; 5(6)-Caroxyrhodamine 6G ethylenediamme; 5-ROX (5-Carboxy-X-rhodamine); 6-ROX (6-Carboxy-X-rhodamine); 5-TAMRA (5-Carboxytetramethylrhodamine); 6-TAMRA (6-Carb oxytetramethylrhodamine); 5-TAMRA cadaverine; 6-TAMRA cadaverine; 5-TAMRA ethylenediamme; 6-TAMRA ethylenediamme; 5-TMR C6 maleimide; 6-TMR C6 maleimide; TR C2 maleimide; TR cadaverine; 5-TRITC; G isomer (Tetramethylrhodamine-5-isothiocyanate); 6-TRITC; R isomer (Tetramethylrhodamine-6-isothiocyanate); Dansyl cadaverine (5-Dimethylaminonaphthalene-1-(N-(5-aminopentyl))sulfonamide); EDANS C2 maleimide; fluorescamine; NBD; and pyrromethene and derivatives thereof.

In some embodiments, the disclosure provides polypeptide variants, such as the smURFP variant polypeptides described herein. A "polypeptide variant" or a "variant" or "smURFP" has the sequence of a parent polypeptide that has been varied by one or more amino acid mutations (e.g., deletion, insertion or substitution in any combination). In some embodiments, a polypeptide variant is characterized by 1, 2, 3, 4, 5, 6, 7, 8, 9 10, or more mutations, as compared to a parent polypeptide. In some embodiments, a polypeptide variant is characterized by 1, 2, 3, 4, 5, 6, 7, 8, 9 10, or more substitutions, as compared to a parent polypeptide. as compared to a parent polypeptide. In some embodiments, a polypeptide variant is characterized by 1, 2, 3 or 4 substitutions, as compared to a parent polypeptide. In some embodiments, a polypeptide variant is characterized by 1 or more substitutions, as compared to a parent polypeptide. In some embodiments, a polypeptide variant is characterized by 2 or more substitutions, as compared to a parent polypeptide. In some embodiments, a polypeptide variant is characterized by 3 or more substitutions, as compared to a parent polypeptide. In some embodiments, a polypeptide variant is characterized by 4 or more substitutions, as compared to a parent polypeptide. In some embodiments, a polypeptide variant is characterized by 5 or more substitutions, as compared to a parent polypeptide. In some embodiments, a polypeptide variant is characterized by 6 or more substitutions as compared to a parent polypeptide. In some embodiments, the parent polypeptide is APCα from *Trichodesmium erythraeum* (TeAPCα; SEQ ID NO:1), as provide in FIG. 7 and Table 3 above.

Recombinant Expression of smURFPs, Expression Vectors and Host Cells

In some embodiments, smURFPs of the instant invention are synthetic, or are produced by expression of a recombinant nucleic acid molecule. In the event the polypeptide is a chimera (e.g., a fusion protein containing at least a smURFP variant polypeptide and a heterologous polypeptide), it can be encoded by a hybrid nucleic acid molecule containing one sequence that encodes all or part of the smURFP variant polypeptide, and a second sequence that encodes all or part of the heterologous polypeptide.

Methods for constructing a DNA sequence encoding the smURFP variant polypeptide and expressing those sequences in a suitably transformed host include, but are not limited to, using a PCR-assisted mutagenesis technique. Mutations that consist of deletions or additions of amino acid residues to a smURFP variant polypeptide can also be made with standard recombinant techniques. In the event of a deletion or addition, the nucleic acid molecule encoding smURFP variant polypeptide is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

The complete amino acid sequence can be used to construct a back-translated gene. A DNA oligomer containing a nucleotide sequence coding for smURFP variant polypeptide can be synthesized. For example, several small oligonucleotides coding for portions of the desired polypeptide can be synthesized and then ligated. The individual oligonucleotides typically contain 5' or 3' overhangs for complementary assembly.

In addition to generating mutant polypeptides via expression of nucleic acid molecules that have been altered by recombinant molecular biological techniques, subject smURFP variant polypeptides can be chemically synthesized. Chemically synthesized polypeptides are routinely generated by those of skill in the art.

Once assembled (by synthesis, site-directed mutagenesis or another method), the DNA sequences encoding a smURFP variant polypeptide will be inserted into an expression vector and operatively linked to an expression control sequence appropriate for expression of the smURFP variant polypeptide in the desired transformed host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The DNA sequence encoding the smURFP variant polypeptide, whether prepared by site directed mutagenesis, chemical synthesis or other methods, can also include DNA sequences that encode a signal sequence. Such signal sequence, if present, should be one recognized by the cell chosen for expression of the smURFP variant polypeptide. It can be prokaryotic, eukaryotic or a combination of the two. The inclusion of a signal sequence depends on whether it is desired to secrete the smURFP variant polypeptide from the recombinant cells in which it is made. If the chosen cells are prokaryotic, it generally is preferred that the DNA sequence not encode a signal sequence.

smURFP Protein Fusions and Linkers

As noted above, exemplary smURFP variant polypeptide can be prepared as fusion or chimeric polypeptides that include a smURFP variant polypeptide and a heterologous polypeptide (i.e., a polypeptide that is not smURFP or variant thereof). In some embodiments, the smURFP is a linked or fused to another smURFP. In some embodiments, the smURFP is a dimer. In some embodiments, the smURFP is a dimer comprising a linker. In some embodiments, the dimer is a homodimer of two identical smURFP variant polypeptides. In some embodiments, the dimer is a heterodimer of two different smURFP variant polypeptides.

In some embodiments, one smURFP variant polypeptide is linked to another smURFP variant polypeptide or other heterologous polypeptide via an amino acid linker. In some embodiments, the smURFP variant polypeptide is linked directly to another smURFP variant polypeptide or heterologous polypeptide. In some embodiments, the smURFP variant polypeptide is linked to the polypeptide via a linker peptide (i.e., an amino acid linker). In some embodiments, the linker was the 23-amino-acid linker, GHGTG-STGSGSSGTASSEDNNMA (SEQ ID NO:15). In some embodiments, the smURFP variant polypeptide is linked to the polypeptide via a linker peptide, such as GGGGS (SEQ ID NO:16). In some embodiments, the linker is (GGGGS)n, wherein n is an integer between 1 and 10. In some embodiments, the linker is GGGGS. In some embodiments, the linker is GGGGSGGGGS (SEQ ID NO:17). In some embodiments, the linker is GGGGSGGGGSGGGGS (SEQ ID NO:18). In some embodiments, the linker is GGGGSGGGGSGGGGSGGGGS (SEQ ID NO:19). In some embodiments, the linker is GGGGSGGGGSGGGGSGGGGSGGGGS (SEQ ID NO:20).

In some embodiments, smURFP variant polypeptide comprises one of the following sequences:

```
R1 + PCB                                    (SEQ ID NO: 2)
MKTGEQRVKIATLLSENEKKIVDKASQDLWRRRPDFIAPGGIAFGQRERA

LCLRDYGWYLRLITYGLLAGDKDPIESIGLIGVREMYNSLGVPVPGMVES

IRCLKEASLSLLDEEDAKETAPYFDYIIQAMS

R2-1 + PCB                                  (SEQ ID NO: 3)
MKTGEQRVKIATLLSENEKKIVDKASQDLWRRRPDFIAPGGIAFGQRERA

LCLRDYGWYLRLITFCLLAGDKDPIESIGLIGVREMYNSLGVPVPGMVES

IRCLKEASLSLLDEEDAKETAPYFDYIIQAMS

R3-2 + PCB                                  (SEQ ID NO: 4)
MKTGEQRVKIATLLSENEKKIVDKASQDLWRRRPDFIAPGGIAFGQRERA

LCLRDYGWYLRLITFCLLAGDKDPIESIGLIGIREMYNSLGVPVPGMMES

IRCLKEASLSLLDEEDAKETAPYFDYIIQAMS

R4-1                                        (SEQ ID NO: 5)
MKTGEQRVKIATLLSENEKKIVDKASQDLWRRRPDFIAPGGIAFSQRERA

LCLRDYRWYLHLITFCLLAGDKDPIESIGLIGIREMYNSLGVPVPGMMES

IRCLKEASLSLLDEEDAKETAPYFDYIIKAMS

R5-2                                        (SEQ ID NO: 6)
MKTCEQRVKIATLLSENEKKIVDKASQDLWRRRPDFIAPGGIAFSQRERA

LCLRDHRWYLHLITFCLLAGDKDPIESIGLIGIREMYNSLGVPVPGMMES

IRCLKEASLSLLDEEDAKETAPYFDYIIKAMS

R6-6                                        (SEQ ID NO: 7)
MKTCEQRVKIATLLSENEKKIVDKASQDLWRRRPDLIAPGGIAFSQRERA

LCLRDYGWYLHLITFCLLAGDKGPIESIGLIGIREMYNSLGVPVPGMMES

IRCLKEASLSLLDEEDAKETAPYFDYIIKAMS

R7-7                                        (SEQ ID NO: 8)
MKTCEQRVKIATLLSENKKKIVDKASQDLWRRHPDLIAPGGIAFSQRERA

LCLRDYGWYLHLITFCLLAGDKGPIESIGLIGIREMYNSLGVPVPGMMES

IRCLKEASLSLLDEEDAKETAPYFDYIIKAIS

R8-8                                        (SEQ ID NO: 9)
MKTCEQRVKIATLLSENKKKIVDKASQDLWRRHPDLIAPGGIAFSQRDRA

LCLRDYGWYLHLITFCLLAGDKGPIESIGLIGIREMYNSLGVPVPAMMES

IRCLKEASLSLLDEEDANETAPYFDYIIKAMS

R8-9                                        (SEQ ID NO: 10)
MKTCEQRVNIATLLSENKKKIVDKASQDLWRRRPDLIAPGGIAFSQRDRA
LCLRDYGWYLHLITFCLLAGDKGPIESIGLIGIREMYNSLGVPVPDMMES
IRCLKEASLSLLDEEDAKETAPYFDYIIKAMS
```

-continued

```
R10-10                                    (SEQ ID NO: 11)
MKTCEQRVNIATLLTENKKKIVDKASQDLWRRHPDLIAPGGIAFSQRDRA

LCLRDYGWYLHLITFCLLAGDKGPIESIGLIGIREMYNSLGVPVPAMMES

IRCLKEASLSLLDEEDANETAPYFDYIIKAMS

R11-2                                     (SEQ ID NO: 12)
MKTCEQRVNIATLLTENKKKIVDKASQDLWRRHPDLIAPGGIAFSQRDRA

LCLRDYGWYLHLITFCLLAGDKGPIESIGLISIREMYNSLGVPVPAMMES

IRCLKEASLSLLEEEDANETAPYFDYIIKAMS

SmURFP                                    (SEQ ID NO: 13)
MKTSEQRVNIATLLTENKKKIVDKASQDLWRRHPDLIAPGGIAFSQRDRA

LCLRDYGWFLHLITFCLLAGDKGPIESIGLISIREMYNSLGVPVPAMMES

IRCLKEASLSLLDEEDANETAPYFDYIIKAMS

Consensus                                 (SEQ ID NO: 14)
MKTCEQRVKIATLLSENKKKIVDKASQDLWRRRPDLIAPGGIAFSQRERA

LCLRDYGWYLHLITFCLLAGDKGPIESIGLIGIREMYNSLGVPVPGMMES

IRCLKEASLSLLDEEDAKETAPYFDYIIKAMS
```

Nucleic Acid Molecules Encoding smURFPs

In some embodiments, the smURFP variant polypeptides such as those described above, can be obtained by expression of a nucleic acid molecule. Just as smURFP variant polypeptides can be described in terms of their identity with wild-type TeAPCα polypeptide (SEQ ID NO:1), the nucleic acid molecules encoding them will necessarily have a certain identity with those that encode wild-type TeAPCα. For example, the nucleic acid molecule encoding a subject smURFP variant polypeptide can be at least 50%, at least 65%, preferably at least 75%, more preferably at least 85%, and most preferably at least 95% (e.g., 99%) identical to the nucleic acid encoding wild-type TeAPCα (e.g., SEQ ID NO:1).

The nucleic acid molecules provided can contain naturally occurring sequences, or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

The nucleic acid molecules are not limited to sequences that encode polypeptides; some or all of the non-coding sequences that lie upstream or downstream from a coding sequence (e.g., the coding sequence of the smURFP variant polypeptide) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

Exemplary isolated nucleic acid molecules of the present disclosure can include fragments not found as such in the natural state. Thus, this disclosure encompasses recombinant molecules, such as those in which a nucleic acid sequence (for example, a sequence encoding a smURFP variant polypeptide) is incorporated into a vector (e.g., a plasmid or viral vector) or into the genome of a heterologous cell (or the genome of a homologous cell, at a position other than the natural chromosomal location).

As described above, the subject smURFP variant polypeptide peptide may exist as a part of a chimeric polypeptide. In addition to, or in place of, the heterologous polypeptides described above, a subject nucleic acid molecule can contain sequences encoding a "marker" or "reporter." Examples of marker or reporter genes include β-lactamase, chloramphenicol acetyltransferase (CAT), adenosine deaminase (ADA), aminoglycoside phosphotransferase (neo$^r$, G418$^r$), dihydrofolate reductase (DHFR), hygromycin-B-hosphotransferase (HPH), thymidine kinase (TK), lacz (encoding β-galactosidase), and xanthine guanine phosphoribosyltransferase (XGPRT). One of skill in the art will be aware of additional useful reagents, for example, of additional sequences that can serve the function of a marker or reporter.

The subject nucleic acid molecules can be obtained by introducing a mutation into smURFP-encoding DNA or a TeAPCα-encoding DNA.

Expression of smURFP Variant Polypeptide

The nucleic acid molecules described above can be contained within a vector that is capable of directing their expression in, for example, a cell that has been transduced with the vector. Accordingly, in addition to the subject smURFP variant polypeptides, expression vectors containing a nucleic acid molecule encoding a subject smURFP variant polypeptide and cells transfected with these vectors are included as embodiments of the present invention.

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, vectors that can be used include those that allow the DNA encoding the smURFP variant polypeptide to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction of a Modular Dihydrofolate Reductase cDNA Gene: Analysis of Signals Utilized for Efficient Expression", Mol. Cell. Biol., 2, pp. 1304-19 (1982)) or glutamine synthetase ("GS") amplification (see, e.g., U.S. Pat. No. 5,122,464 and European published application 338,841).

In some embodiments, the smURFP variant polypeptides of the present disclosure will be expressed from vectors, preferably expression vectors. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of coding sequences to which they are operably linked. In general, expression vectors of utility in recombinant DNA techniques are often in the form of plasmids (vectors). However, other forms of expression vectors, such as viral vectors (e.g., replication defective retroviruses, adenoviruses, and adeno-associated viruses) are included also.

Exemplary recombinant expression vectors can include one or more regulatory sequences, selected on the basis of the host cells to be used for expression, operably linked to the nucleic acid sequence to be expressed.

The expression constructs or vectors can be designed for expression of a smURFP variant polypeptide in prokaryotic or eukaryotic host cells.

Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

Expression of proteins in prokaryotes is most often carried out in *Escherichia coli* with vectors containing constitutive or inducible promoters. Strategies to maximize recombinant protein expression in *E. coli* can be found, for example, in Gottesman (1990) in Gene Expression Technology: Methods in Enzymology 185 (Academic Press, San Diego, Calif.), pp. 119-128 and Wada et al. (1992) Nucleic Acids Res. 20:2111-2118. Processes for growing, harvesting, disrupting, or extracting the smURFP thereof from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

In some embodiments, the smURFP variant polypeptide can also be made in eukaryotes, such as yeast or human cells. Suitable eukaryotic host cells include insect cells (examples of Baculovirus vectors available for expression of proteins in cultured insect cells (e.g., 519 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerenvisiae* include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus (CMV), and Simian Virus 40. For other suitable expression systems for both prokaryotic and eukaryotic cells, see Chapters 16 and 17 of Sambrook et al. (1989) Molecular Cloning: A Laboratory Manual (2$^{nd}$ ed., Cold Spring Harbor Laboratory Press, Plainview, N.Y.). See, Goeddel (1990) in Gene Expression Technology: Methods in Enzymology 185 (Academic Press, San Diego, Calif.).

The sequences encoding the smURFP variant polypeptides of the present disclosure can be optimized for expression in the host cell of interest. The G-C content of the sequence can be adjusted to levels average for a given cellular host, as calculated by reference to known genes expressed in the host cell. Methods for codon optimization are well known in the art. Codons within the smURFP variant polypeptide coding sequence can be optimized to enhance expression in the host cell, such that about 1%, about 5%, about 10%, about 25%, about 50%, about 75%, or up to 100% of the codons within the coding sequence have been optimized for expression in a particular host cell.

Vectors suitable for use include T7-based vectors for use in bacteria (see, for example, Rosenberg et al., Gene 56:125, 1987), the pMSXND expression vector for use in mammalian cells (Lee and Nathans, J. Biol. Chem. 263:3521, 1988), and baculovirus-derived vectors (for example, the expression vector pBacPAK9 from Clontech, Palo Alto, Calif.) for use in insect cells.

In some embodiments nucleic acid inserts, which encode the subject smURFP variant polypeptide in such vectors, can be operably linked to a promoter, which is selected based on, for example, the cell type in which expression is sought.

In selecting an expression control sequence, a variety of factors should also be considered. These include, for example, the relative strength of the sequence, its controllability, and its compatibility with the actual DNA sequence encoding the subject smURFP variant polypeptide, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters one of skill in the art may select various vector/expression control sequence/host combinations that will express the desired DNA sequences on fermentation or in large scale animal culture, for example, using CHO cells or COS 7 cells.

The choice of expression control sequence and expression vector, in some embodiments, will depend upon the choice of host. A wide variety of expression host/vector combinations can be employed. Useful expression vectors for eukaryotic hosts, include, for example, vectors with expression control sequences from SV40, bovine papilloma virus, adenovirus and cytomegalovirus. Useful expression vectors for bacterial hosts include known bacterial plasmids, such as plasmids from *E. coli*, including col El, pCRI, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2µ plasmid and derivatives thereof. Useful vectors for insect cells include pVL 941 and pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685-98 (1986).

In addition, any of a wide variety of expression control sequences can be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast a-mating system, the polyhedron promoter of Baculovirus, and other sequences known to control the expression of genes of prokaryotic or eukaryotic cells or their viruses, and various combinations thereof.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

In addition to sequences that facilitate transcription of the inserted nucleic acid molecule, vectors can contain origins of replication, and other genes that encode a selectable marker. For example, the neomycin-resistance (neo$^r$) gene imparts G418 resistance to cells in which it is expressed, and thus permits phenotypic selection of the transfected cells. Those of skill in the art can readily determine whether a given regulatory element or selectable marker is suitable for use in a particular experimental context.

Viral vectors that can be used in the invention include, for example, retroviral, adenoviral, and adeno-associated vectors, herpes virus, simian virus 40 (SV40), and bovine papilloma virus vectors (see, for example, Gluzman (Ed.), Eukaryotic Viral Vectors, CSH Laboratory Press, Cold Spring Harbor, N.Y.).

Prokaryotic or eukaryotic cells that contain and express a nucleic acid molecule that encodes a smURFP variant polypeptide disclosed herein are also embodiments of the invention. A cell of the invention is a transfected cell, i.e., a cell into which a nucleic acid molecule, for example a nucleic acid molecule encoding a smURFP variant polypeptide, has been introduced by means of recombinant DNA techniques. The progeny of such a cell are also considered within the scope of the invention.

The precise components of the expression system are not critical. For example, a smURFP variant polypeptide can be produced in a prokaryotic host, such as the bacterium *E. coli*, or in a eukaryotic host, such as an insect cell (e.g., an Sf21 cell), or mammalian cells (e.g., CHO, HEK293, COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

The expressed polypeptides can be purified from the expression system using routine biochemical procedures, and can be used, e.g., as therapeutic agents, as described herein.

Various methods are known for purifying smURFP variant polypeptides. See, e.g. *Current Protocols in Protein Science*, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. smURFPs can be isolated from inclusion bodies generated in *E. coli*, or from conditioned medium from either mammalian or yeast cultures producing a given mutein using cation exchange, gel filtration, and or reverse phase liquid chromatography.

Another exemplary method of constructing a DNA sequence encoding the smURFP variant polypeptides is by chemical synthesis. This includes direct synthesis of a peptide by chemical means of the protein sequence encoding for an smURFP exhibiting the properties described. This method can incorporate both natural and unnatural amino acids. Alternatively, a gene which encodes the smURFP can be synthesized by chemical means using an oligonucleotide synthesizer. Such oligonucleotides are designed based on the amino acid sequence of the desired smURFP, and preferably selecting those codons that are favored in the host cell in which the recombinant mutein will be produced. In this regard, it is well recognized that the genetic code is degenerate—that an amino acid may be coded for by more than one codon. For example, Phe (F) is coded for by two codons, TIC or TTT, Tyr (Y) is coded for by TAC or TAT and his (H) is coded for by CAC or CAT. Trp (W) is coded for by a single codon, TGG. Accordingly, it will be appreciated that for a given DNA sequence encoding a particular smURFP variant polypeptide, there will be many DNA degenerate sequences that will code for that smURFP variant polypeptide. For example, it will be appreciated that in addition to the preferred DNA sequence for a given smURFP, there will be many degenerate DNA sequences that code for the smURFP variant polypeptide. These degenerate DNA sequences are considered within the scope of this disclosure. Therefore, "degenerate variants thereof" in the context of this invention means all DNA sequences that code for and thereby enable expression of a particular mutein.

The biological activity of the smURFP variant polypeptide can be assayed by any suitable method known in the art. Such assays include any of those disclosed herein.

Imaging Applications and Uses, Including Biosensors

In some embodiments, the present invention provides smURFP variant polypeptide s. The smURFPs and smURFP variants that are biophysically the brightest FR (far red) and NIR FP (near infra-red far red) created at present. These smURFP variant polypeptides fill a spectral gap in excitation wavelength, expresses efficiently with minimal toxicity, and do not produce hydrogen peroxide. In addition, unlike its precursor, TeAPCα (SEQ ID NO:1), smURFP variant polypeptide does not require a lyase to covalently attach its chromophore. In some embodiments, the smURFP expresses efficiently in a cell. In some embodiments, the smURFP variant polypeptide expresses efficiently in a cell as compared to TeAPCα (SEQ ID NO:1). In some embodiments, the smURFP variant polypeptides do not produce hydrogen peroxide. In some embodiments, the smURFP variant polypeptides do not produce hydrogen peroxide and are thus less toxic to the cells expressing the peptides. In some embodiments, the smURFP variant polypeptide does not require a lyase to covalently attach is chromophore.

The smURFP variant polypeptides of the present invention can have an enlarged chromophore binding site, which allows for covalent attachment of a hydrophobic biliverdin analog, biliverdin dimethyl ester. For the protein labeling tag (smURFPtag), the organic synthesis of the ligand is described to modify biliverdin with a polyethylene glycol linker and any desired small molecule, including but not limited to, organic dyes, singlet oxygen generators, alkynes/ azides for click chemistry, protein ligands, etc. biliverdin (BV)-polyethylene glycol linker (PEG)-Fluorescein or Methylene Blue were successfully synthesized and purified. BV-PEG-Fluorescein can be genetically targeted to nuclei of living cells and fluorescence is only detected when bound to the smURFPtag. Other dyes can include any of those know in the art or listed herein above.

In some embodiments, the smURFP variant polypeptide fluorescence is visible without exogenous BV and may be advantageous for imaging cancer or other maladies in vivo, where the production of hydrogen peroxide could alter immune system or inflammation response and/or alter disease progression. Here, it is important to note that previous comparisons of BPH FPs and red FPs in vivo were performed using purified FPs, normalizing concentrations with BV already covalently attached, and by embedding FPs inside phantoms into mice[16,17]. This experimental setup does not accurately reflect FP expression and accessibility to BV in vivo where, for example, iRFP7[13] shows little fluorescence when compared to mCardinal[29].

Membrane permeability of BV can be a limiting factor for BPH FPs and smURFP. The development of the smURFP variant polypeptide fluorescence is controlled by the covalent attachment of the cofactor, not by reversible noncovalent BV affinity. HO-1 expression in neurons increases IFP2.0 fluorescence[18]. HO-1 increased fluorescence significantly for BPH and APCα FPs, and it enhanced more with 5-ALA and iron, which fuel production of heme that HO-1 converts to BV. smURFP and TDsmURFP, unlike BPH FPs, tolerate the freely permeant BVMe2. In some embodiments, the smURFP variant polypeptides of the invention contain an open chromophore-binding pocket (for example, as provided in FIG. 3d). In some embodiments, the open chromophore-binding pocket allows for further modification of tetrapyrroles to modify not only membrane permeability but also spectral and fluorescence properties.

According to the present invention, smURFP variant polypeptide photostability is essential for imaging extended time periods or super-resolution. BPH FPs were originally nonfluorescent phototransducers that lacked evolutionary pressure to be light tolerant, whereas APCα is a component of the light-harvesting phycobilisome, which is extremely tolerant of light. Without using a special selection, smURFP is very photostable. In some embodiments, the smURFP variant polypeptide is photostable. Selection for increased photostability should enhance smURFP utility for super-resolution applications. In some embodiments, the smURFP variant polypeptide exhibits increased photostability as compared to a previously known RFP or other fluorescent protein.

In some embodiments, the smURFP variant polypeptides are expressed and/or functional in a eukaryotic cell. In some embodiments, the smURFP variant polypeptides are expressed and/or functional in an insect cell. In some embodiments, the smURFP variant polypeptides are expressed and/or functional in E. coli. In some embodiments, smURFP variant polypeptides are expressed and/or functional in mammalian cells. In some embodiments, the smURFP variant polypeptides are expressed and/or functional in CHO, HEK293, COS cells, NIH 3T3 cells, or HeLa cells. In some embodiments, the smURFP variant polypeptides are expressed and/or functional in a cell available from the American Type Culture Collection (Manassas, Va.). In some embodiments, the smURFP variant polypeptides are expressed and/or functional in a cell from a patient tissue sample.

Biosensors

Far-red/near-infrared fluorescent ubiquitination-based cell cycle indicator (FUCCI): The far-red/near-infrared FUCCI emits fluorescence in a spectral region with little background signal. These wavelengths are amenable for imaging in living organisms, such as mice. The far-red/near-infrared FUCCI creates a fluorescent biosensor with wavelengths inaccessible to jellyfish or coral FPs and does not produce hydrogen peroxide. The far-red/near-infrared FUCCI is the first biosensor using two BV attaching FPs and can be used with traditional FUCCI to monitor the cell cycle of two cell types. In some embodiments, the fluorescent ubiquitination-based cell cycle indicator (FUCCI), in either FR (far red) and/or NIR (near infrared) creates a fluorescent biosensor with wavelengths inaccessible to jellyfish or coral fluorescent proteins a. In some embodiments, the smURFP variant polypeptide is employed as part of the biosensor. In some embodiments, does not produce hydrogen peroxide. Fluorescently monitoring the cell cycle has identified modifications to cell division, drug-induced cell cycle modification, and quiescent cells.

Far-red/near-infrared fluorescent ubiquitination-based cell cycle indicator (FUCCI): In FUCCI, two spectrally distinct FPs are synthesized and degraded at opposing phases of the cell cycle. Typically, a green FP is made during S, G2, or M phase and degraded during late M or G1 phase, while an orange FP is made during G0 or G1 phase and destroyed at the start of S phase. In some embodiments, the smURFPs, of the invention can be used as a far-red/near-infrared biosensor. In some embodiments, fluorescence time-lapse imaging, smURFP-hCdt1(30/120) and IFP2.0-hGem(1/110) reciprocally lit up during the G0 or G1 and S, G2, or M phases, respectively (see, for example, FIG. 5). In some embodiments, using the smURFP variant polypeptides of the invention, fluorescent ubiquitination-based cell cycle indicator (FUCCI) now works in the FR and NIR. In some embodiments, the smURFPs are useful as biosensors.

In some embodiments, the invention provides a biosensor comprising a smURFP peptide as described herein. In some embodiments, the biosensor comprises a dimer of any of the smURFP peptides provided herein. In some embodiments, the biosensor comprises a smURFP of SEQ ID NOs:2-14. In some embodiments, the biosensor comprises a smURFP of SEQ ID NO:2. In some embodiments, the biosensor comprises a smURFP of SEQ ID NO:3. In some embodiments, the biosensor comprises a smURFP of SEQ ID NO:4. In some embodiments, the biosensor comprises a smURFP of SEQ ID NO:5. In some embodiments, the biosensor comprises a smURFP of SEQ ID NO:6. In some embodiments, the biosensor comprises a smURFP of SEQ ID NO:7. In some embodiments, the biosensor comprises a smURFP of SEQ ID NO:8. In some embodiments, the biosensor comprises a smURFP of SEQ ID NO:9. In some embodiments, the biosensor comprises a smURFP of SEQ ID NO:10. In some embodiments, the biosensor comprises a smURFP of SEQ ID NO:11. In some embodiments, the biosensor comprises a smURFP of SEQ ID NO:12. In some embodiments, the biosensor comprises a smURFP of SEQ ID NO:13. In some embodiments, the biosensor comprises a smURFP of SEQ ID NO:14. In some embodiments, the biosensor comprises a smURFP conjugated to hCdt1(30/120), hGem(1/110) or a fragment thereof. In some embodiments, the biosensor comprises a smURFP conjugated to hCdt1(30/120). In some embodiments, the biosensor comprises a smURFP conjugated to hGem(1/110). In some embodiments, the biosensor is capable of detecting G0, G1 and S, or M phases. In addition, smURFP is one of only three FPs (smURFP, mKO2, and mCherry) known to allow functional fusion to hCdt1(30/120) despite the fact that jellyfish- or coral-derived FPs mAG, eGFP, and mRFP1 are nonfunctional. The FR and NIR FUCCI is the first biosensor using two BV-attaching FPs and can be used with traditional FUCCI to monitor the cell cycle of two cell types. In some embodiments, the smURFP variant polypeptides of the invention allow for functional fusion to hCdt1(30/120). In some embodiments, the smURFP variant polypeptides of the invention allow for functional fusion to hGem(1/110).

Data obtainable from the biosensors according to the invention include diagnostic data, data relating to lead compound development, and nucleic acid sensor molecule modeling data. In one embodiment, these data are stored in a computer database. In a further embodiment, the database includes, along with diagnostic data obtained from a sample by the biosensor, information relating to a particular patient, such as medical history and billing information. Although, in one embodiment, the database is part of the nucleic acid sensor molecule system, the database can be used separately with other detection assay methods and drug development methods.

Detectors used with the biosensors according to the invention, can vary, and include any suitable detectors for detecting optical changes in the biosensor. These include, e.g., photomultiplier tubes (PMTs), charge coupled devices (CCDs), intensified CCDs, and avalanche photodiodes (APDs). In one embodiment, a biosensor molecule is excited by a light source in communication with the biosensor. In a further embodiment, when the optical signaling unit comprises first and second signal moieties that are donor/acceptor pairs (i.e., signal generation relies on the fluorescence of a donor molecule when it is removed from the proximity of a quencher acceptor molecule), recognition of a target molecule will cause a large increase in fluorescence emission intensity over a low background signal level. The high signal-to-noise ratio permits small signals to be measured using high-gain detectors, such as PMTs or APDs. Using intensified CCDs, and PMTs, single molecule fluorescence measurements have been made by monitoring the fluorescence emission, and changes in fluorescence lifetime, from donor/acceptor FRET pairs (see Sako, et al., 2000; Lakowicz et al, 1991)).

Photoacoustic Imaging Proteins

Dark smURFP was engineered to rotate the biliverdin out of plane, which causes a red-shifted absorbance and fluorescence and reduces the fluorescence quantum yield, which is desirable to obtain a large acoustic signal. Photoacoustic imaging (optoacoustic imaging) is a biomedical imaging modality based on the photoacoustic effect. In photoacoustic imaging, non-ionizing laser pulses are delivered into biological tissues (when radio frequency pulses are used, the technology is referred to as thermoacoustic imaging). Some of the delivered energy will be absorbed and converted into heat, leading to transient thermoelastic expansion and thus wideband (i.e., MHz) ultrasonic emission. The generated ultrasonic waves are detected by ultrasonic transducers and then analyzed to produce images. Photoacoustic imaging proteins: Dark smURFP has been tested in bacteria in a petri dish and in the bladder of mice by our collaborators (Robert Campbell and Roger Zemp). Robert Campbell and Roger Zemp are testing in mammalian cells at the University of Alberta. Photoacoustic imaging proteins: Dark smURFP allows for greater imaging depth in mice than fluorescence. This protein could be commercialized for imaging in living organisms, including mice. Commercially available photoacoustic imaging systems are now available for mice. Genetically encoded photoacoustic imaging probes are lacking and are highly desired. In some embodiments, the smURFP variant polypeptides can be employed in photoacoustic imaging methods. Photoacoustic imaging is a non-invasive imaging modality which allows structural, functional and molecular imaging. The method relies on the photoacoustic effect which describes conversion between light and acoustic waves due to absorption of electromagnetic waves and localized thermal excitation. Photoacoustic imaging proteins have recently been shown to image deeper than fluorescent proteins in living animals. In some embodiments, the smURFP variant polypeptides exhibit reduced quantum yield and greater photoacoustic signal when compared to iRFP713 and/or mIFP. In some embodiments, the Dark smURFP has reduced quantum yield and greater photoacoustic signal when compared to iRFP713 and/or mIFP. Photoacoustic imaging is detectable in bacterial colonies and bacteria injected into mice and localize to the bladder (14 mm depth). Recently, Halotag (Promega), CLIPtag (New England Biolabs), and SNAPtag (New England Biolabs) have revolutionized the small molecule labeling of proteins in vitro and in vivo. All proteins and small molecule ligands are commercially available (companies in parentheses). For all these labeling technologies, the recognition molecule only serves to covalently attach the molecule to the protein and require extensive washing to remove unbound molecules/fluorophores. In some embodiments, employment of the smURFPtag (for example, a smURFP variant polypeptide linked to BV-PEG-fluorophore) is an improved technology because BV acts as both a recognition molecule for covalent attachment and fluorescence is turned "on" upon covalent attachment. In some embodiments, BV acts as a fluorescence quencher when not bound to the smURFPtag and extensive washing of unbound BV-PEG-Fluorophore is unnecessary.

Far-red/near-infrared fluorescent ubiquitination-based cell cycle indicator (FUCCI): Traditional FUCCI is available from Molecular Probes and Clontech to image the cell cycle. The far-red/near-infrared FUCCI should allow imaging of the cell cycle in vivo. The far-red/near-infrared FUCCI can be used with traditional FUCCI to image the cell cycle phase in two cell types. FUCCI images alterations in cell cycle caused by pharmaceutical drugs. Far-red/near-infrared fluorescent ubiquitination-based cell cycle indicator (FUCCI): Is based on Photoacoustic imaging proteins: smURFP shows greater photoacoustic signal than iRFP713, mIFP, and sGPA0.2. In some embodiments, the smURFP variant polypeptide has a greater and/or enhanced photoacoustic signal than iRFP713, mIFP, or sGPA0.2. In some embodiments, the smURFP variant polypeptide has a greater and/or enhanced photoacoustic signal than iRFP713. In some embodiments, the smURFP variant polypeptide has a greater and/or enhanced photoacoustic signal than mIFP. In some embodiments, the smURFP variant polypeptide has a greater and/or enhanced photoacoustic signal than GPA0.2. In some embodiments, the smURFP variant polypeptide has a photoacoustic that is 1-fold, 2-fold, 3-fold, 4-fold, 5-fold, 10-fold, 20-fold, 50-fold, or 100-fold or more increased photoacoustic signal as compared to iRFP713, mIFP, or sGPA0.2.

In some embodiments, genetically encoded protein labeling tag: SmURFPtag covalently attached modified biliverdin analogs. In some embodiments, biliverdin unbound acts as a fluorescent quencher, but once covalently attached fluorescence is turned on and shows the location of the cargo. Genetically encoded protein labeling tag: The synthesis of biliverdin analogs allows for easy attachment of dyes and molecules through a polyethyleneglycol linker. In some embodiments, the SmURFPtag works in HEK293 cells. In some embodiments, the SmURFPtag is functional in HEK293 cells.

In some embodiments, the SmURFPtag works in any tissue or cell culture. Further characterization and comparison to existing tags is necessary. In some embodiments, synthesis of biliverdin analogs allows for easy attachment of dyes and molecules through a polyethyleneglycol linker Fluorescent protein: SmURFP was engineered to autocatalytically, covalently attach biliverdin without the need of an external protein, known as a lyase. Rigidification of the biliverdin in the binding allows for fluorescence emission.

Fluorescent protein: SmURFP was selected manually after 12 rounds of mutagenesis and 10^6 bacterial colonies. SmURFP has been rigorously tested in many cell types and in mice. The gene has been distributed to >50 researchers on Addgene. Fluorescent protein: Far-red and near-infrared fluorescent proteins are useful for imaging cells, proteins at specific cellular locations, and imaging in living organisms. In some embodiments, fluorescent proteins can be used to label specific cells and/or tissues, such as cancer, to allow for detection in culture and in organisms. Fluorescent proteins, either a single protein or part of a FRET pair, are often used in biosensors to detect small molecules within living cells.

In cell culture, smURFP shows comparable brightness to eGFP and is brighter than mCherry, mCardinal, IFP1.4, IFP2.0, and iRFP713. In some embodiments, the smURFP variant polypeptide has comparable brightness to eGFP. In some embodiments, the smURFP variant polypeptide is brighter (i.e., has increased brightness, increased fluorescence, and/or is more readily detectable) as compared to mCherry. In some embodiments, the smURFP variant polypeptide has comparable brightness to eGFP. In some embodiments, the smURFP variant polypeptide is brighter (i.e., has increased brightness, increased fluorescence, and/or is more readily detectable) as compared to mCardinal. In some embodiments, the smURFP variant polypeptide has comparable brightness to eGFP. In some embodiments, the smURFP variant polypeptide is brighter (i.e., has increased brightness, increased fluorescence, and/or is more readily detectable) as compared to IFP1.4. In some embodiments, the smURFP variant polypeptide has comparable brightness to eGFP. In some embodiments, the smURFP variant polypeptide is brighter (i.e., has increased brightness, increased fluorescence, and/or is more readily detectable) as compared to iRFP713. In some embodiments, the smURFP variant polypeptide is brighter (i.e., has increased brightness, increased fluorescence, and/or is more readily detectable), for example 1-fold, 2-fold, 3-fold, 4-fold, 5-fold, 10-fold, 20-fold, 50-fold, or 100-fold, 250-fold, 500-fold, 750-fold, 1000-fold, 1250-fold, or 1500-fold or more increased brightness and/or increased fluorescence as compared mCherry, mCardinal, IFP1.4, IFP2.0, and/or iRFP713. smURFP is brighter than mCardinal in vitro when BVMe2 is added for 2 d, and it is comparable to eGFP in brightness, which is useful in cell culture for imaging low-copy-number proteins, super-resolution imaging, and biosensors (FRET acceptor or red FP quencher). In some embodiments, the smURFP variant polypeptide is than mCardinal in vitro when BVMe2 is added for 2 d, and it is comparable to eGFP in brightness. smURFP is the most photostable FP tested. smURFP can be fused to α-tubulin (see, for example, FIG. 4d), one of the most sensitive proteins.

In Vivo Uses

The smURFP variant polypeptides of the invention can find use in deep tissue imaging. In some embodiments, imaging can be 5 mm, 10 mm, 12 mm, 14 mm, 16 mm, 18 mm, or 20 mm in depth into a tissue. In some embodiments, the smURFP variant polypeptides of the invention allow for imaging 5 mm, 10 mm, 12 mm, 14 mm, 16 mm, 18 mm, or 20 mm in depth into a tissue in a subject.

In some embodiments, the smURFP variant polypeptides of the invention allow for imaging at 5 mm in depth into a tissue in a subject. In some embodiments, the smURFP variant polypeptides of the invention allow for imaging at 10 mm in depth into a tissue in a subject. In some embodiments, the smURFP variant polypeptides of the invention allow for imaging at 12 mm in depth into a tissue in a subject. In some embodiments, the smURFP variant polypeptides of the invention allow for imaging at 14 mm in depth into a tissue in a subject. In some embodiments, the smURFP variant polypeptides of the invention allow for imaging at 16 mm in depth into a tissue in a subject. In some embodiments, the smURFP variant polypeptides of the invention allow for imaging at 18 mm in depth into a tissue in a subject. In some embodiments, the smURFP variant polypeptides of the invention allow for imaging at 20 mm in depth into a tissue in a subject. In some embodiments, the smURFP variant polypeptides as provided in SEQ ID Nos:2-14, as well as FIG. 7, allow for imaging at 5 mm to 20 mm in depth into a tissue in a subject. In some embodiments, Dark smURFP can be imaged 14-16 mm in tissue. In some embodiments, Dark smURFP can be imaged 14-16 mm in mice bladders, which is far deeper than the imaging depth of fluorescent imaging. In some embodiments, R5-2 (SEQ ID NO:6) can be imaged 14-16 mm in tissue. In some embodiments, R6-6 (SEQ ID NO:7) can be imaged 14-16 mm in tissue. In some embodiments, R7-7 (SEQ ID NO:8) can be imaged 14-16 mm in tissue. In some embodiments, R8-8 (SEQ ID NO:9) can be imaged 14-16 mm in tissue. In some embodiments, R8-9 (SEQ ID NO:10) can be imaged 14-16 mm in tissue. In some embodiments, SmURFP (SEQ ID NO:13) can be imaged 14-16 mm in tissue.

The smURFPs of the invention can be used in basic research but may also have therapeutic qualities. In some embodiments, the smURFPs can be covalently bound to biliverdin. In some embodiments, smURFPs can be linked to other fluorescent dyes, including but not limited to FAM, FAM-PEG, 6-FAM-PEG 3-azide, CAS #: N/A, 6-Carboxyfluorescein-PEG 3-azide, Fluorescent Dyes, 5-FAM, 6-FAM, 5-TAN/IRA, 6-TAMRA, 5-FITC, and 6-FITC, in order to deliver dyes to specific cells. Such dyes can be linked via many methods known in the art, including click chemistry, and include any of those described above.

Detection

Light sources for detecting the include, e.g., filtered, wide-spectrum light sources, (e.g., tungsten, or xenon arc), laser light sources, such as gas lasers, solid state crystal lasers, semiconductor diode lasers (including multiple quantum well, distributed feedback, and vertical cavity surface emitting lasers (VCSELs)), dye lasers, metallic vapor lasers, free electron lasers, and lasers using any other substance as a gain medium. Common gas lasers include Argon-ion, Krypton-ion, and mixed gas (e.g., Ar—Kr) ion lasers, emitting at 455, 458, 466, 476, 488, 496, 502, 514, and 528 nm (Ar ion); and 406, 413, 415, 468, 476, 482, 520, 531, 568, 647, and 676 nm (Kr ion). Also included in gas lasers are Helium Neon lasers emitting at 543, 594, 612, and 633 mn. Typical output lines from solid state crystal lasers include 532 nm (doubled Nd:YAG) and 408/816 nm (doubled/primary from Ti:Sapphire). Typical output lines from semiconductor diode lasers are 635, 650, 670, and 780 mm.

Excitation wavelengths and emission detection wavelengths will vary depending on the smURFP being employed, as well as other signaling molecules that may be used. In one embodiment, where the first and second signaling moieties are fluorescein and DABCYL, the excitation wavelength is 488 nm and the emission wavelength is 514 mn. In the case of semiconductor nanocrystal-based fluorescent labels, a single excitation wavelength or broadband UV source may be used to excite several probes with widely spectrally separated emission wavelengths (see Bruchez et al., 1998; Chan et al., 1998).

In one embodiment, detection of changes in the optical properties of the nucleic acid sensor molecules is performed using any of a cooled CCD camera, a cooled intensified CCD camera, a single-photon-counting detector (e.g., PMT or APD), or other light sensitive sensor. In one embodiment, the detector is optically coupled to the nucleic acid sensor molecule through a lens system, such as in an optical microscope (e.g., a confocal microscope). In another embodiment, a fiber optic coupler is used, where the input to the optical fiber is placed in close proximity to the substrate surface of a biosensor, either above or below the substrate. In yet another embodiment, the optical fiber provides the substrate for the attachment of nucleic acid sensor molecules and the biosensor is an integral part of the optical fiber.

In some embodiments, photoacoustic imaging (optoacoustic imaging), a biomedical imaging modality based on the photoacoustic effect, is employed to image the smURFPs of the present invention. In photoacoustic imaging, non-ionizing laser pulses are delivered into biological tissues (when radio frequency pulses are used, the technology is referred to as thermoacoustic imaging). In some embodiments, the photoacoustic imaging protein is a smURFP as provided herein, including in FIG. 7 and SEQ ID NO:2-14. In some embodiments, the photoacoustic imaging protein is referred to as R6-6 and has two mutations, F36L and D73G (SEQ ID NO:7). In some embodiments, R6-6 features redshifted excitation and an extremely small quantum yield. In some embodiments, these properties of R6-6 provide desirable to avoid fluorescence and produce a sound wave as part of the photoacoustic imaging methods. In some embodiments, *E. coli* expressing the R6-6 can be imaged 14-16 mm in mice bladders, which is far deeper than the imaging depth of fluorescent imaging. In some embodiments, the smURFPs can be employed for tissue imaging in vitro. In some embodiments, the smURFPs can be employed for tissue imaging in vivo.

Kits

Genetically encoded protein labeling tag: The synthesis of biliverdin analogs is fairly simple and allows for creation of molecules that can be sold as a kit or as parts for custom synthesis within a lab. The smURFPtag is necessary to target the biliverdin to specific locations within a cell and plasmids would be sold for the system.

In some embodiments, the present invention provides kits comprising a smURFP variant polypeptide as described herein. In some embodiments, any smURFP variant polypeptides, dimers, or other conjugates as described herein can be included in a kit. In some embodiments, the kit further comprises instructions for use.

EXEMPLARY EMBODIMENTS

The present invention provides polypeptides comprising an amino acid selected from the group consisting of the smURFP amino acid sequences recited in FIG. 7.

The present invention provides smURFP variant polypeptides derived from the APCα from *Trichodesmium erythraeum* (TeAPCa) parent polypeptide, where said smURFP variant polypeptides is at least 80% identical to the TeAPCa parent polypeptide and exhibits one or more characteristics selected from the group consisting of:
  a) increased Fluorescence of smURFP variant polypeptides as compared to infrared FPs IFP1.4 and iRFP713;
  b) express efficiently with minimal toxicity;
  c) does not require a lyase to covalently attach its chromophore, wherein the chromophore is biliverdin;
  d) exhibits a wavelength longer than attainable with jellyfish- or coral-derived FPs using smURFP and IFP2.0;
  e) allows for functional fusion to hCdt1(30/120) as compared to jellyfish- or coral-derived FPs mAG, eGFP, and mRFP1 which are nonfunctional; and
  f) exhibits an emission maximum in the range of 650 nm to 672 nm.

In some embodiments, the smURFP variant polypeptide is part of a dimer comprising two smURFP variant polypeptides conjugated by a linker.

In some embodiments, the linker is an amino-acid linker.

In some embodiments, the amino-acid linker comprises 23 amino acids.

In some embodiments, the smURFP variant polypeptide is part of a dimer comprising one smURFP variant polypeptide conjugated to second fluorescent protein by a linker.

In some embodiments, the said linker is an amino-acid linker.

In some embodiments, the amino-acid linker comprises 23 amino acids.

In some embodiments, the second fluorescent protein is selected from the group consisting of eGFP, mCherry, mCardinal, IFP1.4, IFP2.0, and iRFP713.

In some embodiments, the smURFP variant polypeptide comprises an amino acid substitution at one or more positions selected from the group consisting of 4, 9, 15, 18, 33, 36, 42, 45, 48, 56, 57, 59, 61, 65, 66, 73, 82, 83, 96, 98, 113, 118, 129, and 131. In some embodiments, the smURFP comprises amino acid substitutions at 1, 2, 3, 4, 5, 6, 7, 8, 9, 10, 11, 12, 13, 14, 15, 16, 17, 18, 19, 20, 21, 22, 23, or 24 positions. In some embodiments, the smURFP variant polypeptide comprises one or more substitutions selected from the group consisting of G4C, G4S, K9N, S15T, E18K, R33H, F36L, N42I, G45S, E48D, Y56H, G57R, Y59F, R61H, Y65F, G66C, D73G, G82S, V83I, G96A, V98M, D113E, K118N, Q129K, M131I, as described in FIG. 7.

In some embodiments, the smURFP variant polypeptide comprises the consensus sequence, as described in FIG. 7.

In some embodiments, the smURFP variant polypeptide comprises the amino acids from the consensus sequence at positions 4, 9, 15, 18, 33, 36, 42, 45, 48, 56, 57, 59, 61, 65, 66, 73, 82, 83, 96, 98, 113, 118, 129, 131, as described in FIG. 7.

In some embodiments, the smURFP variant polypeptide is at least 85% identical to the TeAPCa parent polypeptide.

In some embodiments, the smURFP variant polypeptide is at least 90% identical to the TeAPCa parent polypeptide.

In some embodiments, the smURFP variant polypeptide is at least 95% identical to the TeAPCa parent polypeptide.

In some embodiments, the smURFP variant polypeptide is 98% identical to the TeAPCa parent polypeptide.

In some embodiments, the smURFP variant polypeptide is selected from the group consisting of R5-2, R6-6, R7-7, R8-8, and R8-9, wherein:
  R5-2: two mutations, G4C and Y56H (SEQ ID NO:6);
  R6-6: two mutations, F36L and D73G (SEQ ID NO:7);
  R7-7: three mutations, E18K, R33H, and M131I (SEQ ID NO:8).
  R8-8: three mutations, E48D, G96A, and K118N (SEQ ID NO:9), and
  R8-9 contained three mutations, K9N, H33R, and G96D (SEQ ID NO:10).

In some embodiments, the smURFP variant polypeptide is R6-6 (SEQ ID NO:7), which comprises two mutations, F36L and D73G.

In some embodiments, the invention provides a nucleic acid encoding the smURFP.

In some embodiments, the invention provides an expression vector comprising the nucleic acid encoding the smURFP variant polypeptide.

In some embodiments, the invention provides a host cell comprising the nucleic acid encoding the smURFP variant polypeptide.

In some embodiments, the invention provides a host cell comprising the expression vector comprising the nucleic acid encoding the smURFP variant polypeptide.

In some embodiments, the invention provides a method of producing a smURFP variant polypeptide comprising: a) culturing a host cell comprising the nucleic acid encoding the smURFP variant polypeptide under conditions wherein said polypeptide is produced; and b) purifying said smURFP variant polypeptide.

In some embodiments, the invention provides a biosensor comprising a smURFP variant polypeptide as described herein.

In some embodiments, the biosensor comprises a smURFP variant polypeptide conjugated to hCdt1(30/120), hGem(1/110) or a fragment thereof.

EXAMPLES

Example 1: Generation Allophycocyanin A-Subunit Evolved Labeling Proteins

The invention described herein features the evolution of fluorescent proteins, photoacoustic imaging protein, and a genetically encoded protein labeling tag from the allophycocyanin a subunit, a phycobiliprotein from the cyanobacteria, *Trichodesmium erythraeum*.

Fluorescent proteins include smURFP, which fills a spectral gap in current fluorescent proteins and is the brightest far-red/near-infrared fluorescent protein available. A tandem dimer smURFP (TDsmURFP) was created with a 23 amino acid linker. SmURFP contains 20 mutations that were evolved after 12 rounds over the course of ~1 year and TeAPCa FPs predecessors were characterized. SmURFP fluorescence is detectable in many mammalian cell lines in culture and in living mice. All smURFP fusions show correct cellular localization in living cells. A farred/near-infrared fluorescent ubiquitination based cell cycle indicator (FUCCI) was created using smURFP and the bacteriophytochrome, IFP2.0 (created by X. Shu laboratory).

Far-red/near-infrared fluorescent ubiquitination-based cell cycle indicator (FUCCI): The far-red/near-infrared FUCCI emits either far-red or near-infrared fluorescence based on the phase of the cell cycle.

Photoacoustic imaging (optoacoustic imaging) is a biomedical imaging modality based on the photoacoustic effect. In photoacoustic imaging, non-ionizing laser pulses are delivered into biological tissues (when radio frequency pulses are used, the technology is referred to as thermoacoustic imaging). A photoacoustic imaging protein was created from smURFP, which is caused by 2 amino acids mutations (Cys52Ala and Ala96Cys mutations). This mutant was named Dark smURFP and features redshifted excitation and an extremely small quantum yield (desirable to avoid fluorescence and produce a sound wave. *E. coli* expressing the Dark smURFP can be imaged 14-16 mm in mice bladders, which is far deeper than the imaging depth of fluorescent imaging.

SmURFP has an enlarged chromophore binding site and allows for covalent attachment of a hydrophobic biliverdin analog, biliverdin dimethyl ester. For the protein labeling tag (smURFPtag), the organic synthesis of the ligand is described to modify biliverdin with a polyethylene glycol linker and any desired small molecule, including but not limited to, organic dyes, singlet oxygen generators, alkynes/azides for click chemistry, protein ligands, etc. biliverdin (BV)-polyethylene glycol linker (PEG)-Fluorescein or Methylene Blue were successfully synthesized and purified. BV-PEG-Fluorescein can be genetically targeted to nuclei of living cells and fluorescence is only detected when bound to the smURFPtag.

The fluorescent proteins are the first of this new class of fluorescent proteins. Current fluorescent proteins have been evolved from jellyfish, coral, eel, and bacteriophytochromes. SmURFP fills a spectral gap that is inaccessible to jellyfish/coral-derived fluorescent proteins. SmURFP does not require oxygen or produce hydrogen peroxide upon chromophore formation, like jellyfish/coral-derived fluorescent proteins. SmURFP is biophysically the brightest far-red/near-infrared fluorescent protein currently available and shows brightness comparable to the jellyfish fluorescent protein, eGFP (unattainable with coral red FPs and far-red/near-infrared bacteriophytochromes). SmURFP is the most photostable fluorescent protein tested in the Tsien lab over the past 15 years by P. Steinbach and shows greater photostability than the organic dyes Cy5 and AlexaFluor647.

Far-red/near-infrared fluorescent ubiquitination-based cell cycle indicator (FUCCI): The far-red/near-infrared FUCCI emits fluorescence in a spectral region with little background signal. These wavelengths are amenable for imaging in living organisms, such as mice. The far-red/near-infrared FUCCI creates a fluorescent biosensor with wavelengths inaccessible to jellyfish or coral FPs and does not produce hydrogen peroxide. The far-red/near-infrared FUCCI is the first biosensor using two BV attaching FPs and can be used with traditional FUCCI to monitor the cell cycle of two cell types.

Photoacoustic imaging proteins have recently been shown to image deeper than fluorescent proteins in living animals. The Dark smURFP has reduced quantum yield and greater photoacoustic signal when compared to iRFP713 and mIFP. Photoacoustic imaging is detectable in bacterial colonies and bacteria injected into mice and localize to the bladder (14 mm depth). Recently, Halotag (Promega), CLIPtag (New England Biolabs), and SNAPtag (New England Biolabs) have revolutionized the small molecule labeling of proteins in vitro and in vivo. All proteins and small molecule ligands are commercially available (companies in parentheses). For all these labeling technologies, the recognition molecule only serves to covalently attach the molecule to the protein and require extensive washing to remove unbound molecules/fluorophores. The smURFPtag is an improved technology because BV acts as both a recognition molecule for covalent attachment and fluorescence is turned "on" upon covalent attachment. Additionally, BV acts as a fluorescence quencher when not bound to the smURFPtag and extensive washing of unbound BV-PEG-Fluorophore is unnecessary.

Fluorescent protein: SmURFP was engineered to autocatalytically, covalently attach biliverdin without the need of an external protein, known as a lyase. Rigidification of the biliverdin in the binding allows for fluorescence emission.

Far-red/near-infrared fluorescent ubiquitination-based cell cycle indicator (FUCCI): In FUCCI, two spectrally distinct FPs are synthesized and degraded at opposing phases of the cell cycle. Typically a green FP is made during S, G2, or M phase and degraded during late M or G1 phase, while an orange FP is made during G0 or G1 phase and destroyed at the start of S phase.

Photoacoustic imaging proteins: Dark smURFP was engineered to rotate the biliverdin out of plane, which causes a red-shifted absorbance and fluorescence and reduces the fluorescence quantum yield, which is desirable to obtain a large acoustic signal.

Genetically encoded protein labeling tag: SmURFPtag covalently attached modified biliverdin analogs. Biliverdin unbound acts as a fluorescent quencher, but once covalently attached fluorescence is turned on and shows the location of the cargo.

In cell culture, smURFP shows comparable brightness to eGFP and is brighter than mCherry, mCardinal, IFP1.4, IFP2.0, and iRFP713.

Far-red/near-infrared fluorescent ubiquitination-based cell cycle indicator (FUCCI): Is based on Photoacoustic imaging proteins: smURFP shows greater photoacoustic signal than iRFP713, mIFP, and sGPA0.2.

Fluorescent protein: SmURFP was selected manually after 12 rounds of mutagenesis and 10^6 bacterial colonies. SmURFP has been rigorously tested in many cell types and in mice. The gene has been distributed to >50 researchers on Addgene.

Photoacoustic imaging proteins: Dark smURFP has been tested in bacteria in a petri dish and in the bladder of mice by our collaborators (Robert Campbell and Roger Zemp). Robert Campbell and Roger Zemp are testing in mammalian cells at the University of Alberta.

Genetically encoded protein labeling tag: The synthesis of biliverdin analogs allows for easy attachment of dyes and molecules through a polyethyleneglycol linker. SmURFPtag works in HEK293 cells. Further characterization and comparison to existing tags is necessary.

Fluorescent protein: Far-red and near-infrared fluorescent proteins are useful for imaging cells, proteins at specific cellular locations, and imaging in living organisms. Fluorescent proteins can be used to label specific cells, such as cancer, to allow for detection in culture and in organisms. Fluorescent proteins, either a single protein or part of a FRET pair, are often used in biosensors to detect small molecules within living cells.

Far-red/near-infrared fluorescent ubiquitination-based cell cycle indicator (FUCCI): Traditional FUCCI is available from Molecular Probes and Clontech to image the cell cycle. The far-red/near-infrared FUCCI should allow imaging of the cell cycle in vivo. The far-red/near-infrared FUCCI can be used with traditional FUCCI to image the cell cycle phase in two cell types. FUCCI images alterations in cell cycle caused by pharmaceutical drugs.

Photoacoustic imaging proteins: Dark smURFP allows for greater imaging depth in mice than fluorescence. This protein could be commercialized for imaging in living organisms, including mice. Commercially available photoacoustic imaging systems are now available for mice. Genetically encoded photoacoustic imaging probes are lacking and are highly desired.

Genetically encoded protein labeling tag: The synthesis of biliverdin analogs is fairly simple and allows for creation of molecules that can be sold as a kit or as parts for custom synthesis within a lab. The smURFPtag is necessary to target the biliverdin to specific locations within a cell and plasmids would be sold for the system.

REFERENCES

Giepmans, B. N., et al. (2006) The fluorescent toolbox for assessing protein location and function. Science 312, 217224.

Tsien, R. Y. (2009) Constructing and exploiting the fluorescent protein paintbox (Nobel Lecture). Angew. Chem. Int. Ed. Engl. 48, 56125626.

Shaner, N.C., et al. (2005) A guide to choosing fluorescent proteins. Nat. Methods 2, 905909.

Tsien, R. Y. (1998) The green fluorescent protein. Annu. Rev. Biochem. 67, 509544.

Shaner, N.C., et al. (2004) Improved monomeric red, orange and yellow fluorescent proteins derived from *Discosoma* sp. red fluorescent protein. Nat. Biotechnol. 22, 15671572.

Kumagai, A., et al. (2013) A bilirubininducible fluorescent protein from eel muscle. Cell 153, 16021611.

Miyawaki, A. (2011) Development of probes for cellular functions using fluorescent proteins and fluorescence resonance energy transfer. Annu. Rev. Biochem. 80, 357373.

Shu, X., et al. (2009) Mammalian expression of infrared fluorescent proteins engineered from a bacterial phytochrome. Science 324, 804807.

Yu, D., et al. (2014) An improved monomeric infrared fluorescent protein for neuronal and tumour brain imaging. Nat. Commun. 5, 3626.

Yu, D., et al. (2015) A naturally monomeric infrared fluorescent protein for protein labeling in vivo. Nat Methods 12, 763765.

Yu, D., et al. (2016) Rational design of a monomeric and photostable far-red fluorescent protein for fluorescence imaging in vivo. Protein Sci 25, 308315.

Filonov, G. S., et al. (2011) Bright and stable near-infrared fluorescent protein for in vivo imaging. Nat. Biotechnol. 29, 757761.

Filonov, G. S., et al. (2012) Deep-tissue photoacoustic tomography of a genetically encoded near-infrared fluorescent probe. Angew. Chem. Int. Ed. Engl. 51, 14481451.

Filonov, G. S., et al. (2013) A near-infrared BiFC reporter for in vivo imaging of protein-protein interactions. Chem. Biol. 20, 10781086.

Shcherbakova, D. M., et al. (2013) Near-infrared fluorescent proteins for multicolor in vivo imaging. Nat. Methods 10, 751754.

Rumyantsev, K. A., et al. (2015) Minimal domain of bacterial phytochrome required for chromophore binding and fluorescence. Sci. Rep. 5, 18348.

Shcherbakova, D. M., et al. (2015) Molecular basis of spectral diversity in nearinfrared phytochrome-based fluorescent proteins. Chem. Biol. 22, 15401551.

Sakaue-Sawano, A., et al. (2008) Visualizing spatiotemporal dynamics of multicellular cell-cycle progression. Cell 132, 487498.

Sakaue-Sawano, A., et al. (2011) Drug-induced cell cycle modulation leading to cell-cycle arrest, nuclear missegregation, or endoreplication. BMC Cell Biol. 12, 2.

Tomura, M., et al. (2013) Contrasting quiescent G0 phase with mitotic cell cycling in the mouse immune system. PLoS One 8, e73801. Photoacoustic imaging probes:

Filonov, G. S., et al. (2012b) Deeptissue photoacoustic tomography of a genetically encoded nearinfrared fluorescent probe. Angew Chem Int Ed Engl 51, 14481451.

Krumholz, A., et al. (2014) Multicontrast photoacoustic in vivo imaging using nearinfrared fluorescent proteins. Sci Rep 4, 3939.

Li, Y., et al. (2016) Engineering Dark Chromoprotein Reporters for Photoacoustic Microscopy and FRET Imaging. Sci Rep 6, 22129.

Weber, J., et al. (2016) Contrast agents for molecular photoacoustic imaging. Nat Methods 13, 639650.

Yao, J., et al. (2016) Multiscale photoacoustic tomography using reversibly switchable bacterial phytochrome as a nearinfrared photochromic probe. Nat Methods 13, 6773.

Keppler, A., et al. (2003) A general method for the covalent labeling of fusion proteins with small molecules in vivo. Nat. Biotechnol. 21, 8689.

Los, G. V., et al. (2007) The HaloTag: a novel technology for cell imaging and protein analysis. Methods Mol. Biol. 356, 195208.

Gautier, A., et al. (2008) An engineered protein tag for multiprotein labeling in living cells. Chem. Biol. 15, 128136.

Los, G. V., et al. (2008) HaloTag: a novel protein labeling technology for cell imaging and protein analysis. ACS Chem. Biol. 3, 373382.

Example 2: A Far-Red Fluorescent Protein Evolved from a Cyanobacterial Phycobiliprotein Far-red fluorescent proteins (FPs) are desirable for in vivo imaging because with these molecules less light is scattered, absorbed, or re-emitted by endogenous biomolecules compared with cyan, green, yellow, and orange FPs. We developed a new class of FP from an allophycocyanin α-subunit (APCα). Native APC requires a lyase to incorporate phycocyanobilin. The evolved FP, which we named small ultra-red FP (smURFP), covalently attaches a biliverdin (BV) chromophore without a lyase, and has 642/670-nm excitation-emission peaks, a large extinction coefficient (180,000 $M^{-1}cm^{-1}$) and quantum yield (18%), and photostability comparable to that of eGFP. smURFP has significantly greater BV incorporation rate and protein stability than the bacteriophytochrome (BPH) FPs. Moreover, BV supply is limited by membrane permeability, and smURFPs (but not BPH FPs) can incorporate a more membrane-permeant BV analog, making smURFP fluorescence comparable to that of FPs from jellyfish or coral. A far-red and near-infrared fluorescent cell cycle indicator was created with smURFP and a BPH FP.

Fluorescent proteins (FPs) enable tracking of gene expression, cell fate, and fusion proteins[1-4]. FPs from jellyfish or coral are spectrally limited to excitation maxima <610 nm, and they require oxygen for, and produce hydrogen peroxide upon, chromophore formation, thus requiring an aerobic environment tolerant of reactive oxygen species[5]. Chromophore formation may take hours[5], and mixtures of green and red fluorescence are common[6-8]. $H_2O_2$ is a mediator of cell survival, growth, differentiation, and implicated in diseases[9-12], which could complicate experimental results. Thus, FPs that use endogenous chromophores to eliminate oxygen necessityl[3] and hydrogen peroxide production are desirable. Far-red (FR) and near-infrared (NIR) FPs are desirable for imaging in living animals because these wavelengths minimize light scattering and absorbance by endogenous biomolecules and so reduce autofluorescence[14].NIR FPs were engineered from non-fluorescent BPHs that attach biliverdin but have low quantum yield (QY) and protein stability[15-20].

We started with the light-harvesting phycobiliproteins from cyanobacteria (APCα from *Trichodesmium erythraeum* (TeAPCα)). Native APC is a highly fluorescent hexamer (three α+β dimers) that uses an auxiliary protein known as a lyase to incorporate phycocyanobilin (PCB, FIG. 1a-c)[21]. Native APC biliprotein FPs have been created, but these FPs require a lyase, use PCB, and are expressed only in *Escherichia coli*[22,23]. In our approach, we first evolved TeAPCα mutants to autocatalytically attach PCB (without a lyase) and fluoresce. Second, since PCB is not present in mammals, we evolved derivatives that bind BV (FIG. 1c), a molecule ubiquitous in eukaryotes and produced at the rate of 300-500 mg per din humans[24]. After 12 rounds of mutating and screening ~$10^6$ bacterial colonies, an FP with 20 mutations was selected and named smURFP (homodimer-lacking chromophore, FIG. 1d).

Engineering and characterization of APCαFPs

We chose TeAPCα (15 kD) because it lacked 29 amino acids common to other APCαs (FIG. 6). Expression of TeAPCα with heme oxygenase-1 (HO-1) and phycocyanobilin-ferredoxin oxidoreductase (PcyA) for PCB production showed no fluorescence (FIG. 2a). Round 1 (R1) of mutagenesis created an FP that covalently attached PCB (R1+PCB) and was fluorescent (FIG. 7a) with one mutation, N42I. Round 2 produced an FP (R2-1+PCB) that was 27-fold brighter than R1+PCB and had two mutations, Y65F and G66C, in the homodimeric interface. Round 3 produced R3-2+PCB, with two mutations, V83I and V98M, and 1.7-fold brighter than R2-1+PCB (FIG. 7b). R2-1+PCB and R3-2+PCB had QYs of 7.2% and 13% and extinction coefficients (ECs) of 65,000 and 74,000 $M^{-1}cm^{-1}$, respectively, showing increased brightness (EC×QY) correlated with biophysical properties.

After PCB selections, the PcyA gene was removed, leaving only BV production. R2-1 and R3-2 lacked fluorescence with BV. Round 4 produced an FP that covalently attached BV and had red-shifted fluorescence (R4-1; lack of PCB signifies BV). R4-1 contained four mutations, of which three (G45S, R61H, and Q129K) are necessary for BV covalent attachment. Round 5 selected R5-2 with two mutations, G4C and Y56H, which red-shifted both excitation and emission by ~49 nm (Table 4) relative to R3-2+PCB, illustrating the malleability of wavelengths. R4-1 and R5-2 had QYs of 9.0% and 5.3% and ECs of 93,000 and 71,000, respectively, showing diminished QY with red-shifted fluorescence.

TABLE 4

Characteristics of evolved APCα FPs.

| Fluorescent Protein | Excitation Maximum (nm) | Emission Maximum (nm) | Extinction Coefficient ($M^{-1} cm^{-1}$) | Quantum Yield (%) | Net Charge[a] | Molecular Brightnes Relative to smURFP (%) |
|---|---|---|---|---|---|---|
| TeAPCα | NA | NA | NA | NA | −2.1 | NA |
| R + PCB | ND | ND | ND | ND | −2.1 | ND |
| R2-1 + PCB | 626 | 648 | 65,000 | 7.2 | −2.1 | 14 |
| R3-2 + PCB | 620 | 648 | 74,000 | 13 | −2.1 | 30 |
| R4-1 | 647 | 674 | 93,000 | 9.0 | −1 | 26 |
| R5-2 | 671 | 696 | 71,000 | 5.3 | −1 | 12 |
| R6-6 | 648 | 676 | 190,000 | 9.6 | −2.1 | 56 |

TABLE 4-continued

Characteristics of evolved APCα FPs.

| Fluorescent Protein | Excitation Maximum (nm) | Emission Maximum (nm) | Extinction Coefficient (M$^{-1}$ cm$^{-1}$) | Quantum Yield (%) | Net Charge[a] | Molecular Brightnes Relative to smURFP (%) |
|---|---|---|---|---|---|---|
| R7-7 | 648 | 676 | 250,000 | 16 | 0 | 123 |
| R8-8 | 648 | 672 | 260,000 | 13 | −1 | 104 |
| R8-9 | 644 | 672 | 175,000 | 12 | −1.1 | 65 |
| R10-10 | 646 | 672 | 200,000 | 15 | −2 | 93 |
| R11-2 | 642 | 672 | 190,000 | 12 | −2 | 70 |
| smURFP | 642 | 670 | 180,000 | 18 | −1.9 | 100 |

NA, not applicable; ND, not determined.
FPs named as in FIG. 7.
[a]Calculated using Innovagen protein calculator.

At round 6, the selection was altered to create blue-shifted APCαFPs+BV, and 5-10 bright colonies per plate were selected, mixed, grown in lysogeny broth (LB), and the mixture of DNA was purified and retransformed to evolve FPs that grew faster in *E. coli*. R6-6 was selected with 650-nm excitation to blue-shifted fluorescence. R6-6 had two mutations, F36L and D73G, and had a QY of 9.6% and EC of 190,000; these values were improved relative to R5-2. R7-7 contained three mutations (E18K, R33H, and M131I). R8-8 and R8-9 contained three mutations (E48D, G96A, and K118N; and K9N, H33R, and G96D, respectively). E48D and G96A/D are located near BV, while K9N, H33R, and K118N alter surface charge. R8-8 and R8-9 had QYs of 13% and 12% and ECs of 260,000 and 175,000, respectively, which should have been less fluorescent than R7-7 (QY of 16%, EC of 250,000). R7-7, R8-8, and R8-9 were, respectively, 1.3-, 5.8-, and 5.7-fold brighter than R4-1 (FIG. 7c). Clearly, fluorescence brightness is not strictly limited to QY×EC and is dependent on protein production and stability, which differ despite having the same *E. coli*, arabinose, plasmid, promoter, amino acid length, number of bacteria (OD$_{600}$), media, propagation temperature, and growth time. Round 9 FPs were not brighter than round 8 FPs, so 20 clones were randomly mutagenized. R10-10 was 8.3-fold brighter than R4-1 and contained S15T, R33H, and G96A mutations. R10-10 had a QY of 15% and an EC of 200,000, which were comparable to R7-7 (QY of 16% and EC of 250,000), but R10-10 and R7-7 were 8.3- and 1.3-fold, respectively, brighter than R4-1 (FIG. 7d). R11-2 was slightly more fluorescent than R10-10 (FIG. 7e) but showed no improvement in biophysical properties. R10-10 and the round 11 library were mutated for the twelfth, final selection, yielding smURFP with two mutations Y59F and G82S, and C4S-removed disulfide bond formation. APCαFPs are aligned in FIG. 7f. smURFP is ~650-fold brighter than R1+PCB. BV (QY of 0.013%) shows extremely weak fluorescence, but after covalent attachment to smURFP (QY of 18%), the QY is increased ~1,400-fold because of BV rigidification and has spectral properties similar to Cy5 (FIG. 2a,b; full absorbance in FIG. 8a.

Characterization of smURFP and Tandem Dimer smURFP smURFP was compared to BPH FPs with identical growth conditions in *E. coli*. Fluorescence of smURFP is greater than that of infrared FPs IFP1.4 and iRFP713 (FIG. 2c). Mass spectrometry (MS) revealed that BV attachment to APCαFPs and smURFPs is limited, and the predominant fluorescent species has one BV (FIG. 8).

smURFP ran as a 32-kD homodimer on a native gel. R10-10 ran as a 32-kD homodimer, while R4-1 was a tetramer (FIG. 9a). Tandem dimer smURFP (TDsmURFP) was created by adding a 23-amino-acid linker between subunits and had ~70% fluorescence of smURFP in bacteria (FIG. 2c). TDsmURFP (33 kD) ran near smURFP. tdTomato (54 kD) and IFP1.4 (37 kD) confirmed the dimeric nature of smURFP (FIG. 9a,b). To confirm covalent BV attachment, the FPs were run on a denaturing gel, and BV was detected with zinc[25]. IFP1.4, smURFP, and TDsmURFP showed correct molecular weight (MW), with BV covalently attached (FIG. 9c). C52 is evolutionarily conserved among all APCαs and covalently attaches PCB (FIGS. 6 and 10a). The C52S mutation eliminated smURFP fluorescence (FIG. 10b,c), and C52 remains the BV attachment site. The large EC of smURFP, 180,000 M$^{-1}$cm$^{-1}$ per BV chromophore, and its relatively large QY of 18% make smURFP biophysically as bright as eGFP. BPH FPs have low QYs and are dimmer than smURFPs (Table 5).

Table 5: Biophysical properties of FPs and Cy5. Photostability, time to bleach 50% from an initial emission rate of 1,000 photons per s. NA, not applicable. [a]Determined as described in ref 3. [b]Determined as described in Online Methods. [c]Data from ref 3. [d]Data from ref. 29. [e]Data from ref 17. [f]Data from ref 15. [g]Data from ref. 16. [h]Data from ref 18.

TABLE 5

Biophysical properties of FPs and Cy5

| Fluorescent molecule | excitation maximum (nm) | emission maximum (nm) | extinction coefficient (m$^{-1}$cm$^{-1}$/ chromophore) | Quantum yield (%) | In vitro photo-stability t$_{50\%}$ (s)[a] | mammalian cell photo-stability t$_{50\%}$ (s)[a] | stoichiometry | chromophore maturation or attachment t$_{50\%}$ (min) | Protein stability t$_{50\%}$ (h)[b] | molecular brightness relative to eGFP (%) |
|---|---|---|---|---|---|---|---|---|---|---|
| eGFP | 488[c] | 507[c] | 56,000[c] | 60[c] | 110[c] | 560 | Monomer | 25[c] | 21 | 100 |
| mCherry | 587[c] | 610[c] | 72,000[c] | 22[c] | 96[c] | 89 | Monomer | 15[c] | | 47 |
| mCardinal | 604[d] | 659[d] | 87,000[d] | 19[d] | 730[d] | | Monomer | 27[d] | | 49 |
| smURFP + BV | 642 | 670 | 180,000 | 18 | 300 | 570 | Dimer | 39 | 33 | 96 |

TABLE 5-continued

Biophysical properties of FPs and Cy5

| Fluorescent molecule | excitation maximum (nm) | emission maximum (nm) | extinction coefficient (m$^{-1}$cm$^{-1}$/ chromophore) | Quantum yield (%) | In vitro photo-stability $t_{50\%}$ (s)$^a$ | mammalian cell photo-stability $t_{50\%}$ (s)$^a$ | stoichiometry | chromophore maturation or attachment $t_{50\%}$ (min) | Protein stability $t_{50\%}$ (h)$^b$ | molecular brightness relative to eGFP (%) |
|---|---|---|---|---|---|---|---|---|---|---|
| smURFP + BVMe$_2$ | 646 | 672 | 65,000 | 12 | | 340 | Dimer | | 35 | 23 |
| TDsmURFP + BV | 642 | 670 | 170,000 | 18 | 190 | | Tandem dimer | | | 91 |
| iRFP670 | 643$^e$ | 670$^e$ | 114,000$^e$ | 11$^e$ | | 290$^e$ | Dimer | | | 37 |
| Cy5 | 649 | 670 | 250,000 | 25 | 22 | | NA | | NA | 186 |
| IFP1.4 | 684$^f$ | 708$^f$ | 92,000$^f$ | 7$^f$ | 8.4$^f$ | 70$^e$, 50$^g$ | Weak dimer | 114$^g$ | 4.4$^g$ | 19 |
| IFP2.0 | 690$^h$ | 711$^h$ | 86,000$^h$ | 8$^h$ | | | Weak dimer | | | 20 |
| iRFP713 | 690$^g$ | 713$^g$ | 98,000$^g$ | 6.3$^e$, 5.9$^g$ | | 960$^e$, 450$^g$ | Dimer | 168$^g$ | ~4.4$^g$ | 18 |

MS showed that APCαFPs contain <1 BV per dimer when expressed with HO-1 in bacteria (FIG. 8). BV incorporation rate was measured in order to determine whether this was due to lack of BV and/or to smURFP's affinity for BV. smURFP fluorescence requires BV binding and covalent attachment. 0.5 μM smURFP (1 μM empty chromophoresites) was mixed with 0.1, 1, or 10 μM BV (FIG. 11). Fluorescence approached its asymptotic level as an exponential growth in time with a half-life ~39 min, independent of BV concentration, consistent with smURFP+BV forming a nonfluorescent high-affinity complex before development of fluorescence and covalent attachment to BV. Two-step kinetics are typical for phycobiliproteins and phytochromes[26,27]. Increasing pH increases C52 nucleophilicity and the rate of fluorescence development (Table 6). The low stoichiometry of BV relative to smURFP reflected limiting levels of BV during protein expression.

TABLE 6

SmURFP incorporation rates of BV. Data fit to 1$^{st}$ order increase in fluorescence: F = A [1 − exp$^{-kt}$]. Avg., average; Conc., concentrations; $t_{50\%}$, time to reach 50% maximal fluorescence intensity.

Figure 12:
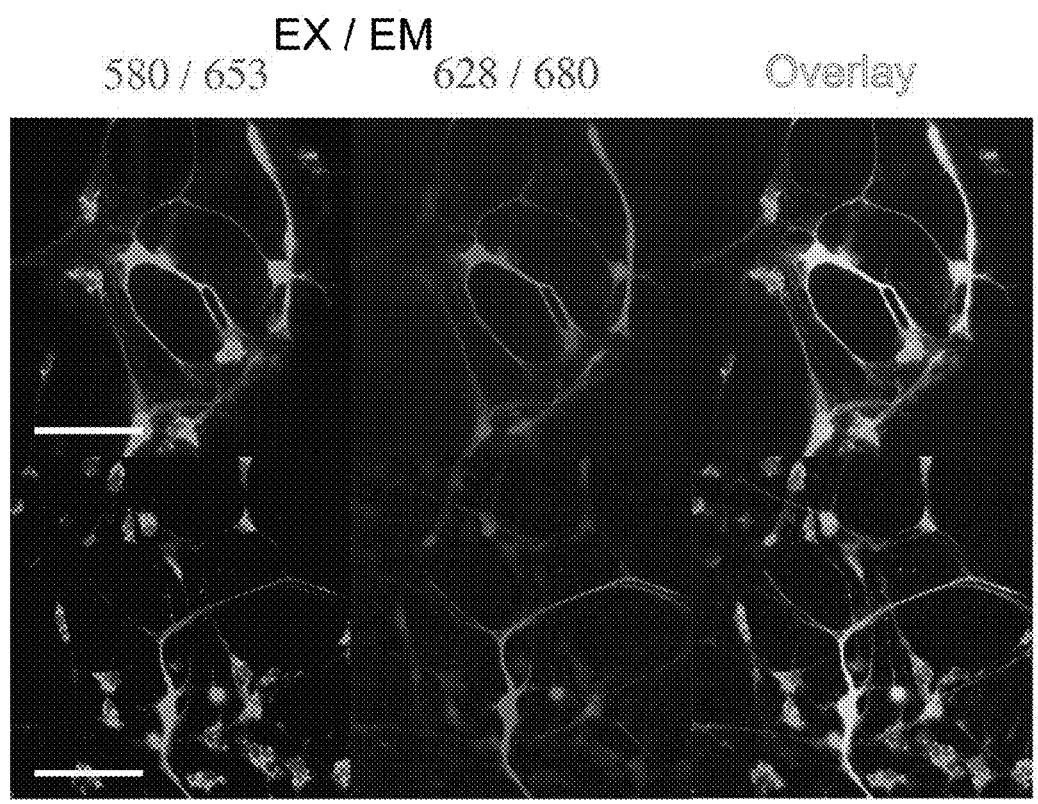
FIG. 12: Rat primary neuronal cultures transduced with smURFP T2A mCherry lentivirus. Representative neuronal culture images (32 images, ~160 neurons) 15 d after transduction and incubated with 25 µM BV for 10 min. Exposure time=30 ms and 100 ms for EX/EM of 580/653 nm and 628/680 nm, respectively. Overlay shows extensive aggregation of mCherry in lysosomes relative to smURFP. EX is excitation maximum and EM is emission maximum. Scale bar=100 µm.

| 0.5 μM smURFP in | A | k(min$^{-1}$) | R | T$_{50\%}$(min) |
|---|---|---|---|---|
| PBS, + 0.1 μM BV | 1.1 | 0.024 | 1.0 | 29 |
| PBS, + 1 μM BV | 1.1 | 0.015 | 1.0 | 46 |
| PBS, + 10 μM BV | 1.1 | 0.015 | 1.0 | 46 |
| PBS, + 0.1 μM BV (pH 8) | 1.1 | 0.029 | 0.97 | 24 |
| PBS, + 1 μM BV (pH 8) | 1.1 | 0.029 | 0.99 | 24 |
| PBS, + 10 μM BV (pH 8) | 1.1 | 0.032 | 0.99 | 22 |
| PBS, + 0.1 μM BV + 1 mM DTT | 1.1 | 0.012 | 1.0 | 58 |
| PBS, + 1 μM BV + 1 mM DTT | 1.1 | 0.011 | 1.0 | 63 |
| PBS, + 10 μM BV + 1 mM DTT | 1.1 | 0.015 | 1.0 | 46 |
| PBS + 20% FBS, + 0.1 μM BV | 1.1 | 0.016 | 1.0 | 43 |
| PBS + 20% FBS, + 1 μM BV | 1.1 | 0.012 | 1.0 | 58 |
| PBS + 20% FBS, + 10 μM BV | 1.1 | 0.015 | 1.0 | 46 |
| PBS + 20% FBS, + 0.1 μM BV (pH 9.4) | 0.95 | 0.097 | 0.91 | 7.1 |
| PBS + 20% FBS, + 1 μM BV (pH 9.4) | 0.99 | 0.043 | 0.99 | 16 |
| PBS + 20% FBS, + 10 μM BV (pH 9.4) | 0.99 | 0.063 | 1.0 | 11 |
| PBS + 20% FBS, + 0.1 μM BV + 1 mM DTT | 0.95 | 0.023 | 0.99 | 30 |
| PBS + 20% FBS, + 1 μM BV + 1 mM DTT | 0.95 | 0.022 | 0.99 | 32 |
| PBS + 20% FBS, + 10 μM BV + 1 mM DTT | 0.96 | 0.043 | 1.0 | 16 |
| PBS, Avg. 3 Conc. | 1.0 | 0.018 | 0.99 | 39 |
| PBS, Avg. 3 Conc. (pH 8) | 1.1 | 0.030 | 0.99 | 2 |
| PBS, Avg. 3 Conc. + 1 mM DTT | 1.1 | 0.013 | 1.0 | 53 |
| PBS + 20% FBS, Avg. 3 Conc. | 1.1 | 0.014 | 1.0 | 50 |
| PBS + 20% FBS, Avg. 3 Conc. (pH 9.4) | 0.98 | 0.066 | 0.98 | 11 |
| PBS + 20% FBS, Avg. 3 Conc. + 1 mM DTT | 0.95 | 0.029 | 0.99 | 24 | smURFP Expression in Neurons smURFP fluorescence was compared to that of the coral-derived red FP mCherry, because fluorescence is spectrally separate from smURFP. Lentivirus was created with smURFP-T2A-mCherry, where T2A is a self-cleaving peptide sequence that ensures production of both FPs at a similar rate. Neuronal culture showed colocalized expression of both FPs. mCherry showed lysosomal aggregation[28], which is not seen with smURFP (FIG. 12).

Figure 13A:
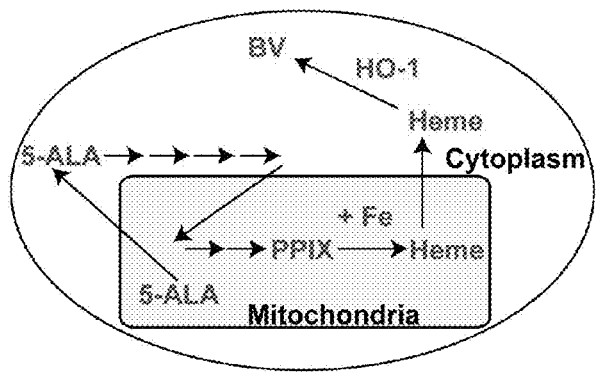
FIG. 13A-FIG. 13G: BV production by HO-1 and representative images of HO-1 experiments quantified in FIG. 3a,b. (A) Schematic illustrating BV production in cells. Precursors to BV are shown in red. Arrows indicate movement from subcellular compartments and/or intermediates in the pathway. 5-ALA production is the rate-limiting step in the formation of heme. Representative images of (B) IFP1.4 IRES eGFP/HO-1, (C) IFP2.0 IRES eGFP/HO-1, (D) iRFP713 IRES eGFP/HO-1, (E) smURFP IRES eGFP/HO-1, (F) TDsmURFP IRES eGFP/HO-1, (G) Control for HO-1 expression, non-fluorescent iRFP713 fragment (x) IRES eGFP/HO-1. (B-G) For each sample, 5 images were collected and experimental conditions are listed on top of each column. White numbers are mean fluorescence intensity (n=30). Red (left) is EX/EM=628/680 nm and yellow (right) is EX/EM=665/725 nm. Exposure time=200 ms. Scale bar=100 μm.
Figure 13B:
Figure 13C:
Figure 13D:
Figure 13E:
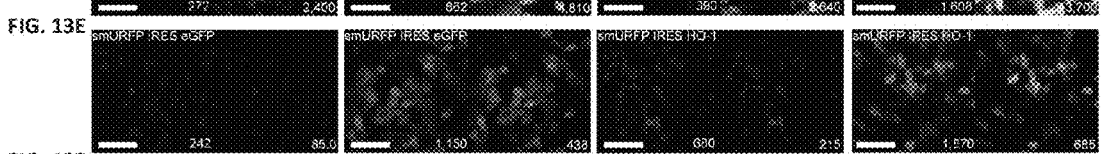
Figure 13F:
Figure 13G:
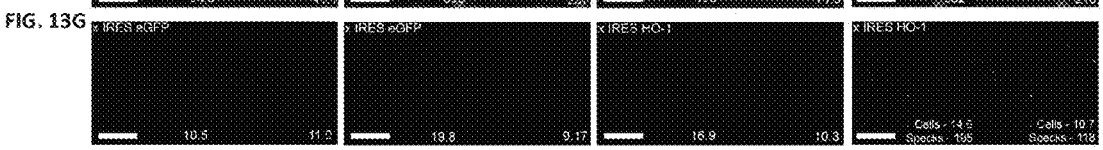
Figure 14A:
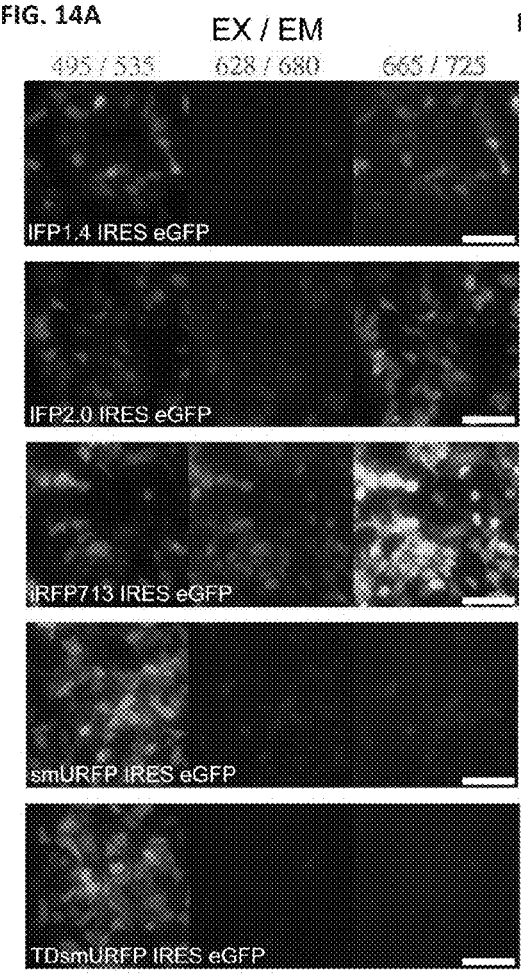
FIG. 14A-FIG. 14D: Representative images of FPs with and without exogenous chromophore addition. FPs were expressed without HO-1. Representative images used for quantitation in FIG. 3e. Five total images were taken for each sample. (A) Representative images of FPs without exogenous chromophore. EX/EM=628/680 (red) and 665/725 (yellow) nm images are brightened 4× relative to b-d to show dim fluorescent cells. FPs+25 μM BV (B), 25 μM PCB (C), or 25 μM BVMe2 (D). Incubation time of chromophore is 3 h. (A,B) Exposure=250 ms and (C,D) Exposure=50 ms. (B-D) Images are adjusted the same. Scale bar=100 μm.
Figure 14B:
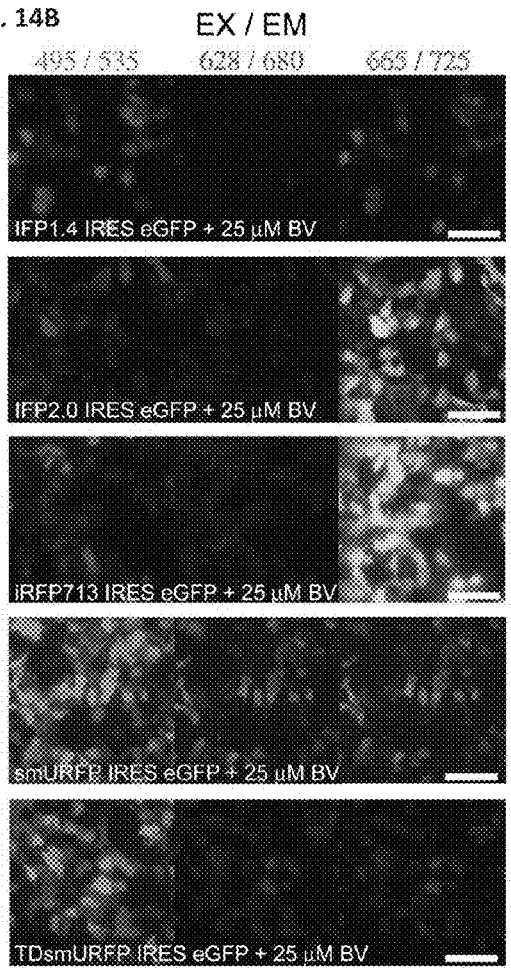
Figure 14C:
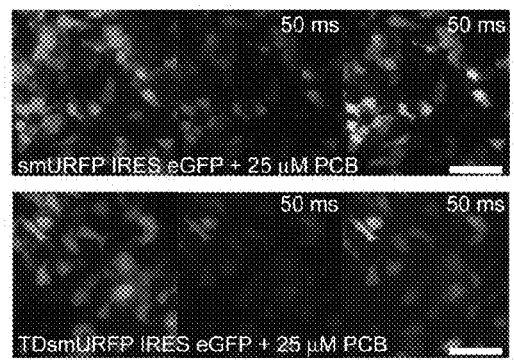
Figure 14D:
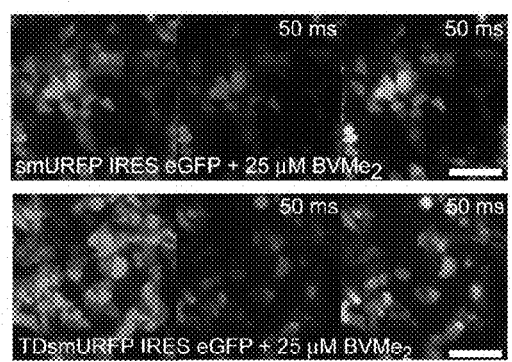

Increasing Chromophore within Mammalian Cells smURFP is better expressed than BPH FPs in bacteria (FIG. 2c). To test whether this was the case in mammalian cells, we expressed our constructs in HEK293A cells. smURFP and TDsmURFP fluorescence is less than that of eGFP in HEK293A cells. We hypothesized that BV has low membrane permeability. 3 h of 25 μM BV addition increased smURFP and TDsmURFP fluorescence by 4.7- and 6.7-fold, respectively (FIG. 3a). Purification of FP+BV in E. coli requires HO-1 to produce BV, and expression of HO-1 in mammalian cells should increase BV concentration. The production of heme is highly orchestrated (FIG. 13a). Expression of cyanobacterial HO-1 with smURFP and TDsmURFP significantly increased fluorescence 2.8- and 2.0-fold, respectively. The expression of HO-1 with 5-aminolevulinic acid (5-ALA, a precursor of heme) and iron(ii) sulfate (to reduce the accumulation of fluorescent protoporphyrin IX (PpIX)) showed significant increases in smURFP and TDsmURFP fluorescence of 7.7- and 7.0-fold, respectively (FIG. 3a). To prove that the benefit of extra BV is not limited to smURFP, we expressed HO-1 with BPH FPs. IFP1.4, IFP2.0, and iRFP713 all showed significant increases in fluorescence of 7.1-, 8.2-, and 5.7-fold, respectively, with HO-1+5-ALA+FeSO4, even though it was reported that iRFP713 does not require exogenous BV16 (FIG. 3b).

Figure 15:
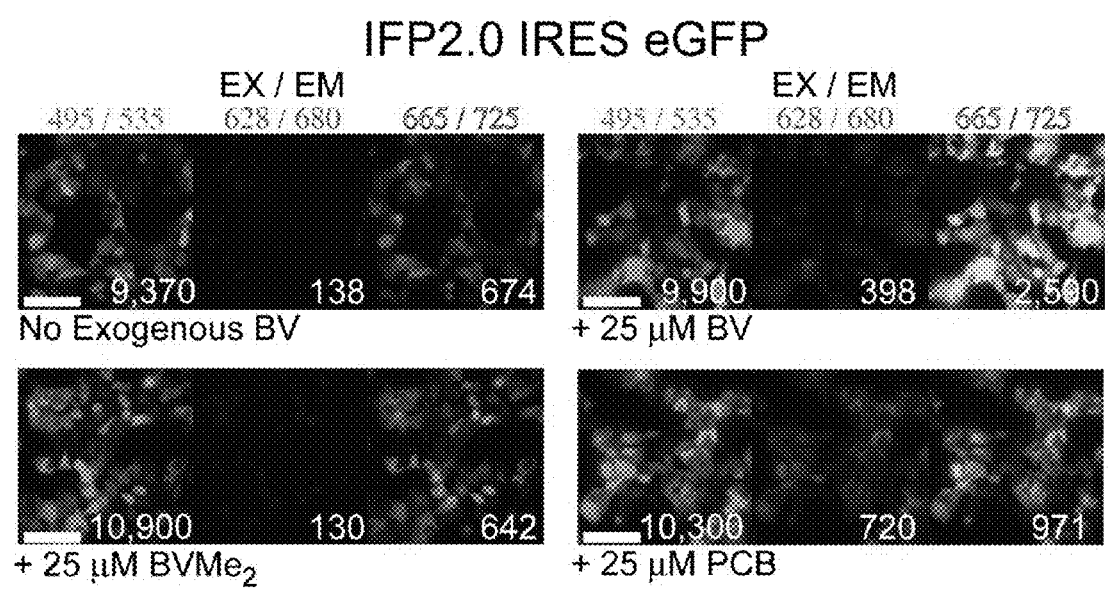
FIG. 15: IFP2.0 does not bind BVMe2 and PCB binding does not significantly increase fluorescence. IFP2.0 IRES eGFP was expressed in HEK293A cells. Chromophore was incubated for 5 h. Exposure=50 ms and 200 ms for EX/EM=495/535 nm and 628/680 and 665/725 nm, respectively. Representative fluorescent images are shown from 6 images per sample. White numbers are mean fluorescence intensity (n=30). Addition of BV to IFP2.0 causes a 3.8-fold increase in fluorescence. BVMe2 shows no increase in fluorescence relative to no exogenous BV (some BV present in fetal bovine serum). IFP2.0+PCB results in blue-shifted fluorescence that is not significantly increased (as seen with smURFP and TDsmURFP.

The more hydrophobic biliverdin dimethylester (BVMe$_2$, FIG. 1c) should have greater membrane permeability. The carboxylic acids of BV are recognition motifs and must be free for BPHs, while carboxylic groups of BV are exposed on smURFP and tolerate esterification (FIG. 3c,d). Addition of 25 µM BV for 3 h significantly increased fluorescence of BPH FPs (FIG. 3e and FIG. 14). Addition of 25 µMBVMe$_2$ or PCB (for 3 h in each case) greatly increased smURFP fluorescence—by 18- and 10-fold, respectively—relative to 25 µM BV (FIG. 3e). TDsmURFP was brightened by 4.0- and 5.8-fold with BVMe$_2$ and PCB, respectively. 25 µM PCB added to IFP2.0 blue shifted and decreased fluorescence. IFP2.0+25 µM BVMe$_2$ resulted in no fluorescence increase (FIG. 15), indicating that esterases do not remove methyl groups on BVMe$_2$ to form BV, which would enhance the fluorescence of IFP2.0. smURFP+BVMe$_2$ is 7-fold brighter than IFP2.0 or iRFP713 (FIG. 3e).

The concentration dependence of different chromophores was also analyzed (FIG. 16). PCB requires ≥40 µM for fluorescence similar to 2.5 µM BVMe$_2$. BVMe$_2$ penetrates the membrane best, reaching saturation at ≤2.5 µM. We expressed eGFP from an internal ribosomal entry site (IRES) along with smURFP expressed from the CMV promoter in the presence of BVMe$_2$. Under these conditions, eGFP expression was lower relative to smURFP, and smURFP had five-fold greater fluorescence. Based on photophysical properties, smURFP is as bright as eGFP and could be equally bright in mammalian cells with sufficient chromophore in the cytoplasm.

Figure 17A:
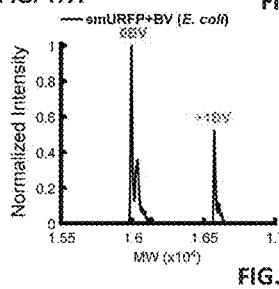
FIG. 17A-FIG. 17L: Electrospray mass spectrometry characterization of smURFP/TDsmURFP+0, 1, or 2 chromophores. SmURFP+BV (*Escherichia coli*) and TDsmURFP+BV (*Escherichia coli*) were purified with the expression of HO-1 under limited BV conditions. SmURFP and TDsmURFP without chromophore were purified lacking HO-1 from *Escherichia coli* and chromophore was added in vitro as described in the Online Methods. Samples are named after predominate fluorescent species (+1 or 2 chromophore). (A) smURFP+BV (*Escherichia coli*). Free protein: calculated=15,989 D and found=15,992 D. FP+BV: calculated=16,572 D and found=16,574 D. (B) smURFP+1BV. Free protein: calculated=15,989 D and found=16,002 D. FP+BV: calculated=16,572 D and found=16,588 D. (C) smURFP+2BV. FP+BV: calculated=16,572 D and found=16,603 D. (D) smURFP+1PCB. Free protein: calculated=15,989 D and found=16,008 D. FP+PCB: calculated=16,576 D and found=16,591 D. (E) smURFP+2PCB. FP+PCB: calculated=16,576 D and found=16,603 D. (F) smURFP+1BVMe2. MS shows FP is ionized as the homodimer+BVMe2. FP2+BVMe2: calculated=32,590 D and found=32,612 D. (G) TDsmURFP+BV (*Escherichia coli*). Free protein: calculated=32,913 D and found=32,919 D. TDFP+BV: calculated=33,495 D and found=33,505 D. TDFP+2BV: calculated=34,078 D and found=34,086 D. (H) TDsmURFP+1BV. Free protein: calculated=32,913 D and found=32,977 D. TDFP+BV: calculated=33,495 D and found=33,610 D. TDFP+2BV: calculated=34,078 D and found=34,219 D. (I) TDsmURFP+2BV. Free protein: calculated=32,913 D and found=32,993 D. TDFP+BV: calculated=33,495 D and found=33,546 D. TDFP+2BV: calculated=34,078 D and found=34,112 D. (J) TDsmURFP+1PCB. Free protein: calculated=32,913 D and found=32,921 D. TDFP+1PCB: calculated=33,499 D and found=33,505 D. (K) TDsmURFP+2PCB. TDFP+1PCB: calculated=33,499 D and found=33,549 D. TDFP+2PCB: calculated=34,086 D and found=34,097 D. (L) TDsmURFP+2BVMe2. Free protein: calculated=32,913 D and found=32,978 D. TDFP+BVMe2: calculated=33,523 D and found=33,521 D. TDFP+2BV: calculated=34,134 D and found=34,116 D. (A-L) Average mass calculated by program ProMass Deconvolution.
Figure 17B:
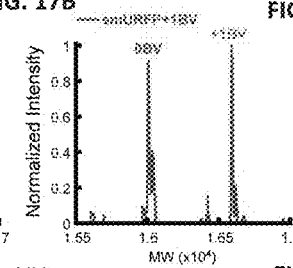
Figure 17C:
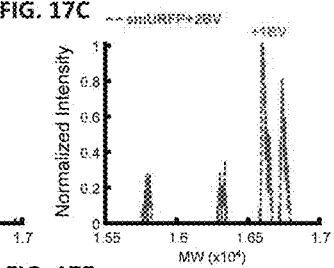
Figure 17D:
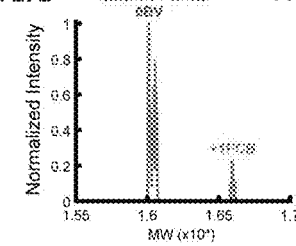
Figure 17E:
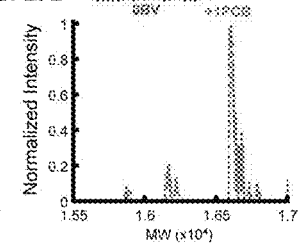
Figure 17F:
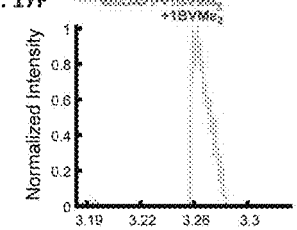
Figure 17G:
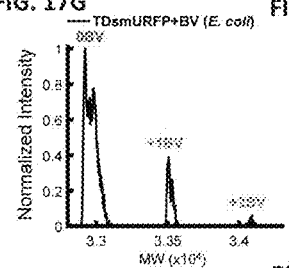
Figure 17H:
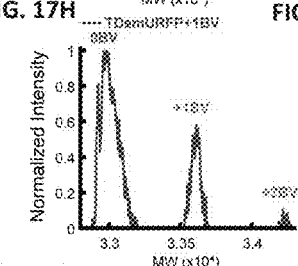
Figure 17I:
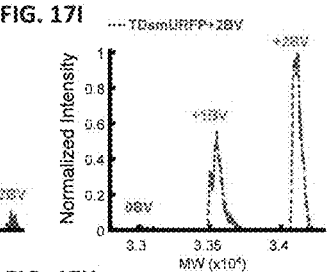
Figure 17J:
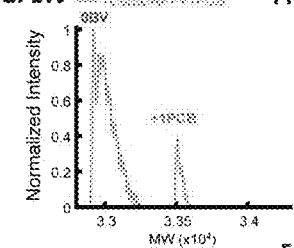
Figure 17K:
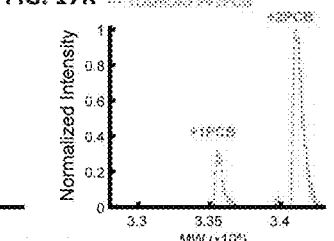
Figure 17L:
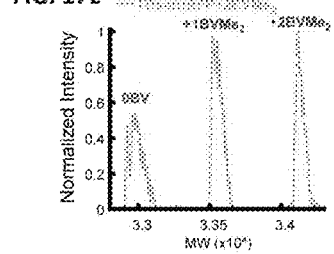
Figure 18A:
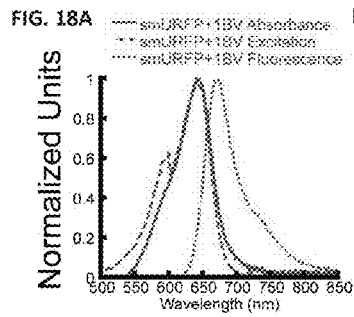
FIG. 18A-FIG. 18J: Absorbance, excitation, and fluorescence spectra of smURFP/TDsmURFP+0, 1, or 2 chromophores. Spectra were determined from samples in FIG. 17. (A-E) SmURFP and TDsmURFP+1 chromophore (BV/PCB/BVMe2). SmURFP/TDsmURFP+1BV and 1BVMe2 are identical spectrally. SmURFP/TDsmURFP+1PCB shows absorption broadening, but excitation is similar to BV/BVMe2. SmURFP/TDsmURFP+1PCB fluorescence is blue-shifted by ~6 and ~10 nm, respectively. (F-J) SmURFP and TDsmURFP+2 chromophore (BV/PCB). SmURFP/TDsmURFP+2BV are spectrally identical to 1BV, but there is ~2.4-fold reduction in QY (Table 5). SmURFP/TDsmURFP+2PCB shows a red-shifted excitation maximum (674 nm). SmURFP/TDsmURFP+2PCB fluorescence is red-shifted by 34 and 40 nm, respectively, and results in a 5.4- and 4.4-fold, respectively, reduction in QY (Table 5). SmURFP+2BVMe2 was not observed by changes in spectral properties and by MS (Table 5, FIG. 17). TDsmURFP+2BVMe2 showed no change in spectra or QY, but had reduced EC and was identified by MS (Table 5, FIG. 17).
Figure 18B:
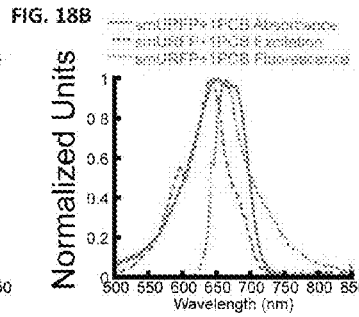
Figure 18C:
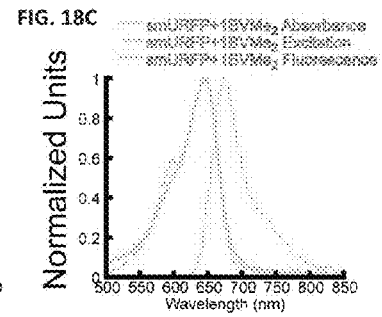
Figure 18D:
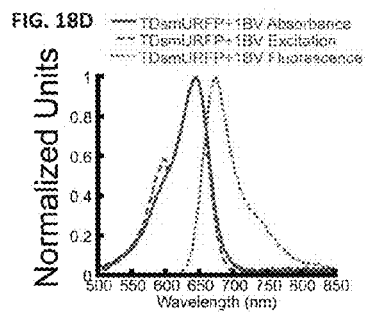
Figure 18E:
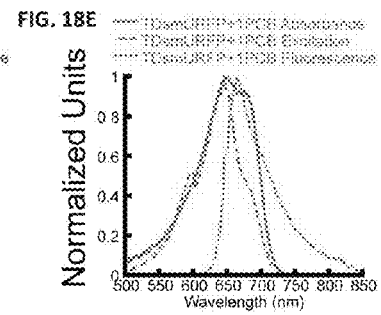
Figure 18F:
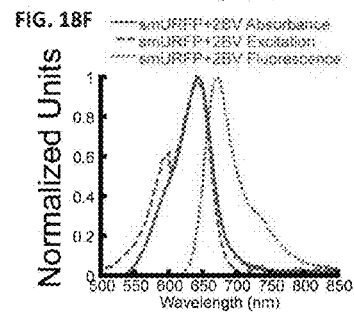
Figure 18G:
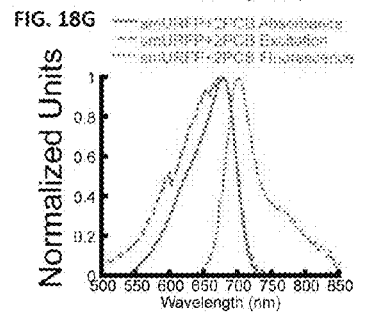
Figure 18H:
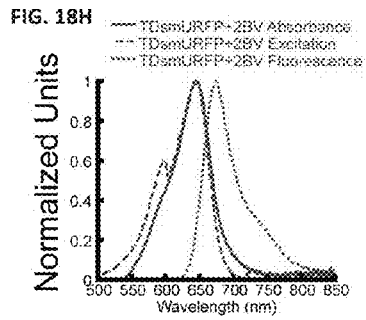
Figure 18I:
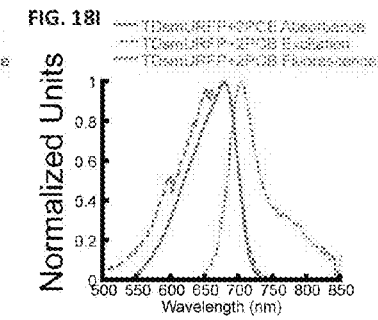
Figure 18J:
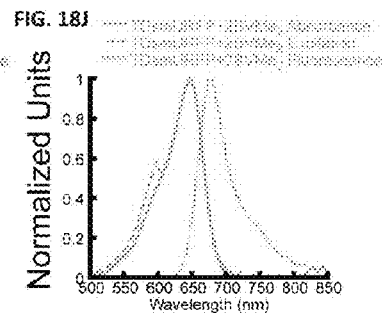
Figure 21A:
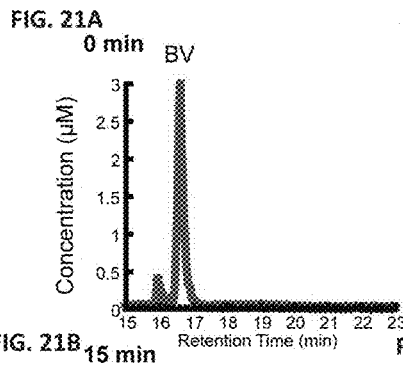
FIG. 21A-FIG. 21J: Concentration of BV or BVMe2 in plasma, in vitro. 10 µM BV or BVMe2 in plasma was incubated for 0 min at 4° C. and 15, 60, and 1,440 min at 37° C. Reactions were stopped by freezing at −80° C. (A-E) 10 µM BV and (F-II) 10 µM BVMe2 reverse phase HPLC traces showing concentration of chromophore. Concentration of BV (I) or BVMe2, BVMe, and BV (J) as a function of time. BVMe2 is rapidly cleaved by esterases and BV is significantly degraded without the liver and spleen, which converts BV to bilirubin. BV analogues will be screened in the developed, in vitro plasma assay for enhanced stability and/or lack of modification removal.
Figure 21E:
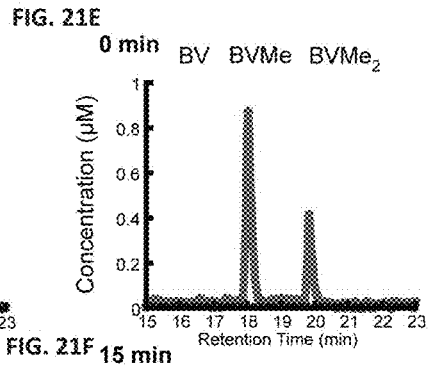
Figure 21B:
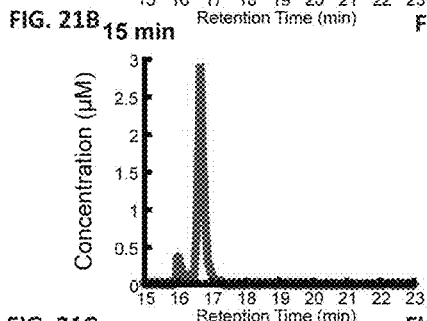
Figure 21F:
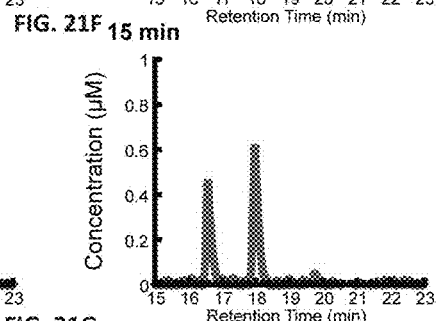
Figure 21C:
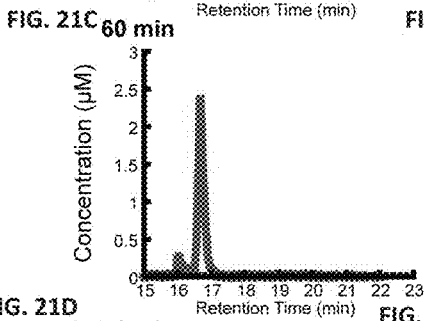
Figure 21G:
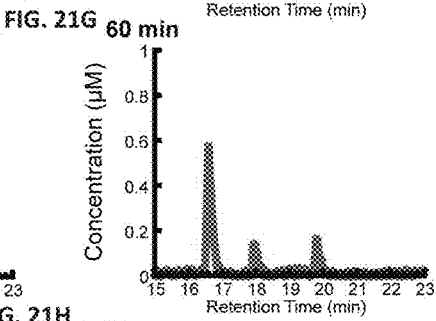
Figure 21D:
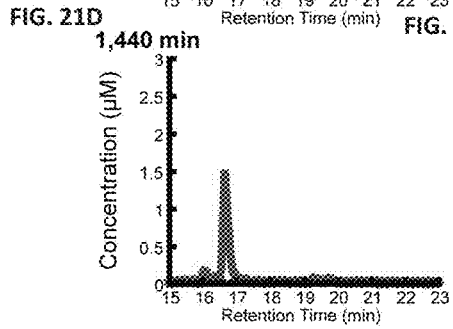
Figure 21H:
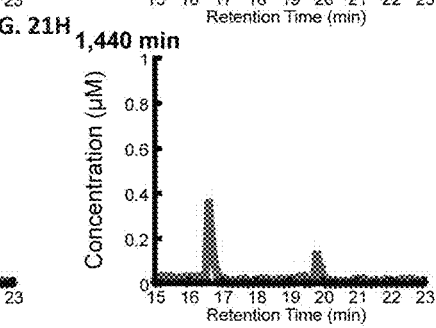
Figure 21I:
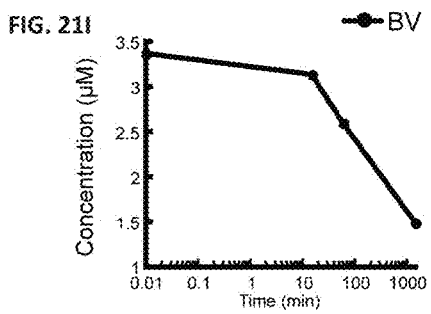
Figure 21J:
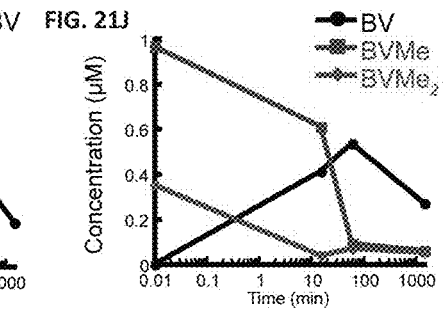

BV contains two anionic carboxylates. Acidification protonates the carboxylates and increases BV permeability. 25 µMBV added at pH 6.4 for 3.5 h increased fluorescence three-fold relative to BV at pH 7.5. As controls, BVMe2 incorporation or eGFP expression were not affected by a drop in extracellular pH from 7.5 to 6.4 over 3.5 h, showing no change in protein stability, protein translation, and cell health. Protonation of BV increased membrane permeability, but fluorescence was five-fold less than that of BVMe2.

smURFP and TDsmURFP with Different Chromophores smURFP and TDsmURFP have two chromophore sites, but the predominant species contains only 1 BV. smURFP and TDsmURFP were expressed without HO-1 and purified without chromophore, then chromophores were added in vitro. Samples were verified with MS (FIG. 17), and biophysical properties were measured. For BV and PCB, two chromophores could attach, but the second chromophore partially quenched fluorescence and reduced the QY (Table 7). Two PCBs had a 40-nm red-shifted fluorescence (FIG. 18g,i). A single BVMe$_2$ bound to smURFP, while two BVMe$_2$ bound to TDsmURFP (FIG. 17f,l). For BVMe$_2$, the QY of 12% remained constant. smURFP or TDsmURFP+ BVMe$_2$ have the brightest fluorescence, not only because BVMe$_2$ is freely membrane permeant, but because the fluorescence is not quenched by excess chromophore.

TABLE 7

Characteristics of smURFP/TDsmURFP + 1 or 2 chromophore

| Fluorescent Protein | Excitation Maximum (nm) | Emission Maximum (nm) | Extinction Coefficient (M$^{-1}$ cm$^{-1}$) | Quantum Yield (%) |
|---|---|---|---|---|
| smURFP + BV (E. coli) | 642 | 670 | 180,000 | 18 |
| smURFP + 1 BV | 642 | 672 | 160,000 | 16 |
| smURFP + 2 BV | 640 | 672 | 2 × 170,000 | 6.7 |
| smURFP + 1 PCB | 642 | 666 | 65,000 | 7.0 |
| smURFP + 2 PCB | 674 | 700 | 2 × 120,000 | 1.3 |
| smURFP + 1 BVMe$_2$ | 646 | 672 | 65,000 | 12 |
| TDsmURFP + BV (E. coli) | 642 | 670 | 170,000 | 18 |
| TDsmURFP + 1 BV | 644 | 674 | 150,000 | 16 |
| TDsmURFP + 2 BV | 644 | 674 | 2 × 190,000 | 6.5 |
| TDsmURFP + 1 PCB | 646 | 664 | 66,000 | 6.2 |
| TDsmURFP + 2 PCB | 674 | 704 | 2 × 120,000 | 1.4 |
| TDsmURFP + 1 BVMe$_2$ | 646 | 672 | 64,000 | 12 |
| TDsmURFP + 2 BVMe$_2$ | 646 | 674 | 2 × 18,000 | 12 | smURFP In Vivo

In order to test smURFP performance in vivo, HT1080 cells were transduced with lentivirus (≥99% efficiency) to express smURFP and mCherry (FIG. 19a). smURFP and mCherry fluorescence in the HT1080 cells in vitro were equivalent when the cells were incubated in 12.5 µM BV for 3 h (FIG. 19b). HT1080 cells stably expressing smURFP and mCherry were injected into four mice bearing two tumor xenografts. smURFP fluorescence was visible without exogenous BV (FIG. 4a), but fluorescence intensity was 35% of that of mCherry (FIG. 19c,d). 250 nmol BV was injected intravenously, but no fluorescence increase was seen after 2 h. Fluorescence of mCherry was greatly attenuated through the skin with a loss of 74%, while smURFP had a loss of only 25%, illustrating the importance of using FR and NIR FPs for deep-tissue imaging (FIG. 19e).

smURFP was compared to mCardinal[29] in smaller tumors in an area with less blood flow (FIG. 20). HT1080 cells were transduced with lentivirus expressing smURFP or mCardinal (≥95% efficiency) (FIG. 20a). The FPs were separated because of significant spectral overlap. smURFP is 2- to 4-fold brighter than mCardinal when BVMe$_2$ is added for 2 d (FIG. 20c-e), but smURFP is much dimmer than mCardinal in vivo (~7.3-fold at 607 nm and ~4-fold at 640 nm, FIG. 20f). Injection of 250 nmol BV or BVMe$_2$ gives no increase in fluorescence in vivo, though 10 µM BV or BVMe$_2$ added to excised tumors enhanced fluorescence and verified smURFP expression (FIG. 20g). 10 µM BV or BVMe$_2$ added to plasma showed rapid removal of ester groups and slower degradation of impermeant BV (FIG. 21), which explained the discrepancy.

FP Stability

Figure 22A:
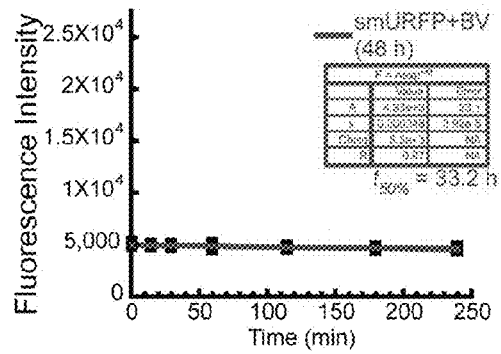
FIG. 22A-FIG. 22G: SmURFP stability with and without BV/BVMe2. HEK293A cells were transfected with smURFP IRES eGFP and protein was detected 48 h later. 25 µM BV (A) or 5 µM BVMe$_2$ (B) were incubated for 48 h to determine smURFP protein stability in the presence of chromophore. 25 µM BV (C) or 5 µM BVMe2 (D) were incubated for 3 h to determine smURFP protein stability in the presence of a short burst of chromophore. (E) SmURFP stability without chromophore. (F) EGFP stability was measured and $t_{50\%}$=20.5 h ($t_{50\%}$≈24 h). 50 µg/ml cycloheximide was added with 25 µM BV (A), 5 µM BVMe2 (B), or no chromophore (C-F). The mean fluorescent intensity (n=50) was determined for each time point from 5 images and fit to a single exponential decay (F=A exp$^{-kt}$). SmURFP shows increased protein stability in the presence of chromophore and is comparable to eGFP. SmURFP protein stability is >7-fold relative to the BPH FPS (iRFP713 and IFP1.4, Table 3) (G) Mean fluorescent intensity (n=50, 1 min time point) was plotted in order of increasing fluorescence. Incubation of smURFP with 25 µM BV increases fluorescence by 13- and 27-fold with 3 and 48 h, respectively. Incubation of smURFP with 5 µM BVMe2 increases fluorescence by 85-, 85-, and 125-fold with 1, 3, and 48 h, respectively. Increasing membrane permeability with BVMe$_2$ significantly increases fluorescence. Increased incubation time also increases fluorescence by stabilizing smURFP. Error bars are s.e.m. and * is P<0.0001.
Figure 22B:
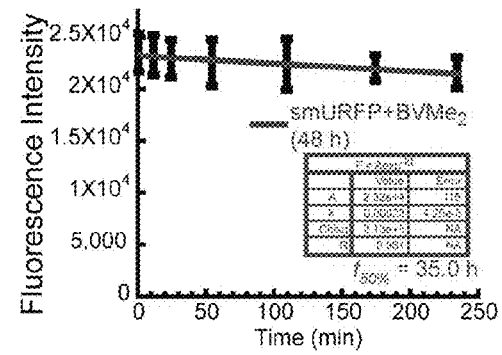
Figure 22C:
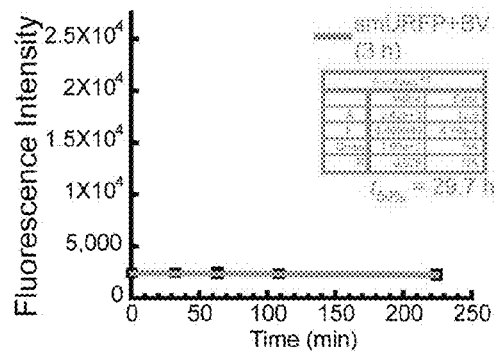
Figure 22D:
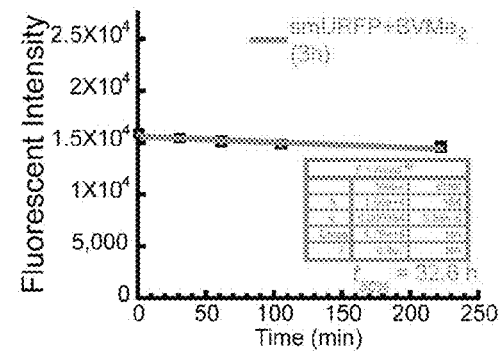

FP stability influences expression and fluorescence intensity. eGFP has a protein stability half-life (t$_{50\%}$) of ~24 h[30], while BPH FPs have t$_{50\%}$ of ~4.4 h (Table 3). The fluorescence of smURFP in HEK293 cells continuously exposed to BV or BVMe$_2$, but with protein synthesis halted by cycloheximide, declined with t$_{50\%}$=33 or 35 h, respectively (FIG. 22a,b). Shortening exposure of BV or BVMe$_2$ to 3 h produced little difference (t$_{50\%}$=30 h and 33 h, respectively) (FIG. 22c,d).

Figure 22E:
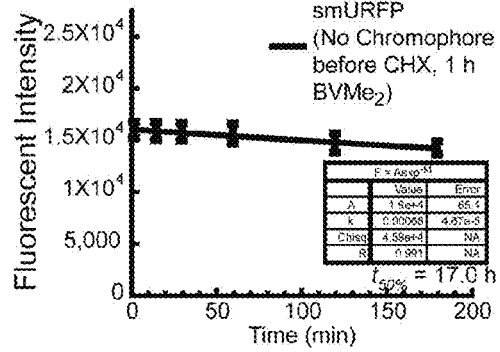
Figure 22F:
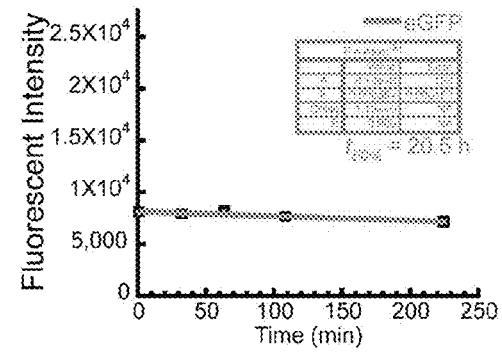
Figure 22G:
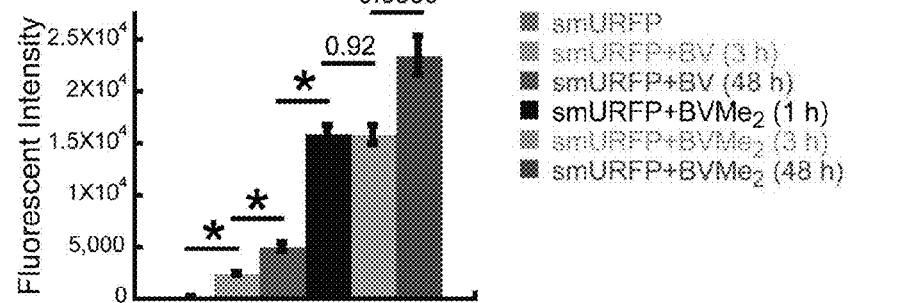

The lifetime of smURFP lacking chromophore was determined by addition of cycloheximide for various time periods, and BVMe$_2$ was added for 1 h. Apoprotein decayed with t$_{50\%}$=17 h (FIG. 22e), showing a modest destabilization. As a control, eGFP had a t$_{50\%}$=21 h, close to 24 h[30] (FIG. 22f). smURFP initial mean fluorescence shows that membrane permeability is the major factor increasing fluorescence under nonsteady state conditions, but increasing incubation time results in increased protein stability and accumulation of smURFP+chromophore (FIG. 22g).

FP Photostability and Performance in Fusions smURFP and TDsmURFP show greater photostability than eGFP, mCherry, IFP1.4, and Cy5 in vitro (FIG. 23). The protein, rather than the BV, governs the photostability, because at an excitation intensity yielding 1,000 photons per s, IFP1.4+BV bleached with $t_{50\%}$=8.4 s, while smURFP+BV had $t_{50\%}$=300 s (Table 3). Photostability was compared in cells. N- and C-terminal smURFP fusions were created and showed correct cellular localization (FIG. 4). smURFP mean $t_{50\%}$ was 340 s and 570 s with $BVMe_2$ and BV, respectively, in mammalian cells (FIG. 24). smURFP+BV photostability is com-parable to that of eGFP but greater than that of mCherry and tdTomato (Table 6).

maladies in vivo, where the production of hydrogen peroxide could alter immune system or inflammation response and/or alter disease progression[9-12]. Here, it is important to note that previous comparisons of BPH FPs and red FPs in vivo were performed using purified FPs, normalizing concentrations with BV already covalently attached, and by embedding FPs inside phantoms into mice[16,17]. This experimental setup does not accurately reflect FP expression and accessibility to BV in vivo where, for example, iRFP713 shows little fluorescence when compared to mCardinal[29].

TABLE 8

Photobleaching kinetics of FPs or FP fusions in mammalian cells (FIG. 24).

| | Single Exponential Decay Fit | | | Double Exportential Decay Fit | | | | | |
|---|---|---|---|---|---|---|---|---|---|
| Fluorescent Protein | A | k ($s^{-1}$) | R | $A_1$ | $k_1$ ($s^{-1}$) | $A_2$ | $k_2$ ($s^{-1}$) | R | $t_{50\%}$ (s) | Cells (n) |
| mCherry-18aa-αTub | 0.85 | 0.0054 | 0.99 | 0.24 | 0.066 | 0.76 | 0.0047 | 1.0 | 89 | 5 |
| tdTomato-10aa-LamB1 | 0.79 | 0.0019 | 0.96 | 0.34 | 0.00074 | 0.63 | 0.0063 | 1.0 | 180 | 7 |
| smURFP+$BVMe_2$ | 0.73 | 0.0015 | 0.97 | 0.42 | 0.020 | 0.57 | 0.0012 | 1.0 | 190 | 16 |
| PDHA1-10aa-smURFP+$BVMe_2$ | 0.77 | 0.0013 | 0.97 | 0.32 | 0.00058 | 0.62 | 0.0038 | 0.99 | 270 | 11 |
| smURFP+$BVMe_2$-18aa-αTub | 0.87 | 0.0013 | 0.98 | 0.36 | 0.00065 | 0.63 | 0.0031 | 1.0 | 350 | 6 |
| smURFP+BV | 0.75 | 0.00080 | 0.95 | 0.23 | 0.00024 | 0.72 | 0.0022 | 1.0 | 410 | 4 |
| ManII-10aa-smURFP+$BVMe_2$ | 0.83 | 0.00099 | 0.98 | 0.36 | 0.00051 | 0.59 | 0.0023 | 1.0 | 430 | 16 |
| PDHA1-10aa-smURFP+BV | 0.84 | 0.00097 | 0.98 | 0.26 | 0.00037 | 0.71 | 0.0020 | 1.0 | 450 | 11 |
| smURFP+$BVMe_2$-10aa-LamB1 | 0.87 | 0.000099 | 0.99 | 0.44 | 0.00058 | 0.56 | 0.0025 | 1.0 | 480 | 7 |
| eGFP | 0.97 | 0.0012 | 1.0 | | | | | | 560 | 12 |
| smURFP+BV-18aa-αTub | 0.85 | 0.00075 | 0.98 | 0.32 | 0.00031 | 0.67 | 0.0018 | 1.0 | 570 | 6 |
| ManII-10aa-smURFP+BV | 0.844 | 0.00069 | 0.98 | 0.34 | 0.0017 | 0.66 | 0.0017 | 1.0 | 630 | 9 |
| smURFP+BV-10aa-LamB1 | 0.89 | 0.00066 | 0.99 | 0.47 | 0.00044 | 0.52 | 0.00044 | 1.0 | 770 | 15 |

Data fit to single exponential decay fit: $F = A \exp^{-kt}$.
Data fit to double exponential decay fit: $F = A_1 \exp^{-k_1 t} + A_2 \exp^{-k_2 t}$.
$t_{50\%}$, time to bleach for 50% emission intensity.

An FR and NIR Fluorescent Cell Cycle Biosensor

Figure 25:
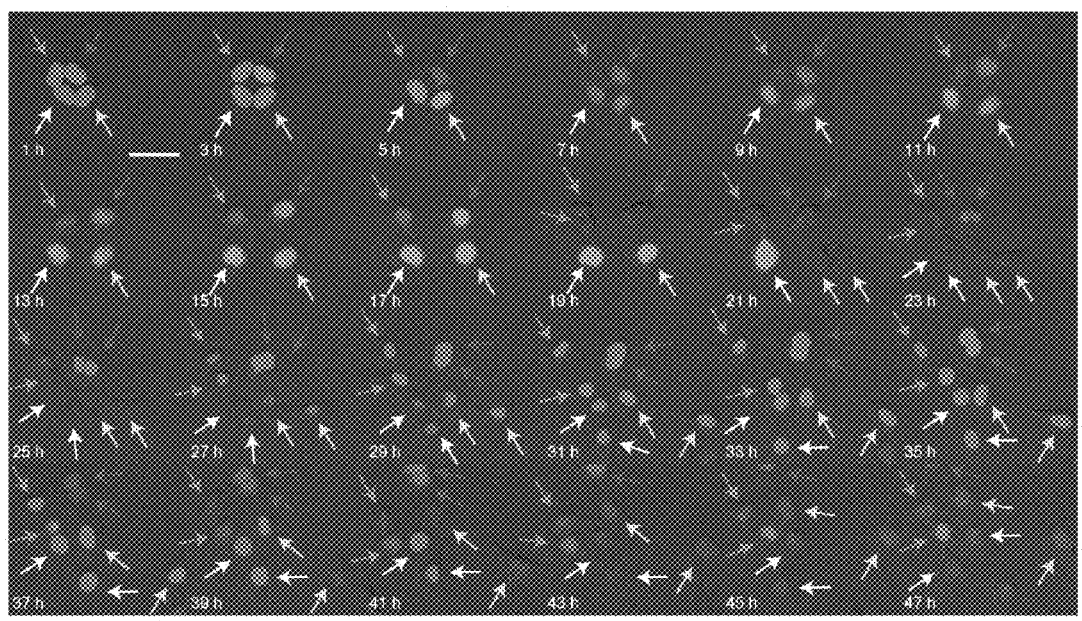
FIG. 25: Time-lapse microscopy of mAG-hGem (1/110) and smURFP-hCdtI (30/120) FUCCI expressed in HEK293A cells. MAG-hGem (1/110) and smURFP-hCdtI (30/120) fluorescence are shown in pseudocolor green and red, respectively. Cyan, magenta, white, and yellow arrows label the original four cells and their descendants. HEK293A cell division occurs with a doubling time of ~34 h. Green is EX/EM=495(10)/535(25) nm and red is EX/EX=628(40)/680(30) nm. EX is excitation; EM is emission; and scale bar=50 µm.
Figure 26A:
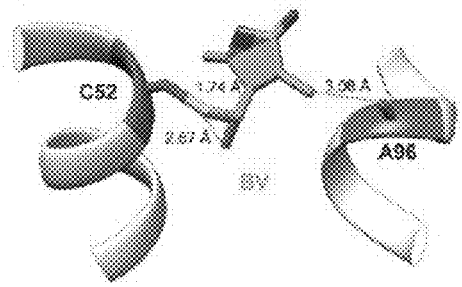
FIG. 26A-FIG. 26D: Dark smURFP. (A) Biliverdin (BV) covalently attached to smURFP is shown on the homology model. (B) Overlay of biliverdin attached to smURFP (cyan) and to the phytochrome fluorescent protein, IFP1.4 (dark green). (C) Cys52Ala and Ala96Cys mutations were made on smURFP to covalently attach biliverdin similarly to IFP1.4. This causes a red-shift in absorbance and fluorescence, which is shown in the white light images of the purified fluorescent proteins. (D) Dark smURFP has 24 nm red-shift in absorbance and is similar to the phtyochrome derived-fluorescent proteins.
Figure 26B:
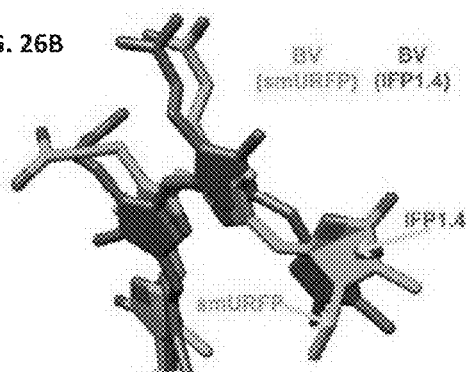
Figure 26C:
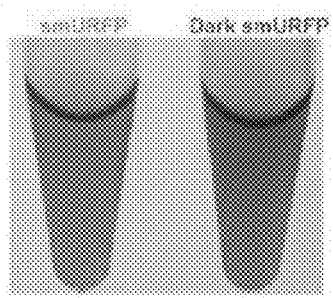
Figure 26D:
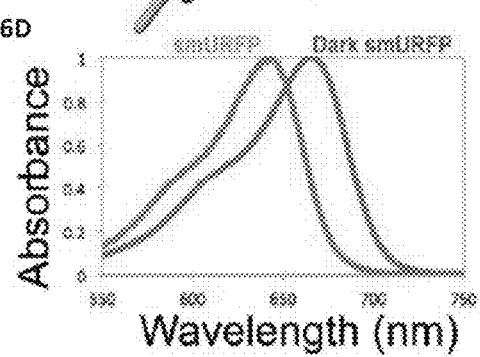
Figure 27A:
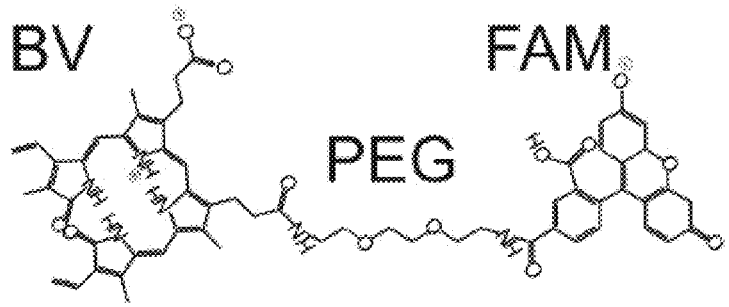
FIG. 27A-FIG. 27B: smURFP-tag. (A) BV-PEG-FAM (Labelled as BV-FAM in B). BV serves as a recognition sequence and fluorescence is turned "on" by covalent attachment. FAM is the cargo being genetically targeted. (B) smURFP-tag covalently attaches BV-FAM. smURFP-tag −/+ exogenous BV show little FAM fluorescence. smURFP-tag+25 µM BV-FAM shows significant FAM fluorescence. BV-FAM$_2$ does not covalently attach to the smURFP-tag. Untransfected cells+25 µM BV-FAM show no FAM fluorescence in the nuclei. Exposure time: Hoechst=50 ms and smURFP-tag and FAM=250 ms (unless noted). White numbers are mean fluorescent intensity (n=30).
Figure 27B:
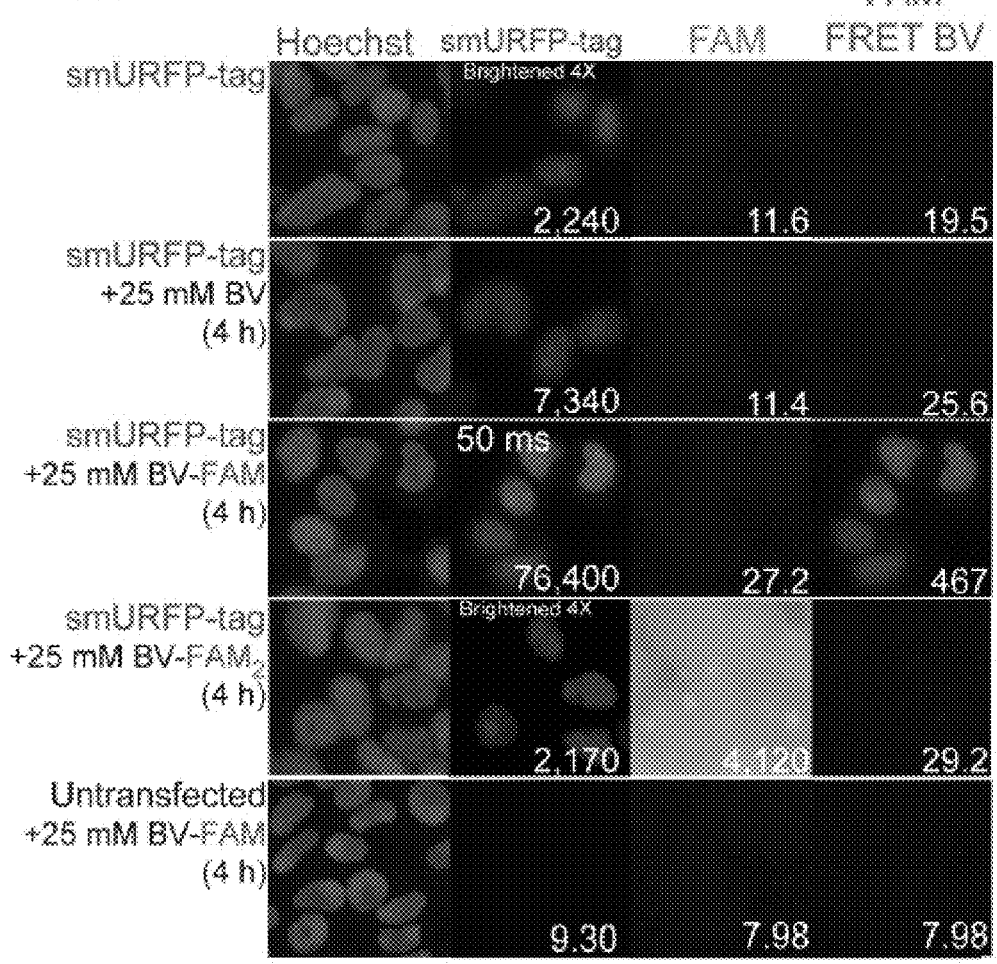
Figure 28:
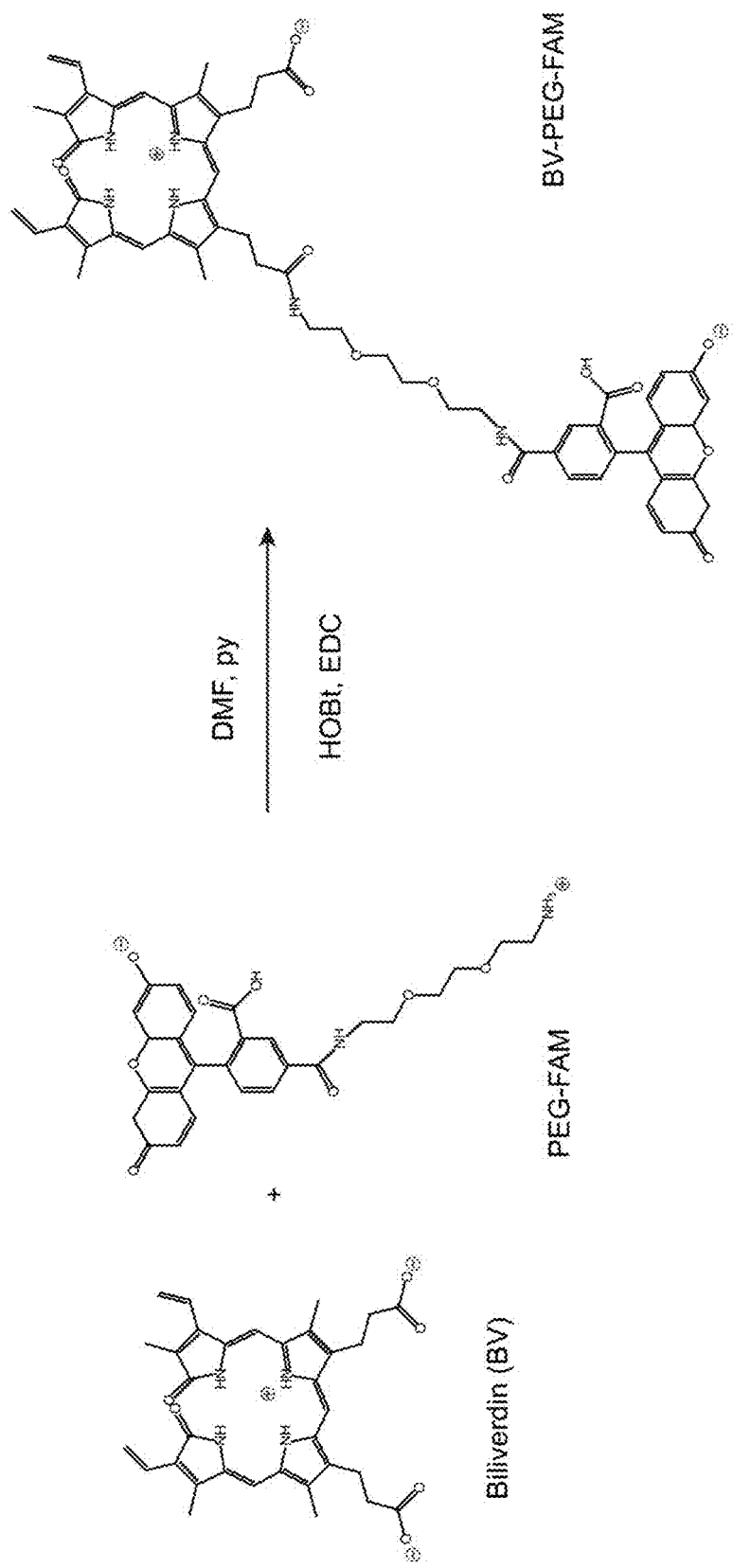
FIG. 28: BV-PEG-FAM synthesis.

Based on work from Miyawaki and coworkers[4] on the fluorescent ubiquitination-based cell cycle indicator (FUCCI), we created a fluorescent biosensor at wavelengths longer than attainable with jellyfish- or coral-derived FPs using smURFP and IFP2.0 (ref 18). In FUCCI, two spectrally distinct FPs are synthesized and degraded at opposing phases of the cell cycle. Typically a green FP is made during S, $G_2$, or M phase and degraded during late M or $G_1$ phase, while an orange FP is made during $G_0$ or $G_1$ phase and destroyed at the start of S phase[4]. smURFP, TDsmURFP, and IFP2.0 were fused to hCdt1(30/120) and hGem(1/110) fragments containing ubiquitination sites for degradation[4]. Stable HEK293A cell lines were created. smURFP fluorescence was greater than that of TDsmURFP. A stable cell line expressing mAG-hGem(1/110) and smURFP-hCdt1(30/120) was created to verify proper function. smURFP-hCdt1 (30/120) showed proper temporal dynamics (FIG. 25). Stably expressing IFP2.0-hGem(1/110) showed sufficient fluorescence, but IFP2.0-hCdt1(30/120) did not. Fluorescence time-lapse imaging verified that HEK293 cells stably expressing smURFP-hCdt1(30/120) and IFP2.0-hGem(1/110) reciprocally lit up during the $G_0$ or $G_1$ and S, $G_2$, or M phases, respectively (FIG. 5). FUCCI now works in the FR and NIR.

Discussion smURFP is biophysically the brightest FR and NIR FP created, fills a spectral gap in excitation wavelength, expresses efficiently with minimal toxicity, and does not produce hydrogen peroxide. In addition, unlike its precursor, TeAPCα, smuRFP does not require a lyase to covalently attach its chromophore.

smURFP fluorescence is visible without exogenous BV and may be advantageous for imaging cancer or other maladies in vivo, where the production of hydrogen peroxide could alter immune system or inflammation response and/or alter disease progression[9-12]. Here, it is important to note that previous comparisons of BPH FPs and red FPs in vivo were performed using purified FPs, normalizing concentrations with BV already covalently attached, and by embedding FPs inside phantoms into mice[16,17]. This experimental setup does not accurately reflect FP expression and accessibility to BV in vivo where, for example, iRFP713 shows little fluorescence when compared to mCardinal[29].

Membrane permeability of BV is a limiting factor for BPH FPs and smURFP. The development of smURFP fluorescence is controlled by the covalent attachment of the cofactor, not by reversible noncovalent BV affinity. HO-1 expression in neurons increases IFP2.0 fluorescence[18]. HO-1 increased fluorescence significantly for BPH and APCα FPs, and it enhanced more with 5-ALA and iron, which fuel production of heme that HO-1 converts to BV. smURFP and TDsmURFP, unlike BPH FPs, tolerate the freely permeant $BVMe_2$. This open chromophore-binding pocket (should allow for further modification of tetrapyrroles to modify not only membrane permeability but also spectral and fluorescence properties.

FP photostability is essential for imaging extended time periods or super-resolution. BPH FPs were originally non-fluorescent phototransducers that lacked evolutionary pressure to be light tolerant, whereas APCα is a component of the light-harvesting phycobilisome, which is extremely tolerant of light. Without using a special selection, smURFP is very photostable. Selection for increased photostability should enhance smURFP utility for super-resolution applications.

The FR and NIR FUCCI creates a fluorescent biosensor with wavelengths inaccessible to jellyfish or coral FPs and does not produce hydrogen peroxide. Fluorescently monitoring the cell cycle has identified modifications to cell division, drug-induced cell cycle modification[31], and quiescent cells[32].

smURFP is brighter than mCardinal in vitro when $BVMe_2$ is added for 2 d, and it is comparable to eGFP in brightness, which is useful in cell culture for imaging low-copy-number proteins, super-resolution imaging, and biosensors (FRET acceptor or red FP quencher). Despite its strong performance in vitro and modest visibility in vivo, smURFP is not ready for use in mice, as this will require screening new cofactors to achieve maximal brightness. smURFP is the most photostable FP tested in the Tsien lab (all FPs tested by P. Steinbach for over 10 years[3]). smURFP can be fused to α-tubulin (FIG. 4d), one of the most sensitive proteins. In addition, smURFP is one of only three FPs (smURFP, mKO2, and mCherry) known to allow functional fusion to hCdt1(30/120) despite the fact that jellyfish- or coral-derived FPs mAG, eGFP, and mRFP1 are nonfunctional[4]. The FR and NIR FUCCI is the first biosensor using two BV-attaching FPs and can be used with traditional FUCCI to monitor the cell cycle of two cell types.

There are thousands of APCα genes in cyanobacteria and red algae, giving this new class of FPs vast opportunities. Additionally, APCB and other phycobilisome proteins (phycoerythrin and phycocyanin) could be used to create additional FPs.

Accession codes. GenBank/EMBL/DDBJ: smURFP, KX449134; TDsmURFP, KX449135. Bacterial and mammalian expression plasmids and lentiviral transfer vectors are available at Addgene: smURFP, 80341, 80343, 80345, 80347, 80348, 80349; TDsmURFP, 80342, 80344, 80346.

Online Methods

Chemicals.

BV and BVMe$_2$ were purchased from Frontier Scientific. PCB was extracted from *Spirulina* as described[33].

Gene Synthesis, Mutagenesis, and Screening of Libraries.

TeAPCα gene (codons optimized for *Escherichia coli*) was made by GenScript. Mutations were placed by random mutagenesis using GeneMorphII Random Mutagenesis Kit (Agilent Technologies). Screens for mutants that fluoresce with PCB or BV were performed by subcloning into a pBAD vector (Life Technologies) that expressed cyanobacteria *Synechocystis* HO-1 and *Synechocystis* PcyA genes for PCB production and *Synechocystis* HO-1 only for BV production, as previously described[34]. Libraries were expressed in TOP 10 Electrocompetent *Escherichia coli* cells (Life Technologies) with addition of 0.2% arabinose to LB agar plates (FPs were constitutively expressed in *Escherichia coli*). Fluorescence was imaged on plates using a BioSpectrum AC Imaging System (UVP) with EX/EM=628(40)/690(50) nm for FPs+PCB, EX/EM=685(40)/710LP nm for rounds 4 and 5 FPs+BV, and EX/EM=650(13)/690(50) nm for Cy5-like FPs+BV (rounds 6-12). At round 6, 5-10 of the brightest colonies on each plate were combined in LB+0.2% arabinose, grown ~18 h, mixture of plasmid DNA was purified, and TOP10 cells were transformed and plated on LB agar plates+0.2% arabinose. Fluorescence was screened on plates (as described above), 10-20 of the brightest colonies were screened in liquid culture fluorescence (FIG. 7a-e), plasmid DNA was purified, and DNA was sequenced. The plasmid DNA of 2-3 of the brightest FPs was chosen for mutagenesis for the subsequent round. When choosing DNA for subsequent mutagenesis rounds, genes with increased and/or novel silent DNA mutations were chosen over other DNA that had the same DNA and/or protein sequence of the previous round. Site-specific mutagenesis was performed using QuikChange Lightning Mutagenesis Kit (Agilent Technologies) to create smURFP (C4S mutation) and smURFP C52S.

FP Purification and Fluorescence Characterization In Vitro.

FP genes were expressed on a pBAD vector (Life Technologies) with a polyhistidine tag on the C terminus, cells were lysed with B-PER (Thermo Scientific), and purified using Ni-NTA (Qiagen) puri-fication. PCB (HO-1+PcyA) and BV (HO-1) incorporation in *Escherichia coli* was performed simultaneously during constitu-tively active FP expression. Extinction coefficient was determined by PCB or BV absorbance as described35,36 (Table 3, smURFP+BV and TDsmURFP+BV, and Table 2) or calculated for the apoproteins by determining the protein concentration by the BCA protein assay (Pierce), and a specific chromo-phore concentration was added (specified in the Purification of FP lacking chromophore and in vitro chromophore incorporation section) to get 1 and 2 chromophore species (Table 5, not including (*Escherichia coli*)). When FP chromophore (PCB or BV) was expressed in *Escherichia coli*, the PCB and BV Q band had absorbance that overlapped with detection of BCA or Bradford assay of 562 nm and 592 nm, respectively. We used the previously published protocols35, 36, where there was no change of the BV absorbance at 390 nm when free in solution or attached to the FP. smURFP+BV denaturation with 1 M urea caused no change in the BV absorbance at 390 nm, but the Q band was reduced ~20-fold. Therefore, the extinction coefficient of BV at 390 nm was used to calculate the concentration of holoprotein (FP+PCB or BV) concentration.

EX and EM spectra were obtained using SPEX Fluorolog fluorometer (Horiba). Absorbance spectra were obtained using UV-VIS Spectrophotometer Cary Eclipse (Varian) or UV-2700 (Shimadzu). Quantum yield was determined relative to Cy5. Incorporation rates of BV on 0.5 μM smURFP was performed by addition of smURFP to PBS alone or with 20% fetal bovine serum (FBS) and mixed by pipetting in a quartz cuvette. Chromophore was added last, mixed by pipetting, and fluorescence was recorded using SPEX Fluorolog fluorometer (Horiba). Photobleaching was characterized on bubbles of purified FP or Cy5 within mineral oil using light from a 150 W xenon arc lamp with 100% light through EX/EM=628(40)/680(30) nm for smURFP, TDsmURFP, and Cy5 or EX/EM=665 (45)/725 (50) nm for IFP 1.4 focused with a 40×, 1.2 numerical aperture C-Apochromat oil-immersion lens on a Zeiss Axiovert 200M inverted microscope. Photobleaching times were normalized to reflect an initial illumination intensity producing 1,000 photons per fluorescent molecule per second as previously described[37].

Purification of FP Lacking Chromophore and In Vitro Chromophore Incorporation.

HO-1 was removed by digesting the pBAD vector (Life Technology) with MscI and PmeI (NEB). smURFP and TDsmURFP were expressed and purified as described above. No chromophore was present on smURFP and TDsmURFP (confirmed by UV, fluorescence imaging, and MS). For predominant fluorescent species+2 chromophores, a ten-fold excess of chromophore was added to smURFP and TDsmURFP. For predominant fluorescent species+1 chromophore, a quarter concentration of chromophore was added to smURFP and TDsmURFP. Chromophore was added in PBS+10% FBS at 37° C. overnight. smURFP+chromophore and TDsmURFP+chromophore were purified using NiNTA (Qiagen) to remove excess or noncovalently attached chromophore.

FP Mass Spectrometry.

FP mass was determined by liquid chromatography-mass spectrometry (LC-MS), where the protein column eluant was directly injected into the electrospray interface of an Orbitrap XL (Thermo Fisher). FP precipitation was minimized by using a steep gradient and injecting column eluant directly into the mass spectrometer. The 1100 LC (Agilent Technologies) had solvent A=2% acetonitrile (ACN), 0.1% formic acid (FA) and solvent B=90% ACN, 0.1% FA, the flow rate was 80 µl/min, and the gradient was 18% A to 100% B in 2.4 min. Protein was eluted within 10 min from a 1 mm inner diameter, 50 mm long PLRP-S C18 column (Agilent Technologies). Orbitrap IonSpray (electrospray) interface had a sheath gas flow rate of 34 and T=275° C. Capillary was 39 V and the tube lens was 140 V. Full scan mass spectra were collected in the ion trap and Fourier transform profile mode, with Orbitrap resolution 60,000, from 500 to 1,800 mass-to-charge units. Protein mass spectra were deconvolved using either the extract msn program (Xcalibur software) or with ProMassCalc (ThermoFisher).

Homology Model Creation, Identifying Dimeric Interface, Protein Sequence Alignment, and Creating Protein Figures.

smURFP homology model was created using Swiss-Model Server[38] with *Porphyra yezoensis* APCα crystal structure (1KN1.pdb[39] (http://www.rcsb.org/pdb/explore.do?structureId=1KN1) and sequence in FIG. 6). The homodimeric interface was identified using PatchDock[40] and, subsequently, FireDock[41]. The lowest free-energy structure is shown in FIG. 1d. Protein sequence alignments (FIGS. 6 and 7) were created using ClustalX[42]. All protein figures were created using UCSF Chimera package[43].

Construction of TDsmURFP Bacterial Expression Vector.

TDsmURFP was created using the smURFP homology model (FIG. 1d) and approximating the distance from the C terminus to the N terminus of the second subunit. A 23-amino-acid linker (GHGTGSTGSGSSGTASSEDN-NMA) was sufficient, and primers were created with 5' BamHI and 3' EcoRI restriction sites (Integrated DNA Technologies, IDT) smURFP was PCR amplified with Phusion High-Fidelity DNA Polymerase (New England Bio-Labs, NEB) to create the right and left subunits using 23-amino-acid linker primers. The two products were combined, and TDsmURFP was created by bridging PCR with Phusion High-Fidelity DNA Polymerase (NEB). TDsmURFP was digested with BamHI-HF and EcoRI-HF (NEB), gel purified using Zymoclean Gel DNA Recovery Kit (Zymo), and subcloned into a pBAD (Life Technologies) vector containing HO-1 digested with BamHI-HF and EcoRI-HF (NEB) with T4 DNA Ligase (Life Technologies).

Native PAGE, SDS-Denaturing PAGE, and Zinc Blot.

Native PAGE was run using NativePAGE Novex Bis-Tris Gel System (Life Technologies) on Native PAGE 4-16% Bis-Tris protein gels (Life Technologies). SDS-denaturing PAGE was run using NuPAGE MOPS SDS running buffer (Life Technologies) and NuPAGE Novex 4-12% Bis-Tris gels (Life Technologies). Precision Plus Protein Dual Color Standards (Bio-Rad) were used as an MW ladder. Zinc blot was performed after running the SDS-PAGE gel using the described method[44]. Fluorescence was imaged using a Bio-Spectrum AC Imaging System (UVP) with EX/EM=535(45)/605(70) nm for tdTomato, EX/EM=650(13)/690(50) nm for smURFP and TDsmURFP, EX/EM=685(40)/710LP nm for IFP1.4 and BV+zinc.

Construction of Lentiviral Vectors, Virus Production, and Neuron Infection.

smURFP-T2A-mCherry (GenBank AY678264), smURFP-T2A-mCardinal, smURFP, and mCardinal (Addgene 51311) were subcloned in a generation-two lentiviral vector with the CMV promoter for constitutive expression. Viruses were produced as described[45]. The procedures for extracting cultured neurons from rat pups were approved by the UCSD Institutional Animal Care and Use Committee (IACUC, #503172R) and are consistent with the recommendations of the American Veterinary Medical Association. Primary cortical neurons were dissociated by papain from postnatal day 2 Sprague Dawley rats (n=6) of either sex and combined, plated on poly-D-lysine-coated glass-bottom culture dishes (MatTek, #P35G-0-14-C), and cultured in Neurobasal A medium+1×B27 supplement (Life Technologies)+2 mM GlutaMAX (Life Technologies)+1×penicillin-streptomycin (Fisher Scientific). Prior to fluorescence imaging, 25 µM BV was added for 10 min, removed, and washed with 2×2 ml Hank's Balanced Salt Solution (HBSS, Life Technologies)+2 g/L glucose+20 mM HEPES (pH 7.4), referred to as imaging solution. Fluorescence imaging was performed in vitro 15 d after infection using a Zeiss Axiovert 200M inverted microscope controlled by SlideBook software. FPs were imaged as follows: smURFP and TDsmURFP, EX/EM=628(40)/680(30) nm; and mCherry, EX/EM=580(20)/653(95) nm.

Fluorescence Imaging of HT1080 Tumor Xenografts In Vivo.

HT1080 cells were infected with CMV with smURFP-T2A-mCherry, smURFP-T2A-mCardinal, smURFP, and mCardinal lentiviruses in culture, and expression was verified by fluorescence imaging (FIG. 19a, ≥99% efficiency and FIG. 20a, ≥95% efficiency) using filters described in the previous section. All procedures using mice were approved by UCSD IACUC (#S03172M) and are consistent with the recommendations of the American Veterinary Medical Association. One million HT1080 cells expressing smURFP-T2A-mCherry were injected subcutaneously into the lateral, ventral, and upper right and left quadrant, or smURFP and mCardinal were injected subcutaneously into the lateral, dorsal, and lower right and left quadrant of four 5-week-old athymic nude female mice. Tumors were allowed to grow until ~0.1-1 cm in diameter (~2 weeks). Mice were anesthetized with isoflurane (1.5%) at a 2 liter/min flow, injected with ketamine-midazolam (intraperitoneal (IP), 80 mg/kg, 4 mg/kg), placed on a heated pad, and imaged before exogenous BV injection. 250 nmol BV was injected by intravenous (IV) tail vein, and mice were imaged 5, 30, 60, and 120 min after BV injection for smURFP-T2A-mCherry. 250 nmol BV or BVMe2 was injected by intravenous tail vein, and mice were imaged 60 min, 24 h, and 48 h after BV injection for smURFP and mCardinal tumors. Mice were imaged using a Maestro in vivo Imaging System (Cambridge Research & Instrumentation, CRI). FPs were imaged with the following filters: mCherry, EX/EM=590(23)/615LP nm and liquid crystal, 620 nm; mCardinal EX/EM=607(36) 645LP nm and liquid crystal, 660 nm; and smURFP EX/EM=620(20)/645LP nm or EX/EM=640(47)/700LP and liquid crystal, 710 nm. Image cubes were obtained and could be spectrally unmixed, but raw fluorescence images before chromophore injection are shown in FIGS. 19c and 20f because no fluorescence increase was seen after 250 nmol BV or BVMe$_2$ injection. Tumors were removed, washed 2× in 2 ml DMEM+10% FBS, labeled in 2 ml DMEM+10% FBS+10 µM BV or BVMe$_2$ at 4° C. for 24 h, imaged, labeled in 2 ml DMEM+10% FBS+10 µM BV or BVMe$_2$ at 37° C. for 24 h, and imaged (FIG. 20g).

Plasma Collection and BV or BVMe$_2$ Concentration Analysis.

Whole blood was collected via abdominal aorta and placed in tubes with lithium heparin (BD, No. 365971) on ice. Tubes were centrifuged to remove red blood cells, and plasma was stored on ice for 30 min. Clarified plasma was combined and aliquoted into 9×70 µl aliquots and placed on ice. The following nine experiments were performed: starting plasma (1) and plasma+10 µM BV (2-5) or BVMe$_2$(6-9) at time 0 at 4° C. and 15, 60, and 1,440 min at 37° C. Reactions were stopped by freezing at −80° C. Plasma samples were thawed, diluted 4× with cold 50% ACN, 48% water ($H_2O$), and 2% acetic acid, and centrifuged for 14 min at 4° C. Reverse-phase high performance liquid chromatography (HPLC) was performed on an Agilent 1100 Series HPLC on a Phenomenex Luna C18(2) reverse-phase column 100 Å, 250 cm×21.20 mm I.D. 10 μm reverse-phase column (00G-4253-P0 AX), with a 21 min, 10-90% H2O:ACN (0.05% trifluoroacetic acid, TFA) gradient and a flow rate of 1 ml/min into a diode array detector and MSD-Ion Trap (Agilent LC/MSD trap XCT). 5 mM BV or BVMe2 in DMSO was diluted and used to calibrate the concentration of chromo-phore as a function of peak area (FIG. 21).

Mammalian Expression Plasmids, Cell Culture, Transfection, Chromophore Addition, and Fluorescence Imaging.

smURFP codons were optimized for human cell expression, and the gene was created by GenScript. smURFP, TDsmURFP (created from mammalian-optimized smURFP), IFP1.4 (mammalian-optimized form[35]), IFP2.0 (mammalian-optimized form[46]), and iRFP713 (mammalian-optimized form[36]) were PCR amplified using Phusion High-Fidelity DNA Polymerase (NEB) with primers containing 5' HindIII and 3' XhoI restriction enzyme sites. HindIII-HF and XhoI (NEB)-digested PCR fragments were gel purified (Zymoclean Gel DNA Recovery Kit) and were ligated (T4 DNA Ligase, Life Technologies) into a similarly digested pCDNA3-IRES-eGFP vector (bicistronic to express two FPs in the same cell). For creation of HO-1-expressing mammalian vec-tors, the Synechocystis HO-1 was used, and the codons were not optimized for mammalian expression. Synechocystis HO-1 was directly amplified from the pBAD vector using primers containing 5' BsiWI and 3' XbaI restriction enzyme sites. pCDNA3 smURFP, TDsmURFP, IFP1.4, IFP2.0, or iRFP713-IRES-eGFP vectors were digested with BsiWI and XbaI (NEB), dephosphorylated (SAP, Roche), gel purified (Zymoclean Gel DNA Recovery Kit), and ligated (T4 DNA Ligase, Life Technologies) with similarly digested, purified HO-1 PCR fragment. For creation of smURFP fusions, smURFP was PCR amplified using Phusion High-Fidelity DNA Polymerase (NEB) with primers containing 5' AgeI and 3' NotI restriction enzyme sites for N-terminal fusions or with primers containing 5' AgeI and 3' BspEI restriction enzyme sites for C-terminal fusions. mGeos2-VEL-ManII-N-10 (Addgene 57551) and Dronpa-PDHA1-N-10 (Addgene 57292) vectors were digested with AgeI and NotI (NEB) and mCherry-αTubulin-C-18 (Addgene 55148) and tdTomato-LaminB1-10 (Addgene 58107) were digested with AgeI and BspEI, dephosphorylated (SAP, Roche), gel purified (Zymoclean Gel DNA Recovery Kit), and ligated (T4 DNA Ligase, Life Technologies) with similarly digested, purified smURFP PCR fragment. HEK293A (Invitrogen, Life Technologies), HT1080 (ATCC), and PC3 (ATCC) cells were grown in Dulbecco's Modified Eagle's medium (DMEM, Corning), supplemented with 10% FBS (Atlanta Biologicals)+1×penicillin—streptomycin (Fisher Scientific), which is referred to as growth media, on poly-D-lysine-coated glass-bottom culture dishes (MatTek, No. P35G-0-14-C). The HEK cell line is listed in the ICLAC and NCBI biosample databases and is commonly misidentified as the HeLa cell line. For expression of exogenous fluorescent proteins, there is no problem if there is a contaminating cell line because no endogenous biology or therapeutic results are being determined. HEK293A cells were purchased from Invitrogen (Life Technologies), and all experiments are derived from the same expanded frozen stock without cell line authentication or mycoplasma detection. Cells were transfected using 2 μg of circular DNA+5 μl Lipofectamine 2000 (Life Technologies) in 2 ml Opti-MEM (Life Technologies) for 4-5 h, transfection media was discarded, and prewarmed growth media was added. Chromophores (5 mM in DMSO) were added at indicated concentrations to growth media, warmed for 10-15 min at 37° C., and added to cells. For multiple timepoints, incubations were staggered to maintain equivalent incubation. Prior to imaging, cells were washed 1×2 ml growth media, 2×2 ml imaging solution, and imaged in 2 ml imaging solution. Fluorescence imaging was performed on a Zeiss Axiovert 200M inverted microscope controlled by SlideBook software. FPs were imaged with the following settings: eGFP, EX/EM=495(10)/535(25) nm; tdTomato EX/EM=540(25)/595(50) nm; mCherry and mCardinal, EX/EM=580(20)/653(95) nm; smURFP and TDsmURFP, EX/EX=628(40)/680(30) nm; and IFP1.4, IFP2.0, and iRFP713, EX/EM=665(45)/725(50) nm. When comparing mean fluorescence intensity of FPs with different wavelengths, data was normalized to reflect chromophore absorbance, chromophore extinction coefficient, light power (measured with an IL1700 research radiometer (International Light Technologies)), objective, EX/EM filters transmission, and dichroic reflectance as described[37].

FP Stability in HEK293A Cells.

HEK293A cells were transfected with pCDNA3-smURFP-IRES-eGFP and incubated for 48 h. 25 μM BV or 5 μM BVMe$_2$ was added to HEK293A cells as listed in FIG. 22. 50 μg/ml cycloheximide+25 μM BV, 5 μM BVMe$_2$, or no chromophore was added and cells were imaged after 1, 10, 30, 60, 120, and 225 min. Fluorescence was fit to a single exponential decay (F=A [exp$^{-kt}$]), where F is fluorescence that varies as a function of time, A is the fit initial fluorescence, k is the rate of fluorescence decay (protein degradation), and t is time in min. Fitted values and $t_{50\%}$ (calculated by $t_{50\%}$=ln(2)/k) of FPs are listed in FIG. 22.

Photobleaching FP or FP Fusions in Mammalian Cells.

PC3 cells were transfected with 2 μg of circular DNA+5 μl Lipofectamine 2000 (Life Technologies) in 2 ml Opti-MEM (Life Technologies) for 4-5 h, transfection media was discarded, prewarmed growth media was added, and protein was produced for 48 h. 25 μM BV or 1 μM BVMe$_2$ was incubated for 4 h. Cells were photobleached with continuous light exposure from a 150 W xenon arc lamp with eGFP EX/EM=495(10)/535(25) nm, tdTomato EX/EM=540(25)/595(50) nm, mCherry EX/EM=580(20)/53(95) nm, and smURFP EX/EM=628(40)/680(30) nm focused with a 40×, 1.2 numerical aperture C-Apochromat oil-immersion lens on aZeiss Axiovert 200M inverted microscope. Photobleaching times were normalized to reflect an initial illumination intensity producing 1,000 photons per fluorescent molecule per second as previously described[37]. Data was fit to a single exponential decay (F=A [exp$^{-kt}$]), where F is fluorescence that varies as a function of time, A is the fit normalized, initial fluorescence (should be 1), k is the rate of fluorescence decay (photobleaching), and t is time in s, or a double exponential decay (F=$A_1$[exp$^{-k_1 t}$]+$A_2$[exp$^{-k_2 t}$]), where F is fluorescence that varies as a function of time, $A_1$ and $A_2$ are the fit normalized, initial fluorescence (sum should be 1), $k_1$ and $k_2$ are the rates of fluorescence decay (photobleaching), and t is time in seconds, and data is shown in Table 6.

Creating and Imaging Transiently or Stably Expressing FR and NIR FUCCI in HEK293A Cells.

pCSII-EF-containing mAG-hGem(1/110) or mKO2-hCdtI(30/120) (A. Miyawaki, RIKEN) were PCR amplified using Phusion High-Fidelity DNA Polymerase (NEB) with primers containing 5' HindIII-HF and 3' XbaI restriction enzyme sites. HindIII-HF and XbaI (NEB)-digested PCR fragments were gel purified (Zymoclean Gel DNA Recovery Kit) and were ligated (T4 DNA Ligase, Life Technologies) into a similarly digested pCDNA3 vector, creating initial pCDNA3-mAG-hGem(1/110) or mKO2-hCdtI(30/120) vectors. smURFP, TDsmURFP, and IFP2.0 were PCR amplified using Phusion High-Fidelity DNA Polymerase (NEB) with primers containing 5' HindIII and 3' XhoI, HindIII-HF and XhoI digested (NEB), gel purified (Zymoclean Gel DNA Recovery Kit). pCDNA3mAG-hGem(1/110) or mKO2-hCdtI(30/120) were digested with HindIII-HF and XhoI (NEB) to remove the FP and linker, dephosphorylated (SAP, Roche), and gel purified (Zymoclean Gel DNA Recovery Kit). pCDNA3 X-hGem(1/110) or hCdtI(30/120) were ligated with smURFP, TDsmURFP, and IFP2.0 to create pCDNA3 smURFP, TDsmURFP, or IFP2.0-hGem(1/110) or hCdtI(30/120), six plasmids with hygromycin B resistance to create stable cell lines.

HEK293A cells were transfected with Lipofectamine 2000 (Life Technologies) on glass-bottom dishes (grown and transfected as described above). Initially, all eight constructs (including mAG-hGem(1/110) and mKO2-hCdtI (30/120)) were fluorescently imaged using a Zeiss Axiovert 200M inverted microscope controlled by SlideBook software. FPs were imaged as follows: mAG EX/EM=495(10)/535(25) nm, mKO2 EX/EM=540(25)/595 (50)nm, smURFP or TDsmURFP EX/EX=628(40)/680(30)nm, and IFP2.0 EX/EM=665(45)/725(50) nm. smURFP, TDsmURFP, or IFP2.0-hGem(1/110) or hCdtI(30/120) all had fluorescent nuclei when transiently expressed in HEK293A cells. A kill curve was generated with hygromycin B (Life Technologies) and 300 µg/ml hygromycin B was sufficient to kill untransfected HEK293A cells. HEK293A cells expressing mAG or IFP2.0-hGem(1/110) or mKO2 or IFP2.0-hCdtI(30/120) were grown for 3 weeks in growth media+300 µg/ml hygromycin B. Cells were selected using fluorescently activated cell sorting (FACS) using FACSDiVa (BD Biosciences) to give an enriched stable population containing the expressed FP fusion. Cells expressing FPs were sorted using the following filters: mAG EX/EM=488/535(20) nm, mKO2 EX/EM=568/610(40) nm, and IFP2.0 EX/EM=670/710LP nm. HEK293A cells expressing mAG or IFP2.0-hGem(1/110) were transfected with smURFP or TDsmURFP-hCdtI (30/120), or mKO2 or IFP2.0-hCdtI(30/120) were transfected with smURFP or TDsmURFP-hGem(1/110) and grown for an additional 3 weeks in growth media +300 µg/ml hygromycin B. 198 individual clones were FACS (smURFP EX/EM=647(10)/675(20) nm) for the eight combinations and grown for 2 weeks. Clones were initially assayed to verify both FPs and then proper growth (many cells show no growth and/or decreased cell cycle progression, which was typically accompanied by higher FP-fusion expression). TDsmURFP fusions were dimmer than smURFP fusions and were not characterized further. IFP2.0-hCdtI(30/120) or smURFP-hGem(1/110) fluorescence was lacking and/or extremely dim and could not be visualized with smURFP-hGem(1/110) or mKO2-hCdtI(30/120), respectively. mAG-hGem(1/110)+smURFP-hCdtI(30/120) and IFP2.0-hGem(1/110)+smURFP-hCdtI(30/120) (FR and NIR FUCCI) had sufficient fluorescence, and three clones of each were grown and reanalyzed for fluorescence of both FPs and adequate growth. A single clone of each was imaged by time-lapse fluorescence microscopy.

Time-Lapse Imaging of FUCCI HEK293A Cells.

HEK293A cells stably expressing FUCCI were grown in growth media on glass-bottom dishes coated with poly-D-lysine. After 2 d, media was changed to 2 ml Leibovitz L-15 medium (no phenol red, Life Technologies)+1 g/L glucose+200 µM Trolox+200 µM L-ascorbic acid+12.5 BV for 1 d. A Zeiss Axiovert 200M inverted microscope with temperature control chamber was allowed to equilibrate at 37° C. for ~30 min and HEK293A FUCCI cell-imaging dish was placed on the stage. The plastic lid was removed and 2.2 ml of mineral oil was added to the top (ensuring complete seal to avoid media evaporation). A metal imaging dish weight sealed with a glass coverslip was placed on top of the imaging chamber to avoid focus drift during imaging. The microscope+dish were equilibrated for ~1 h at 37° C. Cells were imaged every 15 min using a 10% neutral density filter. FPs were imaged as follows: mAG-hGem(1/110) EX/EM=488/535(20) nm, smURFP-hCdtI(30/120) EX/EM=628(40)/680(30) nm, and IFP2.0-hGem(1/110) EX/EM=665(45)/725(50) nm. Movies were created in ImageJ[47]. All three image channels (DIC, smURFP-hCdtI (30/120), and mAG or IFP2.0-hGem(1/110)) were opened separately as a hyperstack and brightness and contrast were adjusted as desired. The time was added to the DIC stack using Time Stamper (ImageJ plugin) and the three channels were merged using the following pseudocoloring: red, smURFP-hCdtI(30/120); green, mAG or IFP2.0-hGem(1/110); and gray, DIC. The AVI movie was exported using JPEG compression and ten frames per second in ImageJ. AVI movies were converted to MOV movies using Quick-Time Player (Version 10.4, Apple). Data not shown.

Experimental Setup, Data Analysis, and Statistical Methods.

For cell culture experiments, sample sizes of ≥n=30 cells (n listed with each experiment) were chosen to ensure P values<0.03 for the majority of significant comparisons. For animal experiments, four mice with two tumors each (n=8 tumors) were chosen arbitrarily to ensure reproducibility of results. No cell culture dishes or animals were excluded from analysis for any reason. For animal studies, no randomization or blinding was used because both mCherry and smURFP FPs were simultaneously expressed on a bicistronic mRNA in each tumor cell that made up the tumor, or smURFP and mCardinal tumors were imaged simultaneously on the same mouse. Tumors were imaged with both sets of excitation and emission filters. Fluorescence images were adjusted and analyzed using ImageJ[47]. Graphs, statistics, and statistical significance tests were generated using KaleidaGraph 4.1 (Synergy). Comparisons were performed on mean fluorescence intensity with a one-way ANOVA with significance level set at $\alpha$=0.05. Equivalence of variance was determined for the one-way ANOVA with a post hoc test of Tukey honestly significant difference (HSD) for comparisons between any two samples. All error bars are s.e.m., except FIG. 3a,b is calculated as error propagation of the s.e.m.

DNA Constructs.

GenBank/EMBL/DDBJ: smURFP, KX449134; TDsmURFP, KX449135. Bacterial and mammalian expression plasmids and lentiviral transfer vectors are available at Addgene: smURFP, 80341, 80343, 80345, 80347, 80348, 80349; and TDsmURFP, 80342, 80344, 80346.

See, also, Rodriquez, et al., Nature Methods, 13(9): 763-769 (2016), which is incorporated by reference herein in its entirety for all purposes, including all supplementary materials.

REFERENCES

1. Giepmans, B. N., Adams, S. R., Ellisman, M. H. & Tsien, R. Y. The fluorescent toolbox for assessing protein location and function. Science 312, 217-224 (2006).

2. Tsien, R. Y. Constructing and exploiting the fluorescent protein paintbox (Nobel lecture). Angew. Chem. Int. Edn. Engl. 48, 5612-5626 (2009).
3. Shaner, N.C., Steinbach, P. A. & Tsien, R. Y. A guide to choosing fluorescent proteins. Nat. Methods 2, 905-909 (2005).
4. Sakaue-Sawano, A. et al. Visualizing spatiotemporal dynamics of multicellular cell-cycle progression. Cell 132, 487-498 (2008).
5. Tsien, R. Y. The green fluorescent protein. Annu. Rev. Biochem. 67, 509-544 (1998).
6. Shaner, N.C. et al. Improved monomeric red, orange and yellow fluorescent proteins derived from Discosoma sp. red fluorescent protein. Nat. Biotechnol. 22, 1567-1572 (2004).
7. Moore, M. M., Oteng-Pabi, S. K., Pandelieva, A. T., Mayo, S. L. & Chica, R. A. Recovery of red fluorescent protein chromophore maturation deficiency through rational design. PLoS ONE 7, e52463 (2012).
8. Tubbs, J. L., Tainer, J. A. & Getzoff, E. D. Crystallographic structures of Discosoma red fluorescent protein with immature and mature chromophores: linking peptide bond trans-cis isomerization and acylimine formation in chromophore maturation. Biochemistry 44, 9833-9840 (2005).
9. Veal, E. A., Day, A. M. & Morgan, B. A. Hydrogen peroxide sensing and signaling. Mol. Cell 26, 1-14 (2007).
10. Hussain, S. P., Hofseth, L. J. & Harris, C. C. Radical causes of cancer. Nat. Rev. Cancer 3, 276-285 (2003).
11. Weitzman, S. A. & Gordon, L. I. Inflammation and cancer: role of phagocyte-generated oxidants in carcinogenesis. Blood 76, 655-663 (1990).
12. Barnham, K. J., Masters, C. L. & Bush, A. I. Neurodegenerative diseases and oxidative stress. Nat. Rev. Drug Discov. 3, 205-214 (2004).
13. Kumagai, A. et al. A bilirubin-inducible fluorescent protein from eel muscle. Cell 153, 1602-1611 (2013).
14. Konig, K. Multiphoton microscopy in life sciences. J. Microsc. 200, 83-104 (2000).
15. Shu, X. et al. Mammalian expression of infrared fluorescent proteins engineered from a bacterial phytochrome. Science 324, 804-807 (2009).
16. Filonov, G. S. et al. Bright and stable near-infrared fluorescent protein for in vivo imaging. Nat. Biotechnol. 29, 757-761 (2011).
17. Shcherbakova, D. M. & Verkhusha, V. V. Near-infrared fluorescent proteins for multicolor in vivo imaging. Nat. Methods 10, 751-754 (2013).
18. Yu, D. et al. An improved monomeric infrared fluorescent protein for neuronal and tumour brain imaging. Nat. Commun. 5, 3626 (2014).
19. Auldridge, M. E., Satyshur, K. A., Anstrom, D. M. & Forest, K. T. Structure-guided engineering enhances a phytochrome-based infrared fluorescent protein. J. Biol. Chem. 287, 7000-7009 (2012).
20. Fischer, A. J. & Lagarias, J. C. Harnessing phytochrome's glowing potential. Proc. Natl. Acad. Sci. USA 101, 17334-17339 (2004).
21. Yeh, S. W., Ong, L. J., Clark, J. H. & Glazer, A. N. Fluorescence properties of allophycocyanin and a cross-linked allophycocyanin trimer. Cytometry 8, 91-95 (1987).
22. Tooley, A. J., Cai, Y. A. & Glazer, A. N. Biosynthesis of a fluorescent cyanobacterial C-phycocyanin holo-α subunit in a heterologous host. Proc. Natl. Acad. Sci. USA 98, 10560-10565 (2001).
23. Zhang, J. et al. Fused-gene approach to photoswitchable and fluorescent biliproteins. Angew. Chem. Int. Edn. Engl. 49, 5456-5458 (2010).
24. Harris, J. W. & Kellermeyer, R. W. The Red Cell: Production, Metabolism, Destruction: Normal and Abnormal, Revised edn. (Harvard University Press, 1970).
25. Wahleithner, J. A., Li, L. M. & Lagarias, J. C. Expression and assembly of spectrally active recombinant holophytochrome. Proc. Natl. Acad. Sci. USA 88, 10387-10391 (1991).
26. Arciero, D. M., Bryant, D. A. & Glazer, A. N. In vitro attachment of bilins to apophycocyanin. I. Specific covalent adduct formation at cysteinyl residues involved in phycocyanobilin binding in C-phycocyanin. J. Biol. Chem. 263, 18343-18349 (1988).
27. Li, L., Murphy, J. T. & Lagarias, J. C. Continuous fluorescence assay of phytochrome assembly in vitro. Biochemistry 34, 7923-7930 (1995).
28. Katayama, H., Yamamoto, A., Mizushima, N., Yoshimori, T. & Miyawaki, A. GFP-like proteins stably accumulate in lysosomes. Cell Struct. Funct. 33, 1-12 (2008).
29. Chu, J. et al. Noninvasive intravital imaging of cellular differentiation with a bright red-excitable fluorescent protein. Nat. Methods 11, 572-578 (2014).
30. Stack, J. H., Whitney, M., Rodems, S. M. & Pollok, B. A. A ubiquitin-based tagging system for controlled modulation of protein stability. Nat. Biotechnol. 18, 1298-1302 (2000).
31. Sakaue-Sawano, A., Kobayashi, T., Ohtawa, K. & Miyawaki, A. Drug-induced cell cycle modulation leading to cell-cycle arrest, nuclear mis-segregation, or endoreplication. BMC Cell Biol. 12, 2 (2011).
32. Tomura, M. et al. Contrasting quiescent G0 phase with mitotic cell cycling in the mouse immune system. PLoS ONE 8, e73801 (2013).
33. Toettcher, J. E., Gong, D., Lim, W. A. & Weiner, O. D. Light control of plasma membrane recruitment using the Phy-PIF system. Methods Enzymol. 497, 409-423 (2011).
34. Gambetta, G. A. & Lagarias, J. C. Genetic engineering of phytochrome biosynthesis in bacteria. Proc. Natl. Acad. Sci. USA 98, 10566-10571 (2001).
35. Shu, X. et al. Mammalian expression of infrared fluorescent proteins engineered from a bacterial phytochrome. Science 324, 804-807 (2009).
36. Filonov, G. S. et al. Bright and stable near-infrared fluorescent protein for in vivo imaging. Nat. Biotechnol. 29, 757-761 (2011).
37. Shaner, N.C., Steinbach, P. A. & Tsien, R. Y. A guide to choosing fluorescent proteins. Nat. Methods 2, 905-909 (2005).
38. Arnold, K., Bordoli, L., Kopp, J. & Schwede, T. The SWISS-MODEL workspace: a web-based environment for protein structure homology modelling. Bioinformatics 22, 195-201 (2006).
39. Liu, J. Y., Jiang, T., Zhang, J. P. & Liang, D. C. Crystal structure of allophycocyanin from red algae Porphyra yezoensis at 2.2-Å resolution. J. Biol. Chem. 274, 16945-16952 (1999).
40. Schneidman-Duhovny, D., Inbar, Y., Nussinov, R. & Wolfson, H. J. PatchDock and SymmDock: servers for rigid and symmetric docking. Nucleic Acids Res. 33, W363-W367 (2005).
41. Andrusier, N., Nussinov, R. & Wolfson, H. J. FireDock: fast interaction refinement in molecular docking. Proteins 69, 139-159 (2007).
42. Larkin, M. A. et al. Clustal W and Clustal X version 2.0. Bioinformatics 23, 2947-2948 (2007).

43. Pettersen, E. F. et al. UCSF Chimera—a visualization system for exploratory research and analysis. J. Comput. Chem. 25, 1605-1612 (2004).
44. Wahleithner, J. A., Li, L. M. & Lagarias, J. C. Expression and assembly of spectrally active recombinant holophytochrome. Proc. Natl. Acad. Sci. USA 88, 10387-10391 (1991).
45. Lin, J. Y., Knutsen, P. M., Muller, A., Kleinfeld, D. & Tsien, R. Y. ReaChR: a red-shifted variant of channelrhodopsin enables deep transcranial optogenetic excitation. Nat. Neurosci. 16, 1499-1508 (2013).
46. Yu, D. et al. An improved monomeric infrared fluorescent protein for neuronal and tumour brain imaging. Nat. Commun. 5, 3626 (2014).
47. Schneider, C. A., Rasband, W. S. & Eliceiri, K. W. NIH Image to ImageJ: 25 years of image analysis. Nat. Methods 9, 671-675 (2012).

The examples set forth above are provided to give those of ordinary skill in the art a complete disclosure and description of how to make and use the embodiments of the compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

All headings and section designations are used for clarity and reference purposes only and are not to be considered limiting in any way. For example, those of skill in the art will appreciate the usefulness of combining various aspects from different headings and sections as appropriate according to the spirit and scope of the invention described herein.

All references cited herein are hereby incorporated by reference herein in their entireties and for all purposes to the same extent as if each individual publication or patent or patent application was specifically and individually indicated to be incorporated by reference in its entirety for all purposes.

Many modifications and variations of this application can be made without departing from its spirit and scope, as will be apparent to those skilled in the art. The specific embodiments and examples described herein are offered by way of example only, and the application is to be limited only by the terms of the appended claims, along with the full scope of equivalents to which the claims are entitled.

Listing of Sequences:

TeAPCα (SEQ ID NO: 1)
MKTGEQRVKIATLLSENEKKIVDKASQDLWRRRPDFIAPGGNAFGQRERA
LCLRDYGWYLRLITYGLLAGDKDPIESIGLIGVREMYNSLGVPVPGMVES
IRCLKEASLSLLDEEDAKETAPYFDYIIQAMS

R1 + PCB (SEQ ID NO: 2)
MKTGEQRVKIATLLSENEKKIVDKASQDLWRRRPDFIAPGGIAFGQRERA
LCLRDYGWYLRLITYGLLAGDKDPIESIGLIGVREMYNSLGVPVPGMVES
IRCLKEASLSLLDEEDAKETAPYFDYIIQAMS

R2-1 + PCB (SEQ ID NO: 3)
MKTGEQRVKIATLLSENEKKIVDKASQDLWRRRPDFIAPGGIAFGQRERA
LCLRDYGWYLRLITFCLLAGDKDPIESIGLIGVREMYNSLGVPVPGMVES
IRCLKEASLSLLDEEDAKETAPYFDYIIQAMS

R3-2 + PCB (SEQ ID NO: 4)
MKTGEQRVKIATLLSENEKKIVDKASQDLWRRRPDFIAPGGIAFGQRERA
LCLRDYGWYLRLITFCLLAGDKDPIESIGLIGIREMYNSLGVPVPGMMES
IRCLKEASLSLLDEEDAKETAPYFDYIIQAMS

R4-1 (SEQ ID NO: 5)
MKTGEQRVKIATLLSENEKKIVDKASQDLWRRRPDFIAPGGIAFSQRERA
LCLRDYRWYLHLITFCLLAGDKDPIESIGLIGIREMYNSLGVPVPGMMES
IRCLKEASLSLLDEEDAKETAPYFDYIIKAMS

R5-2 (SEQ ID NO: 6)
MKTCEQRVKIATLLSENEKKIVDKASQDLWRRRPDFIAPGGIAFSQRERA
LCLRDHRWYLHLITFCLLAGDKDPIESIGLIGIREMYNSLGVPVPGMMES
IRCLKEASLSLLDEEDAKETAPYFDYIIKAMS

R6-6 (SEQ ID NO: 7)
MKTCEQRVKIATLLSENEKKIVDKASQDLWRRRPDLIAPGGIAFSQRERA
LCLRDYGWYLHLITFCLLAGDKGPIESIGLIGIREMYNSLGVPVPGMMES
IRCLKEASLSLLDEEDAKETAPYFDYIIKAMS

R7-7 (SEQ ID NO: 8)
MKTCEQRVKIATLLSENKKKIVDKASQDLWRRHPDLIAPGGIAFSQRERA
LCLRDYGWYLHLITFCLLAGDKGPIESIGLIGIREMYNSLGVPVPGMMES
IRCLKEASLSLLDEEDAKETAPYFDYIIKAIS

R8-8 (SEQ ID NO: 9)
MKTCEQRVKIATLLSENKKKIVDKASQDLWRRHPDLIAPGGIAFSQRDRA
LCLRDYGWYLHLITFCLLAGDKGPIESIGLIGIREMYNSLGVPVPAMMES
IRCLKEASLSLLDEEDANETAPYFDYIIKAMS

R8-9 (SEQ ID NO: 10)
MKTCEQRVNIATLLSENKKKIVDKASQDLWRRRPDLIAPGGIAFSQRDRA
LCLRDYGWYLHLITFCLLAGDKGPIESIGLIGIREMYNSLGVPVPDMMES
IRCLKEASLSLLDEEDAKETAPYFDYIIKAMS

R10-10 (SEQ ID NO: 11)
MKTCEQRVNIATLLTENKKKIVDKASQDLWRRHPDLIAPGGIAFSQRDRA
LCLRDYGWYLHLITFCLLAGDKGPIESIGLIGIREMYNSLGVPVPAMMES
IRCLKEASLSLLDEEDANETAPYFDYIIKAMS

R11-2 (SEQ ID NO: 12)
MKTCEQRVNIATLLTENKKKIVDKASQDLWRRHPDLIAPGGIAFSQRDRA
LCLRDYGWYLHLITFCLLAGDKGPIESIGLISIREMYNSLGVPVPAMMES
IRCLKEASLSLLEEEDANETAPYFDYIIKAMS

SmURFP (SEQ ID NO: 13)
MKTSEQRVNIATLLTENKKKIVDKASQDLWRRHPDLIAPGGIAFSQRDRA
LCLRDYGWFLHLITFCLLAGDKGPIESIGLISIREMYNSLGVPVPAMMES
IRCLKEASLSLLDEEDANETAPYFDYIIKAMS

Listing of Sequences:

Consensus (SEQ ID NO: 14)
MKTCEQRVKIATLLSENKKKIVDKASQDLWRRRPDLIAPGGIAFSQRERA
LCLRDYGWYLHLITFCLLAGDKGPIESIGLIGIREMYNSLGVPVPGMMES
IRCLKEASLSLLDEEDAKETAPYFDYIIKAMS 23-amino-acid linker (SEQ ID NO: 15)
GHGTGSTGSGSSGTASSEDNNMA Linker sequence (SEQ ID NO: 16)
GGGGS Linker sequence (SEQ ID NO: 17)
GGGGSGGGGS Linker sequence (SEQ ID NO: 18)
GGGGSGGGGSGGGGS Linker sequence (SEQ ID NO: 19)
GGGGSGGGGSGGGGSGGGGS Linker sequence (SEQ ID NO: 20)
GGGGSGGGGSGGGGSGGGGSGGGGS

What is claimed:

1. A small ultra-red fluorescent protein (smURFP) variant polypeptide comprising an amino acid sequence selected from the group consisting of SEQ ID NO:4, SEQ ID NO:6, SEQ ID NO:8, SEQ ID NO:13, and SEQ ID NO:13 further comprising C52A and A96C mutations.

2. The smURFP variant polypeptide according to claim 1, wherein said smURFP variant polypeptide is a dimer comprising two smURFP variant polypeptides conjugated by a linker.

3. The smURFP variant polypeptide according to claim 2, wherein said linker is an amino-acid linker.

4. The smURFP variant polypeptide according to claim 3, wherein said amino-acid linker comprises 23 amino acids.

5. The smURFP variant polypeptide according to claim 1, wherein said smURFP variant polypeptide is a dimer comprising one smURFP conjugated to a second fluorescent protein by a linker.

6. The smURFP variant polypeptide according to claim 1, wherein said smURFP variant polypeptide is a dimer comprising one smURFP conjugated to a second smURFP.

7. The smURFP variant polypeptide according to claim 5, wherein said second fluorescent protein is selected from the group consisting of eGFP, mCherry, mCardinal, IFP1.4, IFP2.0, and iRFP713.

8. A nucleic acid encoding the smURFP variant polypeptide of claim 1.

9. An expression vector comprising the nucleic acid of claim 8.

10. An isolated host cell comprising the expression vector of claim 9.

11. A method of producing a smURFP comprising: a) culturing a host cell according to claim 10 under conditions wherein said polypeptide is produced; and b) purifying said polypeptide.

12. A biosensor comprising a smURFP according to claim 1.

* * * * *